US012502481B2

(12) United States Patent
Kim et al.

(10) Patent No.: US 12,502,481 B2
(45) Date of Patent: Dec. 23, 2025

(54) MEDICAMENT INJECTOR AND INTERCHANGEABLE CARTRIDGES THEREFOR

(71) Applicant: DIFINITY SOLUTIONS INC., Vancouver (CA)

(72) Inventors: David Sanghyuck Kim, Vancouver (CA); Damien Tak, Vancouver (CA)

(73) Assignee: DIFINITY SOLUTIONS INC., Vancouver (CA)

( * ) Notice: Subject to any disclaimer, the term of this patent is extended or adjusted under 35 U.S.C. 154(b) by 696 days.

(21) Appl. No.: 17/889,560

(22) Filed: Aug. 17, 2022

(65) Prior Publication Data

US 2023/0019820 A1 Jan. 19, 2023

Related U.S. Application Data

(63) Continuation of application No. PCT/CA2020/051157, filed on Aug. 24, 2020, which (Continued)

(51) Int. Cl.

*A61M 5/24* (2006.01)
*A61M 5/20* (2006.01)
*A61M 5/32* (2006.01)

(52) U.S. Cl.

CPC ........ *A61M 5/2033* (2013.01); *A61M 5/2455* (2013.01); *A61M 5/3202* (2013.01);

(Continued)

(58) Field of Classification Search

CPC .. A61M 2005/2414; A61M 2005/2403; A61M 2005/2407; A61M 2005/2411;

(Continued)

(56) References Cited

U.S. PATENT DOCUMENTS 1,557,836 A 10/1925 Hein
1,757,809 A * 5/1930 Montuori ................ A61M 5/24 604/235

(Continued)

FOREIGN PATENT DOCUMENTS

CA 2049972 C 5/2000
DE 688650 C * 2/1940

(Continued)

OTHER PUBLICATIONS

Supplementary European Search Report issued on European Patent Application No. 20921939 dated Mar. 1, 2024.

(Continued)

*Primary Examiner* — William R Carpenter
(74) *Attorney, Agent, or Firm* — Nicholas Garner; Oyen Wiggs Green & Mutala LLP

(57) ABSTRACT

The present invention relates to a medicament injector including an applicator with a cartridge-accepting receptacle, and interchangeable, pre-filled medicament-containing cartridges. Each cartridge includes a barrier member having a closed position in which access to the medicament is inhibited. The barrier member is movable from the closed position to an open position, in which the medicament is accessible via the applicator for administration, when the cartridge is inserted into the receptacle. The barrier member is moves back to the closed position when the cartridge is automatically removed from the receptacle once the medication is delivered. This allows for plurality of pre-filled medicament cartridges to be selected on demand via a need-based scenario for quick assembly with the medicament injector for use in various clinical scenarios to reduce the bulk, errors, complexity, and steps in medicament delivery while increasing the versatility, safety, and speed of medicament delivery in time critical situations.

22 Claims, 32 Drawing Sheets

Related U.S. Application Data is a continuation-in-part of application No. 16/800,804, filed on Feb. 25, 2020, now Pat. No. 11,759,570.

(52) U.S. Cl.
CPC ... *A61M 2005/2433* (2013.01); *A61M 5/2459* (2013.01); *A61M 2005/2481* (2013.01)

(58) Field of Classification Search
CPC ................ A61M 5/285; A61M 5/2455; A61M 2005/2481
See application file for complete search history.

(56) References Cited

U.S. PATENT DOCUMENTS

| | | | |
|---|---|---|---|
| 2,922,419 A | 1/1960 | Bednarz | |
| 3,134,380 A | 5/1964 | Armao | |
| 3,378,008 A | 4/1968 | Ogle | |
| 3,580,251 A | 5/1971 | Guiriec | |
| 3,659,587 A | 5/1972 | Baldwin | |
| 3,659,602 A | 5/1972 | Cloyd | |
| 3,850,174 A | 11/1974 | Ayres | |
| 4,725,267 A | 2/1988 | Vaillancourt | |
| 4,735,618 A | 4/1988 | Hagen | |
| 4,747,829 A | 5/1988 | Jacob et al. | |
| 4,767,413 A | 8/1988 | Haber et al. | |
| 4,929,237 A | 5/1990 | Medway | |
| 5,098,382 A * | 3/1992 | Haber | A61M 5/31501 604/110 |
| 5,114,404 A | 5/1992 | Paxton et al. | |
| 5,135,510 A | 8/1992 | Maszkiewicz et al. | |
| 5,147,323 A | 9/1992 | Haber et al. | |
| 5,195,983 A | 3/1993 | Boese | |
| 5,222,945 A | 6/1993 | Basnight | |
| 5,269,761 A | 12/1993 | Stehrenberger et al. | |
| 5,279,586 A | 1/1994 | Balkwill | |
| 5,354,284 A | 10/1994 | Haber et al. | |
| 5,425,715 A | 6/1995 | Dalling et al. | |
| 5,472,430 A | 12/1995 | Vaillancourt et al. | |
| 5,637,094 A | 6/1997 | Stewart, Jr. et al. | |
| 5,695,472 A | 12/1997 | Wyrick | |
| 5,893,845 A | 4/1999 | Newby et al. | |
| 5,980,494 A | 11/1999 | Malenchek et al. | |
| 6,090,082 A | 7/2000 | King et al. | |
| 6,416,497 B1 | 7/2002 | Kirk | |
| 6,676,641 B2 | 1/2004 | Woodard, Jr. et al. | |
| 6,855,129 B2 | 2/2005 | Jensen et al. | |
| 6,926,697 B2 | 8/2005 | Malenchek | |
| 7,648,483 B2 | 1/2010 | Edwards et al. | |
| 7,717,877 B2 | 5/2010 | Lavi et al. | |
| 7,799,002 B2 | 9/2010 | Dillard, III | |
| 9,028,453 B2 | 5/2015 | Jennings | |
| 9,440,026 B2 | 9/2016 | Wozencroft | |
| 10,610,646 B2 | 4/2020 | Schmid et al. | |
| 10,646,654 B2 | 5/2020 | Mosebach et al. | |
| 11,160,929 B2 | 11/2021 | Dahmani | |
| 11,213,631 B2 | 1/2022 | Kim | |
| 11,759,570 B2 | 9/2023 | Kim et al. | |
| 2002/0010432 A1 | 1/2002 | Klitmose | |
| 2005/0171477 A1 | 8/2005 | Rubin et al. | |
| 2005/0283120 A1 | 12/2005 | Wang | |
| 2010/0083963 A1 | 4/2010 | Wharton et al. | |
| 2010/0137808 A1 | 6/2010 | Wilmot et al. | |
| 2015/0011943 A1 * | 1/2015 | Holmes | A61M 5/3204 604/191 |
| 2016/0184519 A1 | 6/2016 | Blundred et al. | |
| 2018/0126083 A1 | 5/2018 | Schmid et al. | |
| 2018/0154081 A1 * | 6/2018 | Bar-El | A61M 5/31571 |
| 2018/0185584 A1 | 7/2018 | Cowe et al. | |
| 2018/0361069 A1 | 12/2018 | Schader et al. | |
| 2018/0369498 A1 | 12/2018 | Schader et al. | |
| 2023/0019820 A1 | 1/2023 | Kim et al. | |
| 2023/0372621 A1 | 11/2023 | Kim et al. | |

FOREIGN PATENT DOCUMENTS

| | | |
|---|---|---|
| EP | 3311864 A1 | 4/2018 |
| EP | 3122400 B1 | 7/2019 |
| EP | 4074354 A1 | 10/2022 |
| FR | 2728172 B1 | 6/1997 |
| GB | 2216801 A | 10/1989 |
| WO | 1991018634 A1 | 12/1991 |
| WO | 1993013817 A1 | 7/1993 |
| WO | 1994004205 A1 | 3/1994 |
| WO | 1995029721 A1 | 11/1995 |
| WO | 2013065055 A1 | 5/2013 |
| WO | 2016210404 A1 | 12/2016 |

OTHER PUBLICATIONS

International Search Report issued on PCT/CA2024/050390 dated Dec. 13, 2024.

International Search Report issued on PCT/CA2020/051157 dated Oct. 15, 2020.

Examiner's Report for Canadian Patent Application No. 3,007,875, dated Apr. 11, 2019.

* cited by examiner

MEDICAMENT INJECTOR AND INTERCHANGEABLE CARTRIDGES THEREFOR

FIELD OF THE INVENTION

The present invention relates to a medicament injector and interchangeable cartridges assembly therefor. In particular, the invention relates to a medicament injector configured to selectively receive various interchangeable medicament-carrying cartridges.

DESCRIPTION OF THE RELATED ART

United States Patent Application Publication No. 2018/0126083A1 to Schmid et al. discloses an adjustable injection device for administering a substance. The device includes a housing with an array of fastening points and at least two housing-like shells, each having at least one holding device and at least one blocking device for attaching to the housing. The holding device of a first shell can be attached to a fastening point, and the holding device of a second shell can be attached to a further fastening point. The holding device of the first shell is prevented from disengagement therefrom by the blocking device of the second shell, and the holding device of the second shell is prevented from disengagement therefrom by a blocking device of a further shell, or, in the event that the injection device has only two shells, is prevented from disengagement from the further fastening point by a blocking device of the first shell whereby the shells are non-detachably connected to the housing.

International Patent Application Publication No. WO 2013/065055 A1 to Lev discloses an electronic autoinjector apparatus for use with a replaceable pre-filled cassette containing liquid contents for administrating a liquid drug to a patient. The electronic autoinjector apparatus includes a handheld pen-like electronic autoinjector having an autoinjector housing with an open ended cassette holder for manual sliding installation of a cassette therein and sliding removal therefrom. The electronic autoinjector apparatus also includes a remote control unit having a base with a storage cavity for snugly receiving the electronic autoinjector when not in use and a cover for closing the base, and a user control interface for operating the electronic autoinjector apparatus.

International Patent Application Publication No. WO 2016/210404 A1 to Lev discloses an injector assembly for automatically delivering a dose of a medicament to a subject. The assembly includes an activation switch for initiating automatic delivery of the dose of the medicament. The assembly includes a needle aperture at a distal end of the injector assembly configured for a needle to pass therethrough. The assembly includes a plunger drive mechanism for applying pressure to a plunger assembly, the plunger drive mechanism including a motor operably connected to the activation switch, and an actuator operably connected to the motor and the plunger assembly. The assembly includes a surface for operatively connecting to at least a portion of a removable cartridge module, the removable cartridge module including: a needle housing for dictating a range of injection depths possible. The assembly includes a plunger housing for aligning the plunger assembly with the plunger drive mechanism. The assembly includes an identification element containing a code associated with a pre-filled cartridge and/or medicament contained within, and a cavity for reversibly securing the pre-filled cartridge. The assembly includes at least one engagement feature for securing the removable cartridge module to the surface. The assembly includes a cartridge drive assembly for moving the pre-filled cartridge axially between the proximal and distal end of the injector assembly, the cartridge drive assembly including at least one gear element operably connected to the motor and the activation switch.

Giving medicines is cumbersome and slow as it requires multiple components and multiple steps to draw up the medication into the syringe and deliver to the patient via an injection with needle or through an intravenous line. The steps involved to deliver the medication include utilization of the syringe/plunger, needle, and medication combination. The clinical provider must draw up the correct medication at the dose appropriate for each patient and clinical situation. Further, the common delivery routes include IM (Intramuscular), IV (Intravenous), IN (Intranasal), and IO (Intraosseous) routes. Given the complexities and various steps involved, this can cause significant time delay and operational errors that can have detrimental outcomes for patients. In a non-hospital clinical setting such as pre-hospital/transport medicine, aerospace medicine, bystander first-aid, and military medicine, the advantage of reduced bulk/components, improved versatility, and ease of use is also critical. There may accordingly be a need for an employed universal medicament injector that interfaces seamlessly with selectable and standardized interchangeable medicament cartridges depending on the clinical need and situation.

BRIEF SUMMARY OF INVENTION

The present invention provides, and it is an object to provide, an improved medicament injector and interchangeable cartridges therefor.

There is accordingly provided a medicament injector according to a first aspect. The medicament injector includes an applicator with a cartridge-accepting receptacle. The medicament injector includes an interchangeable cartridge with a body shaped to receive or contain a medicament within an interior thereof. The cartridge includes at least one barrier member having a closed position in which access to the medicament is inhibited. The barrier member is movable from the closed position to an open position, in which the medicament is accessible via the applicator, when the cartridge is inserted into the cartridge-accepting receptacle. The barrier member is moves back to the closed position when the cartridge is removed from the cartridge-accepting receptacle.

There is also provided a medicament injector according to a second aspect. The medicament injector includes an applicator with a cartridge-accepting receptacle. The medicament injector interacts with an interchangeable cartridge with a body shaped to receive or contain a medicament within an interior thereof. The cartridge includes a valve coupled to the body. Insertion of the cartridge into the cartridge-accepting receptacle actuates the valve to move from a closed position, in which access to the medicament is inhibited, to an open position in which the medicament is accessible via the applicator.

There is further provided a medicament injector according to a third aspect. The medicament injector includes a needle. The medicament injector includes a cartridge-accepting receptacle coupled to the needle. The medicament injector includes an interchangeable cartridge having an interior in which a medicament is prefilled, contained or received. The cartridge has a pre-injection mode in which access to the medicament is inhibited. Insertion of the cartridge into the cartridge-accepting receptacle causes the cartridge to move from the pre-injection mode to an injection mode in which the medicament is accessible via the needle.

There is additionally provided a kit comprising a plurality of interchangeable cartridges with variable medicaments and one of the above set out medicament injectors.

There is yet further provided a medicament injector according to a fourth aspect. The medicament injector includes an applicator with a cartridge-accepting receptacle. The medicament injector includes a plurality of interchangeable cartridges containing pre-filled amounts of one or more medicaments therewithin. The medicament injector includes a reversible barrier mechanism which inhibits access to the medicament until a selected one of said cartridges is inserted into the cartridge-accepting receptacle.

BRIEF DESCRIPTION OF DRAWINGS

The invention will be more readily understood from the following description of preferred embodiments thereof given, by way of example only, with reference to the accompanying drawings, in which.

DESCRIPTION OF THE PREFERRED EMBODIMENTS

Figure 1:
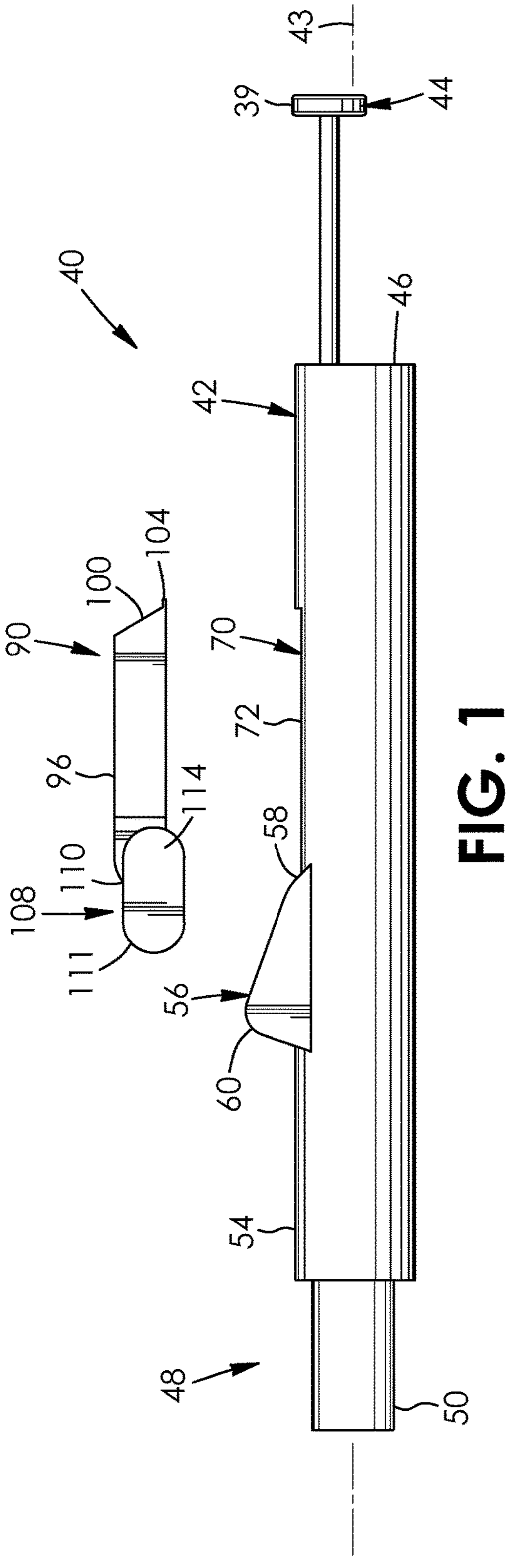
FIG. 1 is a side elevation view of a medicament injector according to one embodiment, the medicament injector comprising an applicator and an interchangeable medicament-carrying cartridge positioned above the applicator, the applicator including a plunger adjacent to a first end thereof and a protective needle assembly extending about a needle (not shown) adjacent to a second end thereof, the cartridge including a hollow body and a valve pivotally coupled to the body, with the valve including a valve actuator shown in a closed position.

Referring to the drawings and first to FIG. 1, there is shown a medicament injector 40.

Figure 2:
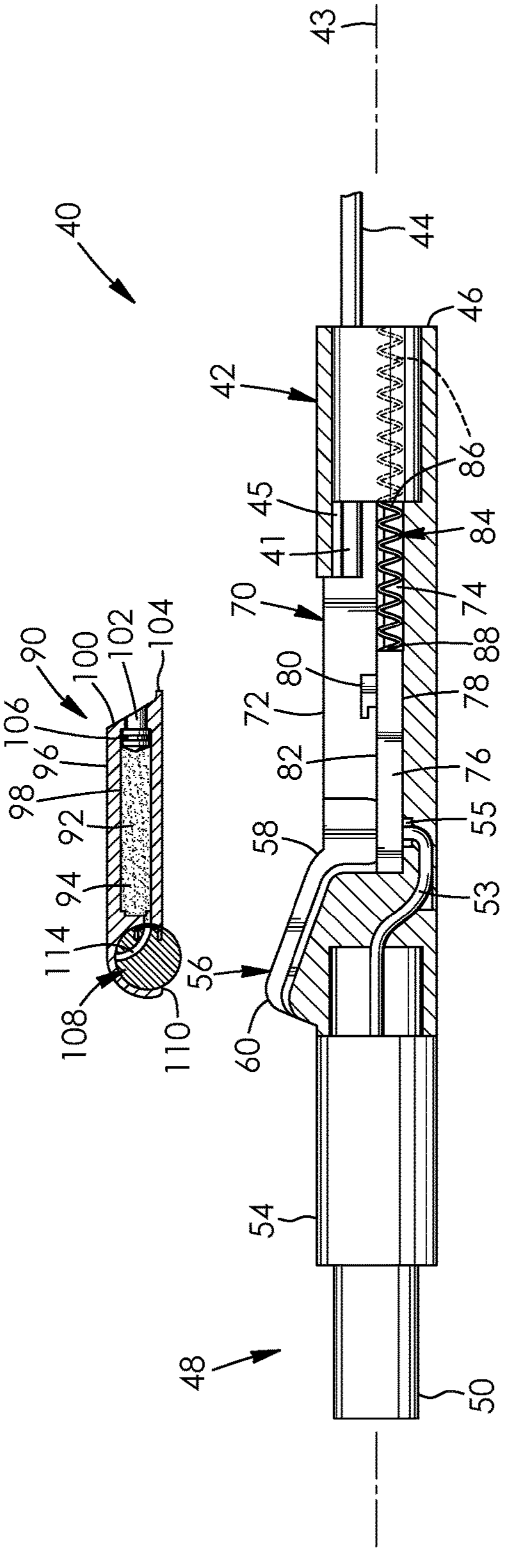
FIG. 2 is a side elevation view of the medicament injector of FIG. 1, with the applicator and the cartridge being shown in section to reveal the interior thereof.
Figure 12:
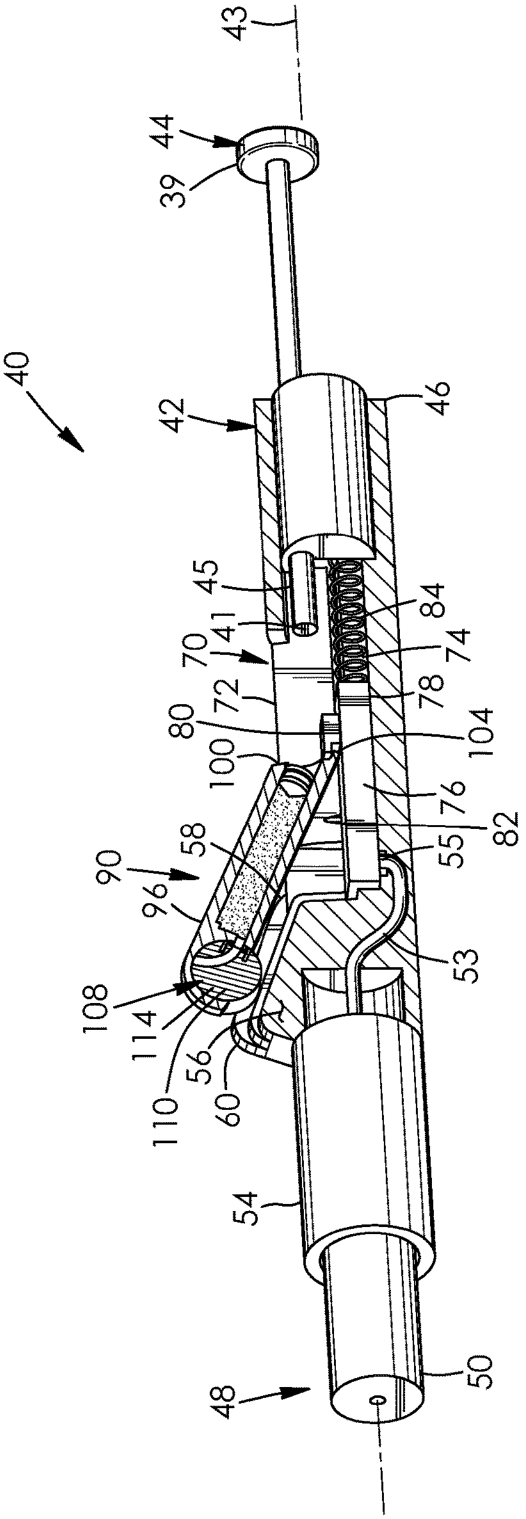
FIG. 12 is a side perspective view of the medicament injector of FIG. 10 with the applicator and cartridge shown in section to reveal the interior thereof

The medicament injector includes a cartridge applicator 42 which is generally a cylindrical body that is hollow at least in part and which extends along a longitudinal axis 43. The applicator includes a depressor, in this example plunger 44 adjacent to a first end 46 thereof. As seen in FIG. 12, the plunger has a first or outer end, in this example a gripping end 39 and a second or inner end, in this example a distal end 41. The plunger 44 is movable from a loaded position shown in FIG. 1 to an injecting-position shown in FIG. 19. As seen in FIG. 2, the applicator 42 includes a depressor bore, in this example a plunger bore 45 that, in this embodiment, is offset from axis 43 and which extends parallel with the axis 43 in this example. The plunger bore is extends to end 46 of the applicator and is shaped to slidably receive plunger 44 therewithin.

The applicator 42 includes a needle protection assembly 48 adjacent to a second end 50 thereof. The needle protection assembly selectively extends about needle 52 seen in FIGS. 18 and 19. The parts and functioning of an example of a suitable needle protection assembly in this regard is described in U.S. patent application Ser. No. 16/800,804, the disclosure of which is incorporated herein by reference and priority to which is claimed.

Figure 15:
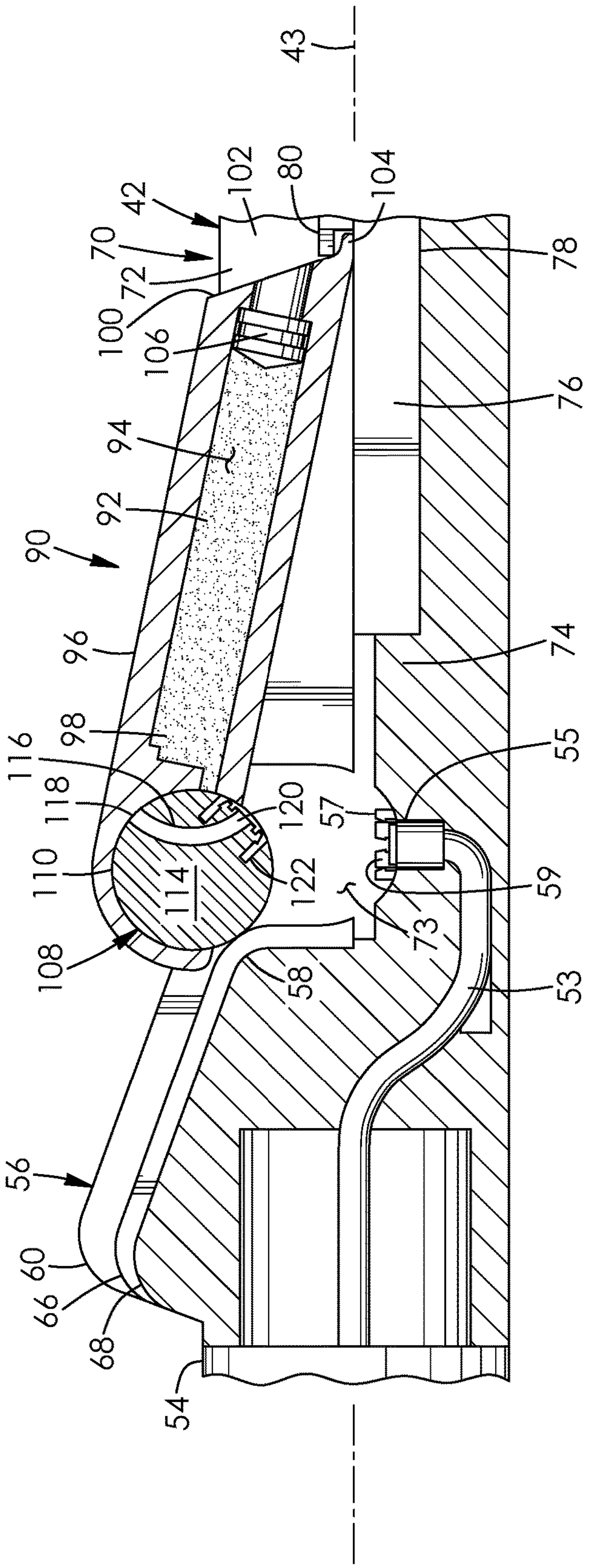
FIG. 15 is an enlarged side elevation view of the medicament injector of FIG. 14 shown in fragment and shown in section to reveal the interior thereof, with the valve actuator not being shown, with the valve body of the valve shown closer to the cartridge-accepting receptacle than in FIG. 14.
Figure 18:
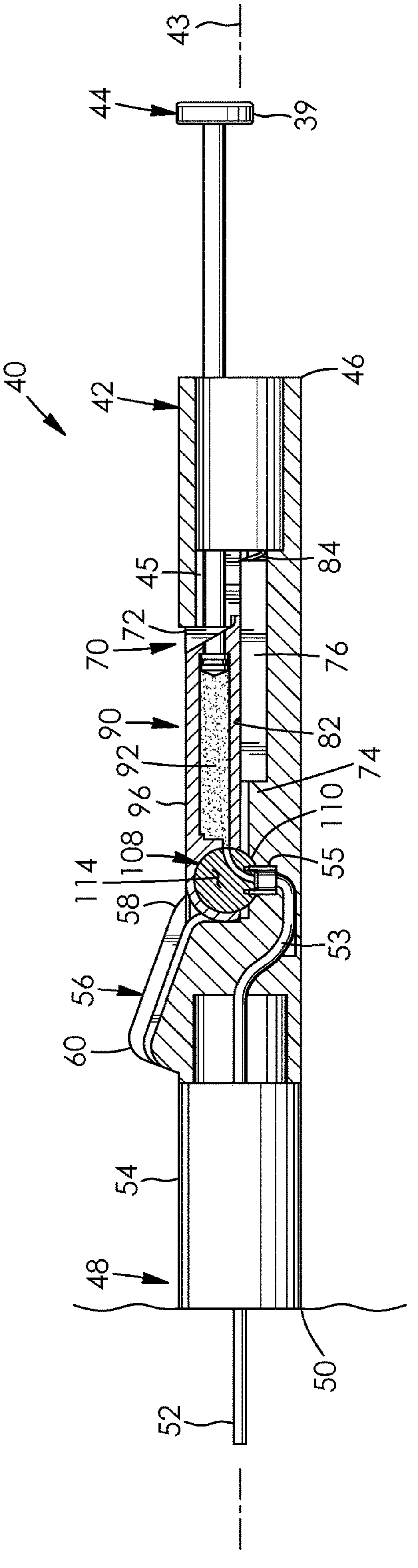
FIG. 18 is a side elevation view of the medicament injector of FIG. 17 with the needle shown inserted into a patient, with the protective needle assembly shown in a retracted position, and with the plunger shown in a loaded position.

Referring to FIG. 2, the applicator 42 includes a conduit 53 having a first end (not shown) configured to couple with the needle 52 of FIG. 18. As seen in FIG. 15, the conduit has a second end 55. The conduit comprises one of at least one male member and at least one female member, in this example comprising a plurality of male members, in this case circumferentially spaced-apart detents 57 at said end 55, with each said detent having a radially-inwardly extending catch 59 in this example.

Figure 4:
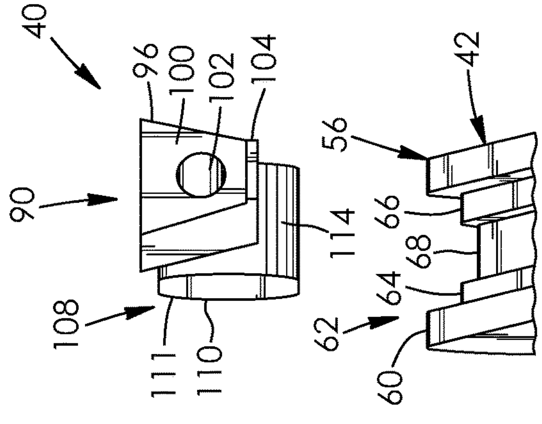
FIG. 4 is a perspective view of the cartridge of FIG. 1 shown from a plunger-input end thereof, together with a cartridge-accepting receptacle of the applicator of FIG. 1 shown in fragment.
Figure 5:
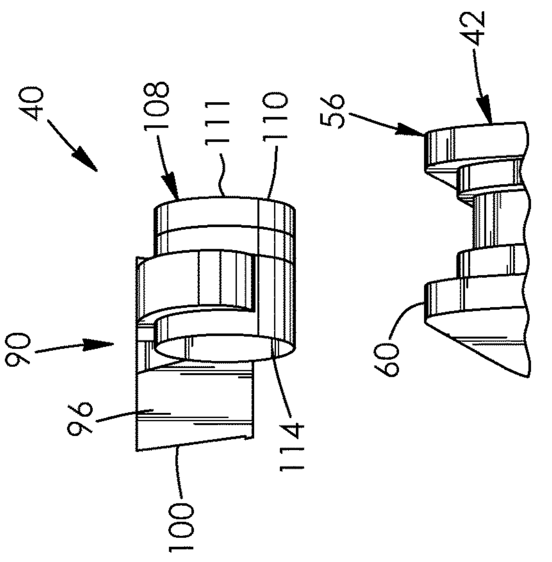
FIG. 5 is a perspective view of the cartridge of FIG. 1 shown from a valve actuator end thereof, together with the cartridge-accepting receptacle of the applicator of FIG. 1 shown in fragment.
Figure 6:
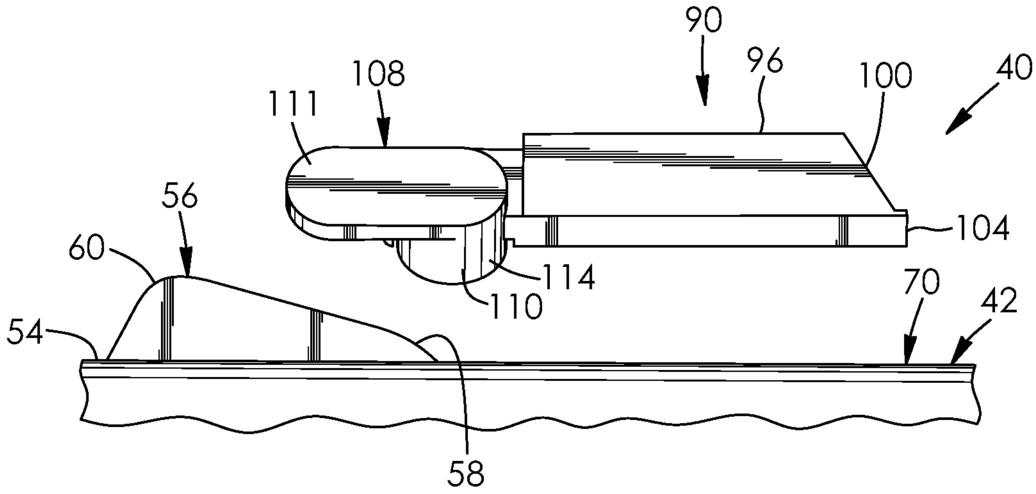
FIG. 6 is a bottom, side perspective view of the cartridge of FIG. 1, together with the cartridge-accepting receptacle of the applicator of FIG. 1 being shown in fragment.

Referring back to FIG. 1, the applicator 42 includes a side wall, in this example an annular side wall 54 and a protuberance, in this example a ramp 56 which is coupled to and extends outwards from said side wall. The ramp is generally triangular in side profile in this example and is between the ends 46 and 50 of the applicator. The ramp 56 has a thin end 58 adjacent to the side wall 54 of the applicator 42 and a larger or thicker end 60 radially spaced-apart further from the side wall of the applicator. As seen in FIG. 4, the ramp 56 has a recessed track 62 thereon comprising a pair of spaced-apart, recessed shoulders 64 and 66 between which extends a further recessed, centrally-positioned channel 68.

Figure 3:
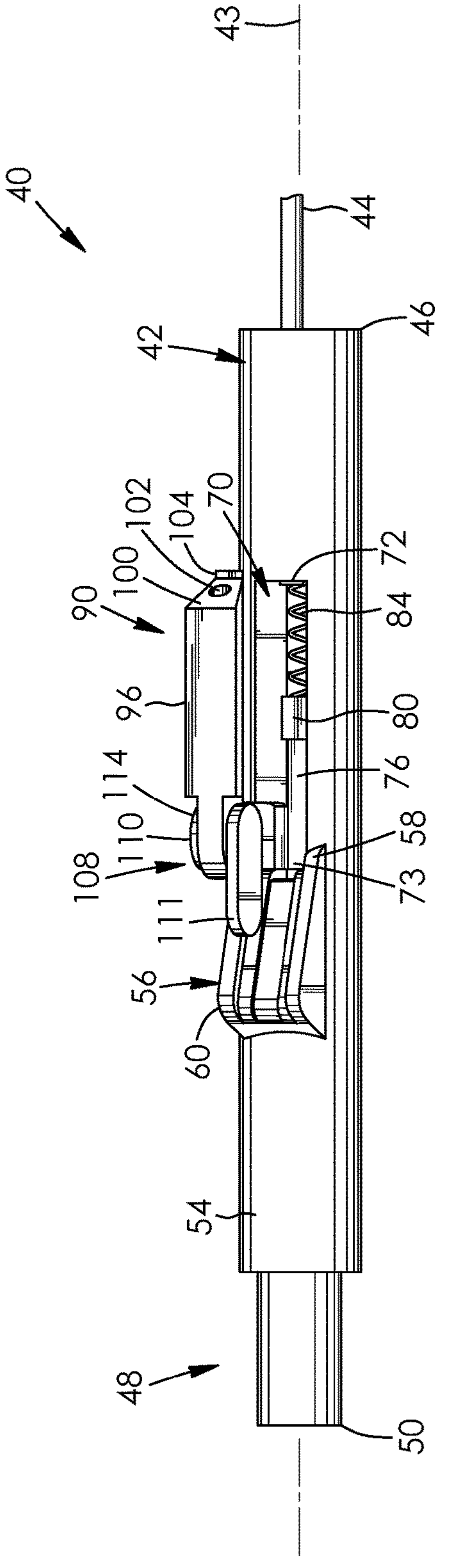
FIG. 3 is a top, side perspective view of the medicament injector of FIG. 1.
Figure 10:
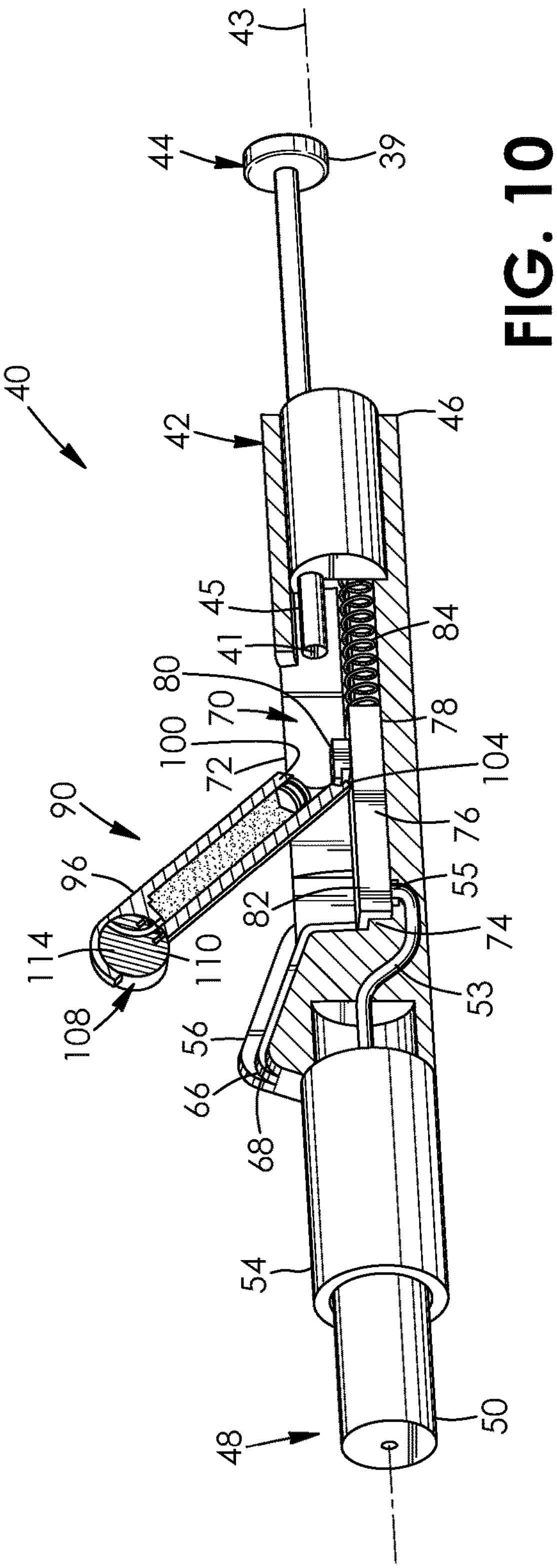
FIG. 10 is a side perspective view of the medicament injector of FIG. 9 with the applicator and cartridge shown in section to reveal the interior thereof, with the medicament injector further including a retaining member having a catch and being shown in an extended position, and with the protrusion of the cartridge at the plunger-input end thereof engaging said catch.
Figure 19:
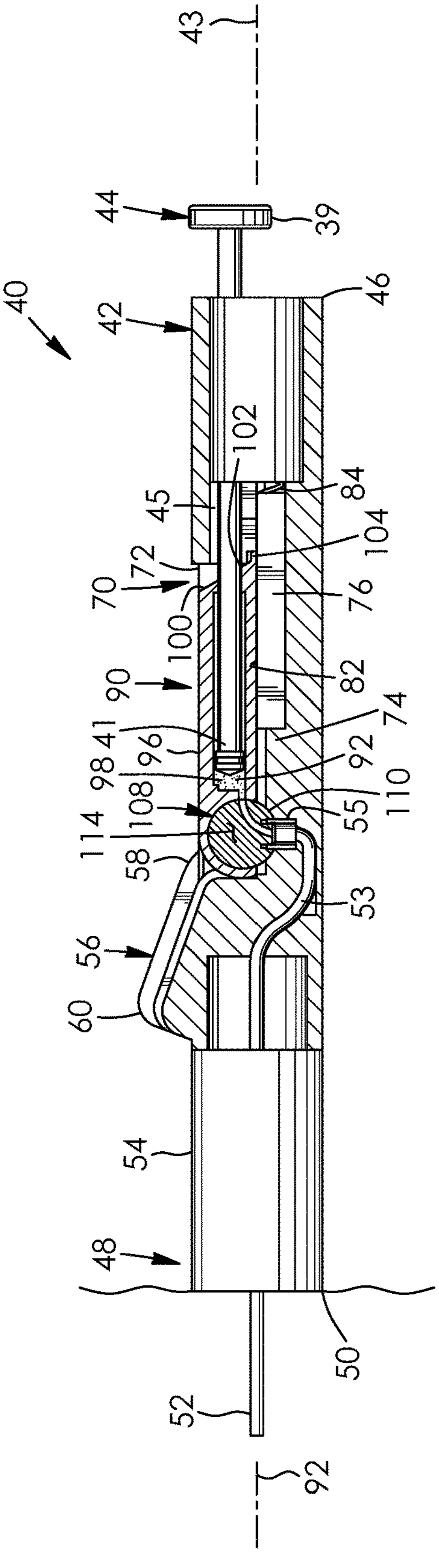
FIG. 19 is a side elevation view of the medicament injector of FIG. 18 with the plunger shown in an injecting-position so as to direct medicament from within the cartridge through the valve body, through the medicament-output end of the cartridge, through the conduit of the applicator, out of the needle and into the patient.

As seen in FIG. 10, the applicator 42 includes a cartridge-accepting receptacle 70 between the ends 46 and 50 thereof. As seen in FIG. 19, the cartridge-accepting receptacle is coupled to the needle 52. Referring back to FIG. 10, the cartridge-accepting receptacle has an opening 72 which extends through annular side wall 54 of the applicator and which is generally rectangular in shape in this example. The cartridge-accepting receptacle 70 is between the ramp 56 and the plunger bore 45 in this example, and is in fluid communication with the plunger bore. The cartridge-accepting receptacle extends in a direction parallel with the longitudinal axis 43 of the applicator 42 in this example. Referring to FIGS. 3 and 15, the cartridge-accepting receptacle 70 has an enlarged portion 73 adjacent to the ramp 56 in this example. The enlarged portion is generally annular in shape in this case.

Figure 16:
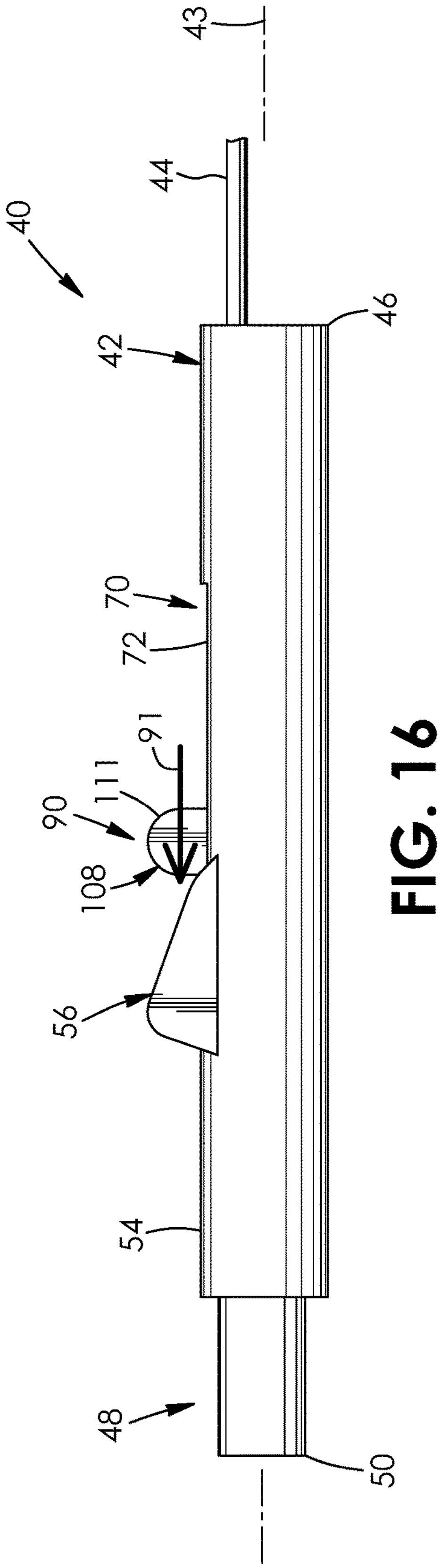
FIG. 16 is a side elevation view of the medicament injector of FIG. 1, with the cartridge shown fully inserted within the cartridge-accepting receptacle of the applicator.

As seen in FIG. 15, the applicator 42 includes an inner track 74 which is in communication with the cartridge-accepting receptacle 70 and which extends between the ramp 56 and end 46 of the applicator seen in FIG. 16. Referring back to FIG. 15, the track is generally a rectangular prism in shape in this example and extends parallel with longitudinal axis 43 of the applicator 42.

As seen in FIG. 12, the medicament injector 40 includes a cartridge retaining member 76. The retaining member is shaped to slidably engage with inner track 74 of the applicator 42 via an inverse u-shaped bottom 78 in this example. The retaining member is elongate and extends parallel with the longitudinal axis 43 of the applicator 42 in this example. The retaining member 76 includes one of a catch and protrusion, in this example a catch 80 coupled to and extending upwards from a top 82 thereof.

As seen in FIG. 2, the retaining member 76 is biased towards a closed or extended position, in which the catch extends within the cartridge-accepting receptacle 70, via a resilient member, in this example a spring 84. The spring extends along the inner track 74 in this example, with a first end 86 which abuts the applicator 42 adjacent to the distal end 41 of the plunger 44 in this example. The spring 84 has a second end 88 which abuts the retaining member 76.

Figure 17:
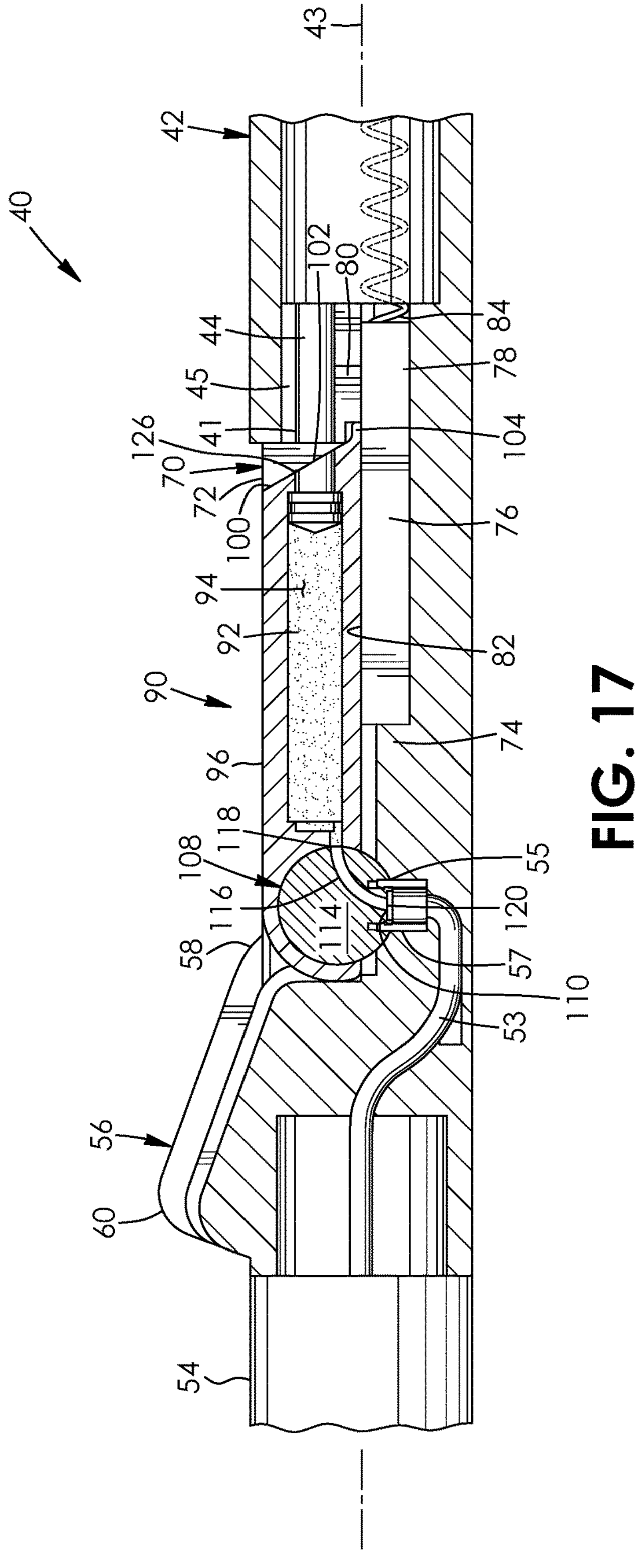
FIG. 17 is a side elevation view of the medicament injector of FIG. 16 with the applicator and cartridge shown in section to reveal the interior thereof, with the retaining member shown in a retracted position and shown retaining the cartridge in place, with the plunger-input end of the cartridge in communication with the plunger of the applicator, with the valve in the open position so as to enable the interior of the cartridge to be in communication with a needle conduit of the applicator, and with detents of the applicator shown coupling to a complementary recess of the valve body of the cartridge to further retain the cartridge in place.

The retaining member is movable along inner track 74 from the extended position seen in FIG. 2, to an open or retracted position seen in FIG. 17. The catch 80 is free of the cartridge-accepting receptacle 70 when the retaining member is in its retracted position.

Referring to FIG. 1, the medicament injector 40 includes a plurality of interchangeable cartridges, as shown by interchangeable cartridge 90. The cartridges may be referred to as replaceable cartridges. Referring to FIG. 2, cartridge 90 receives a medicament 92 within an interior 94 thereof. The cartridge includes an elongate, hollow body 96 with a bore 98 within which the medicament is contained and received. As seen in FIG. 17, the elongate body extends parallel with the longitudinal axis 43 of the applicator 42 when the cartridge 90 is fully inserted into the cartridge-accepting receptacle 70.

Referring to FIG. 1, the cartridge has a first and in this example plunger-input end 100 that is angled in this example. As seen in FIG. 4, the plunger-input end of the cartridge is in the shape of an isosceles trapezoid in this example and has an opening 102. Referring to FIG. 19, bore 98 is shaped to slidably receive distal end 41 of the plunger 44 via the opening 102 of the plunger-input end 100 of the cartridge 90. Referring back to FIG. 1, the cartridge includes one of a catch or a protrusion, in this example a protrusion 104. The protrusion is generally a rectangular prism in shape in this example.

Figure 13:
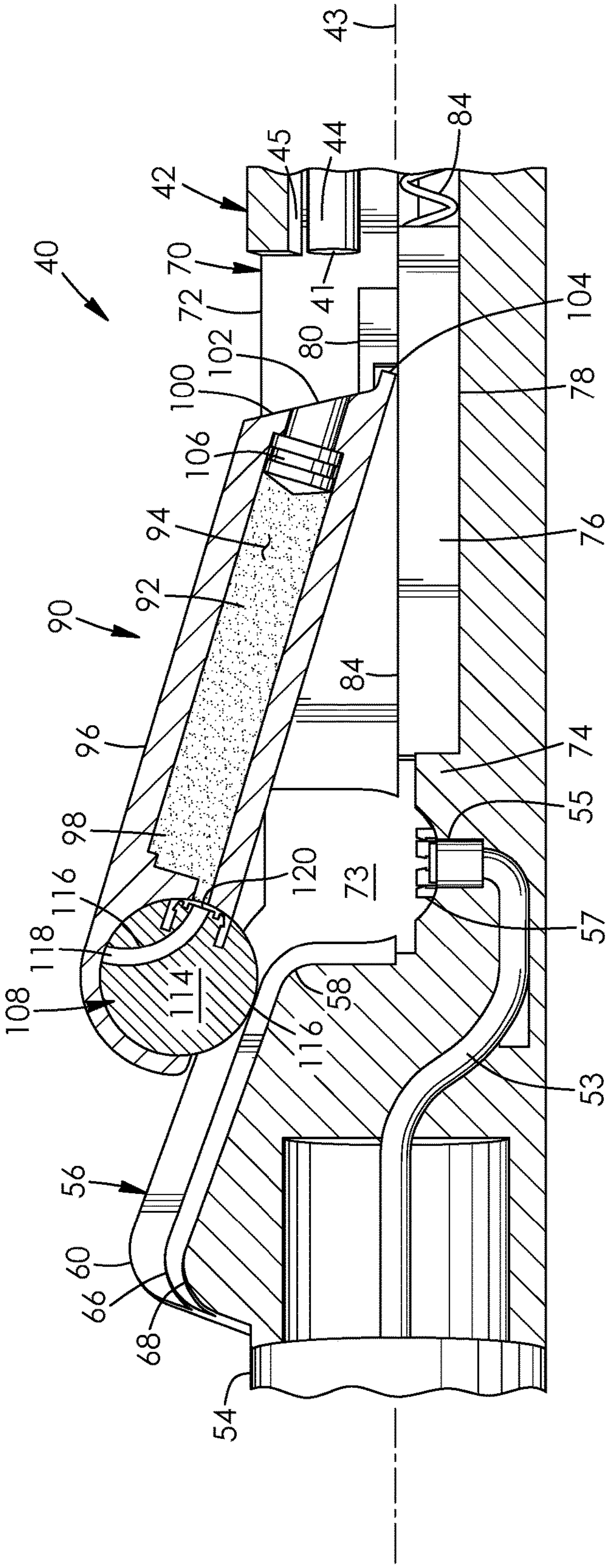
FIG. 13 is an enlarged side elevation view of the medicament injector of FIG. 1 shown in fragment and shown in section to reveal the interior thereof, with the valve actuator not being shown, with a valve body of the valve shown inserted yet further into the cartridge-accepting receptacle than in FIG. 12, and with the valve shown in its closed position.

As seen in FIG. 13, the cartridge 90 includes a piston member, in this example a piston 106 sealably disposed within the bore 98 thereof. The piston is longitudinally movable along the bore and is positioned between the opening 102 of the plunger-input end 100 of the cartridge and the interior 94 of the cartridge.

As seen in FIG. 1, the cartridge 90 includes a barrier member, in this example valve 108 at a medicament-output end 110 thereof. The piston 106 is positioned between ends 100 and 110 of the cartridge. The valve 108 is pivotably coupled and thus rotatable relative to the body 96 of the cartridge 90.

Figure 7:
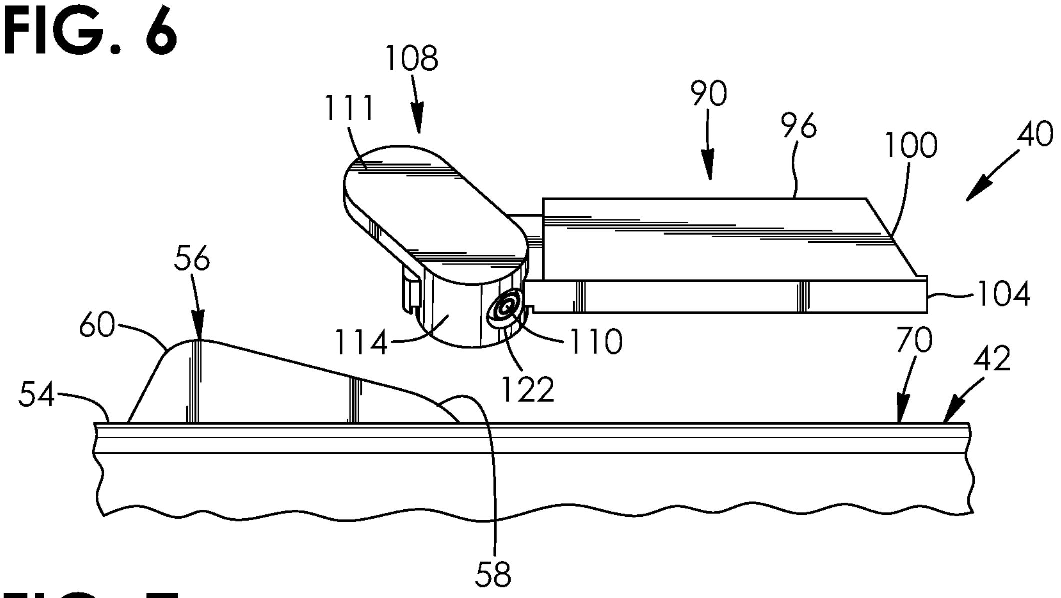
FIG. 7 is a bottom, side perspective view of the cartridge of FIG. 1, together with the cartridge-accepting receptacle of the applicator of FIG. 1 being shown in fragment, with the valve actuator of the cartridge shown partially actuated.
Figure 8:
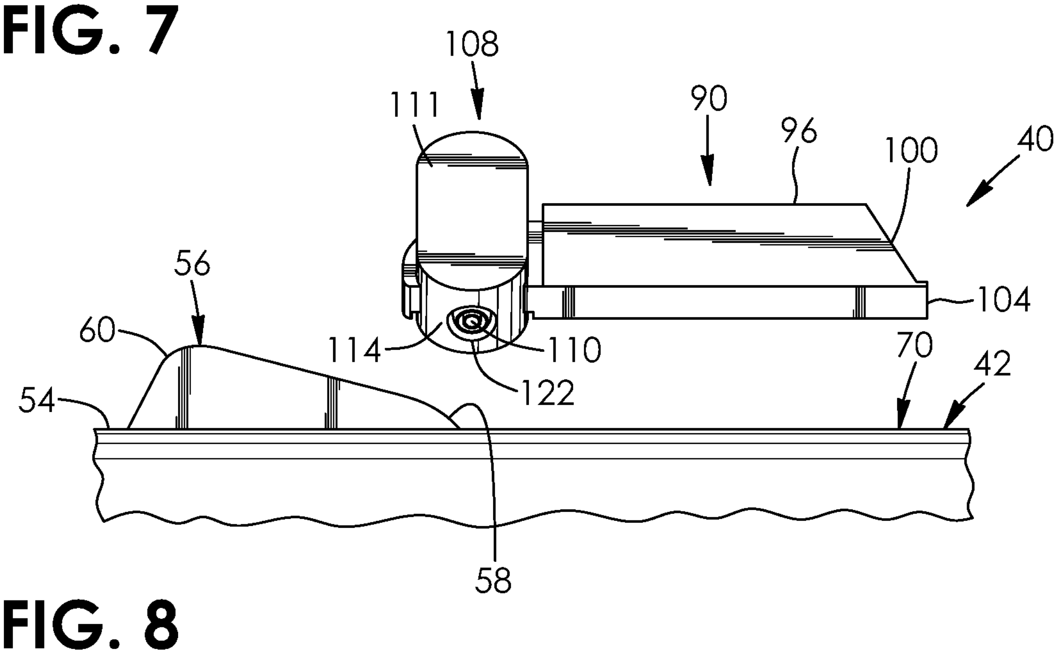
FIG. 8 is a bottom, side perspective view of the cartridge of FIG. 1, together with the cartridge-accepting receptacle of the applicator of FIG. 1 being shown in fragment, with the valve actuator of the cartridge shown fully actuated.
Figure 9:
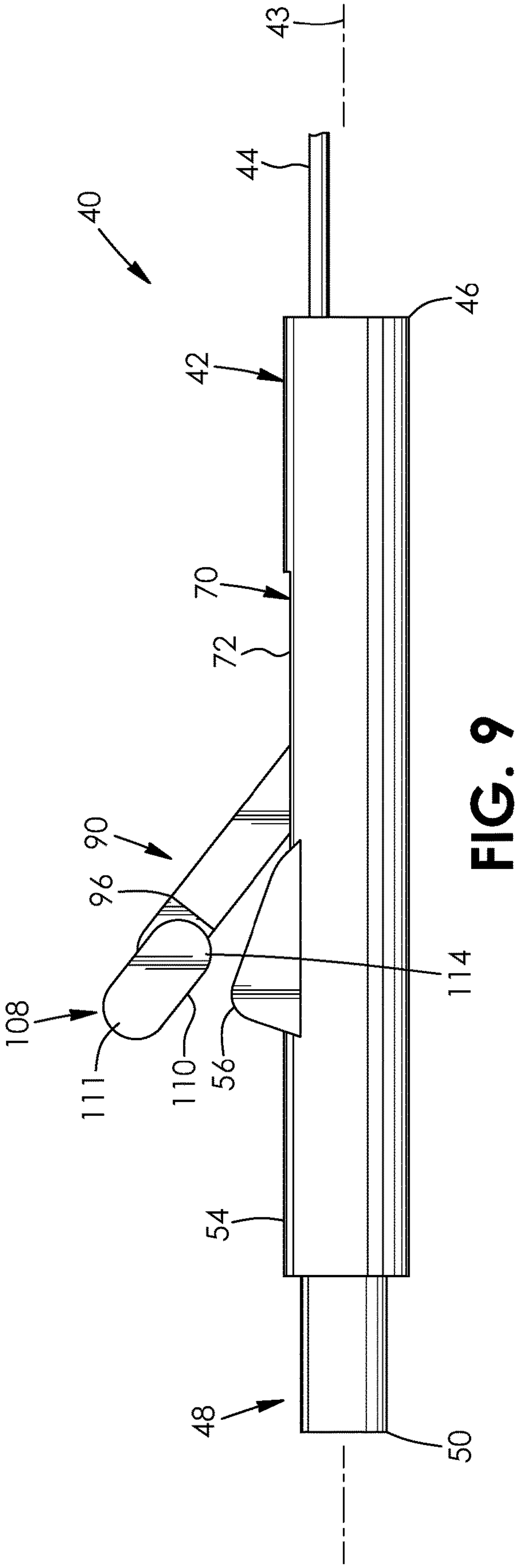
FIG. 9 is a side elevation view of the medicament injector of FIG. 1, with the cartridge shown in the process of being inserted within the cartridge-accepting receptacle of the applicator via the plunger-input end of the cartridge.

The valve include a valve actuator, in this example an elongate lever 111 that pivotally couples to the body of the cartridge. The lever is obround in side view in this example. As seen in FIG. 15, the valve 108 includes a valve body 114 that is generally cylindrical in side view in this example. The valve includes a conduit 116 which is arcuate-shaped in this example and which extends through the valve body. The conduit of the valve 108 has an inlet 118 and an outlet 120. The valve includes a member shaped to mate with the detents, in this example a recess 122 of the valve body 114 which are adjacent to outlet 120 of the conduit 116. As seen in FIG. 7, the recess is annular in this example.

Referring to FIGS. 1 and 2, the valve 108 has a closed position in which fluid communication between the hollow body 96 and the medicament-output end 110 of the cartridge 90 is inhibited. This is a pre-injection mode of the cartridge and the valve thus inhibits access to the medicament 92 seen in FIG. 1 when the cartridge 90 is in the pre-injection mode. As seen in FIGS. 13 and 15, fluid communication between the inlet 118 of conduit 116 and interior 94 of the cartridge is inhibited when the valve 108 is in its closed position. As seen in FIG. 1, the valve and lever 111 thereof extend substantially parallel to the body 96 of the cartridge 90 when the valve is in its fully closed position in this example.

Referring to FIG. 10, in order to insert the cartridge 90 into the cartridge-accepting receptacle 70 of the applicator 42, protrusion 104 of the cartridge 90 is first engaged with the catch 80 of the retaining member 76.

Figure 11:
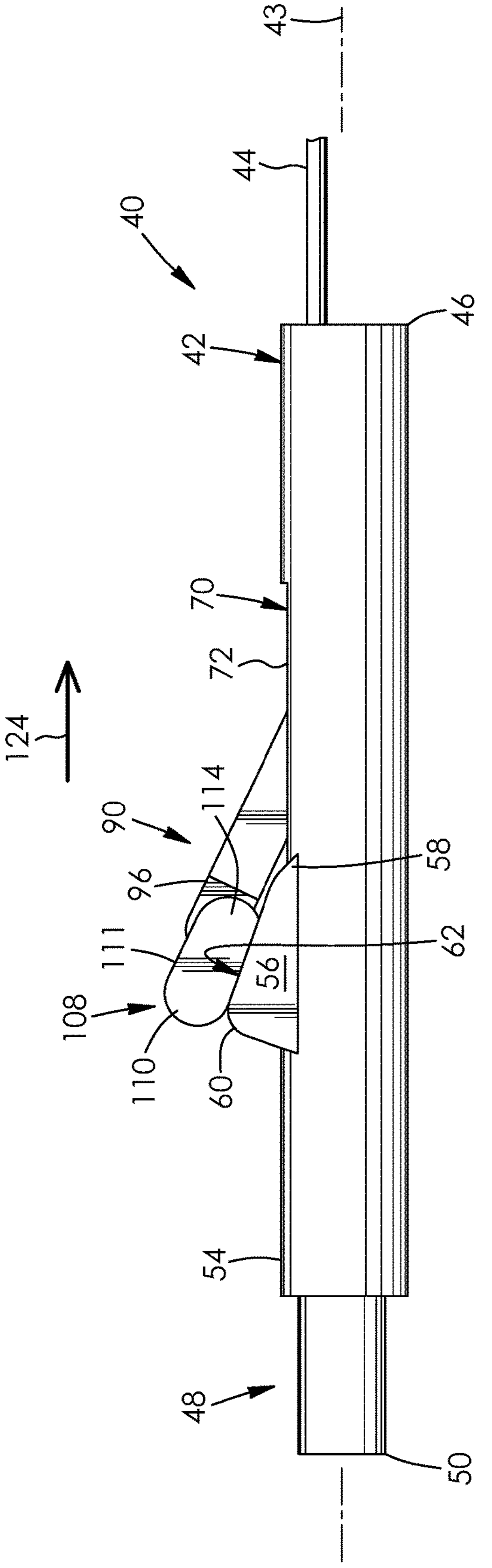
FIG. 11 is a side elevation view of the medicament injector of FIG. 1, with the cartridge shown further inserted into the cartridge-accepting receptacle of the applicator, and with the valve actuator shown abutting an upper part of a ramp of the applicator.

As seen in FIG. 11, the lever 111 next abuts against and is slid along the recessed track 62 of the ramp 56 of the applicator. The cartridge 90 is next moved to the right, from the perspective of FIG. 11 as shown by arrow of numeral 124, so as to cause the valve 108 to slide down the ramp towards the cartridge-accepting receptacle 70. At the same time, this movement of the cartridge to the right causes the retaining member 76 to move from its extended position seen in FIG. 12 towards its retracted position seen in FIG. 19. This thereby provides space for the cartridge 90 to be inserted into the cartridge-accepting receptacle 70.

Figure 14:
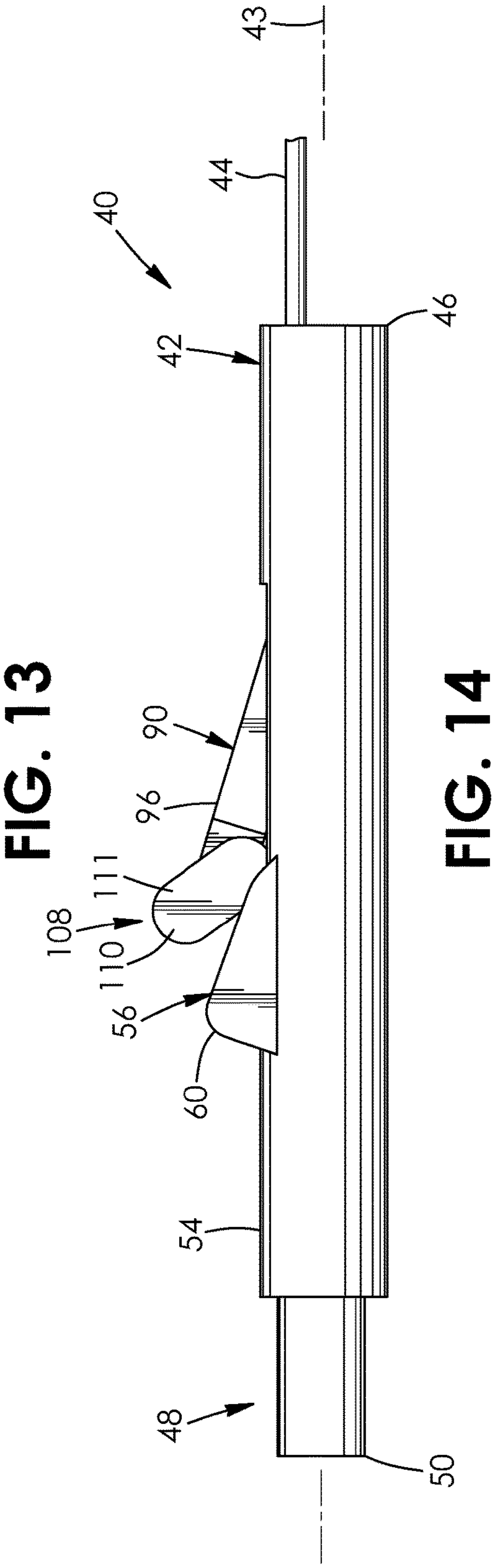
FIG. 14 is a side perspective view of the medicament injector of FIG. 1, with the cartridge shown still further inserted into the cartridge-accepting receptacle compared to FIG. 13, with the valve actuator beginning to enter the cartridge-accepting receptacle and with the ramp of the applicator actuating the valve actuator so as to cause the valve to move from the closed position towards the open position thereof.

Referring to FIGS. 1, 14, and 16, the ramp 56 functions to move the lever 111 from its closed position seen in FIG. 1, to an open position seen in FIG. 16. As seen in FIG. 17, when the valve is in its open position, inlet 118 of conduit 116 is in communication with the interior 94 of the cartridge 90 and outlet 120 of the conduit is in communication with the conduit 53 of the applicator 42. Fluid communication between the medicament 92 and the medicament-output end 110 of the cartridge is promoted thereby. The lever 111 in its fully open position also enables detents 57 of the applicator to align with recess of the valve body 114 and couple to the valve body thereby. Thus, insertion of the cartridge 90 into the applicator 42 causes the valve 108 to rotate from its closed position seen in FIG. 1 to its open position seen in FIG. 16, and enables the medicament 92 seen in FIG. 17 to be accessible by the applicator 42. Insertion of the cartridge into the cartridge-accepting receptacle 70 causes the cartridge to move from the pre-injection mode seen in FIG. 1, to an injection mode in which the medicament is accessible via the needle 52 seen in FIG. 19.

Referring to FIG. 17, insertion of the cartridge 90 into the cartridge-accepting receptacle thus causes: the plunger-input end 100 of the cartridge 90 to be in fluid communication with the plunger, with said end abutting a corresponding tapered portion 126 of the applicator 42. Insertion of the cartridge into the cartridge-accepting receptacle further causes the interior 94 of the cartridge to be in fluid communication with the medicament-output end 110 of the cartridge. Insertion of the cartridge 90 into the cartridge-accepting receptacle 70 also causes the medicament-output end of the cartridge to be in fluid communication with the conduit 53 of the applicator 42.

Referring to FIG. 18, spring 84 biases the retaining member 76 towards the cartridge 90 so fully inserted so as to inhibit removal of the cartridge from the cartridge-accepting receptacle. The retaining member is thus shaped to also inhibit removable of the cartridge so fully inserted within the cartridge-accepting receptacle 70.

Referring to FIG. 16, removing the cartridge 90 from the cartridge-accepting receptacle 70 by, for example, pushing rearwards on the lever 111 as seen by arrow of numeral 91, causes the valve 108 to move from its open position to its closed position seen in FIG. 1 once more.

FIGS. 20 to 37 shows a medicament injector 40.1 according to a second aspect. Like parts have like numbers and function as the embodiment shown in FIGS. 1 to 19 with the addition of ".1". Medicament injector 40.1 is similar to medicament injector 40 as shown in FIGS. 1 to 19 with the following exceptions.

Figure 20:
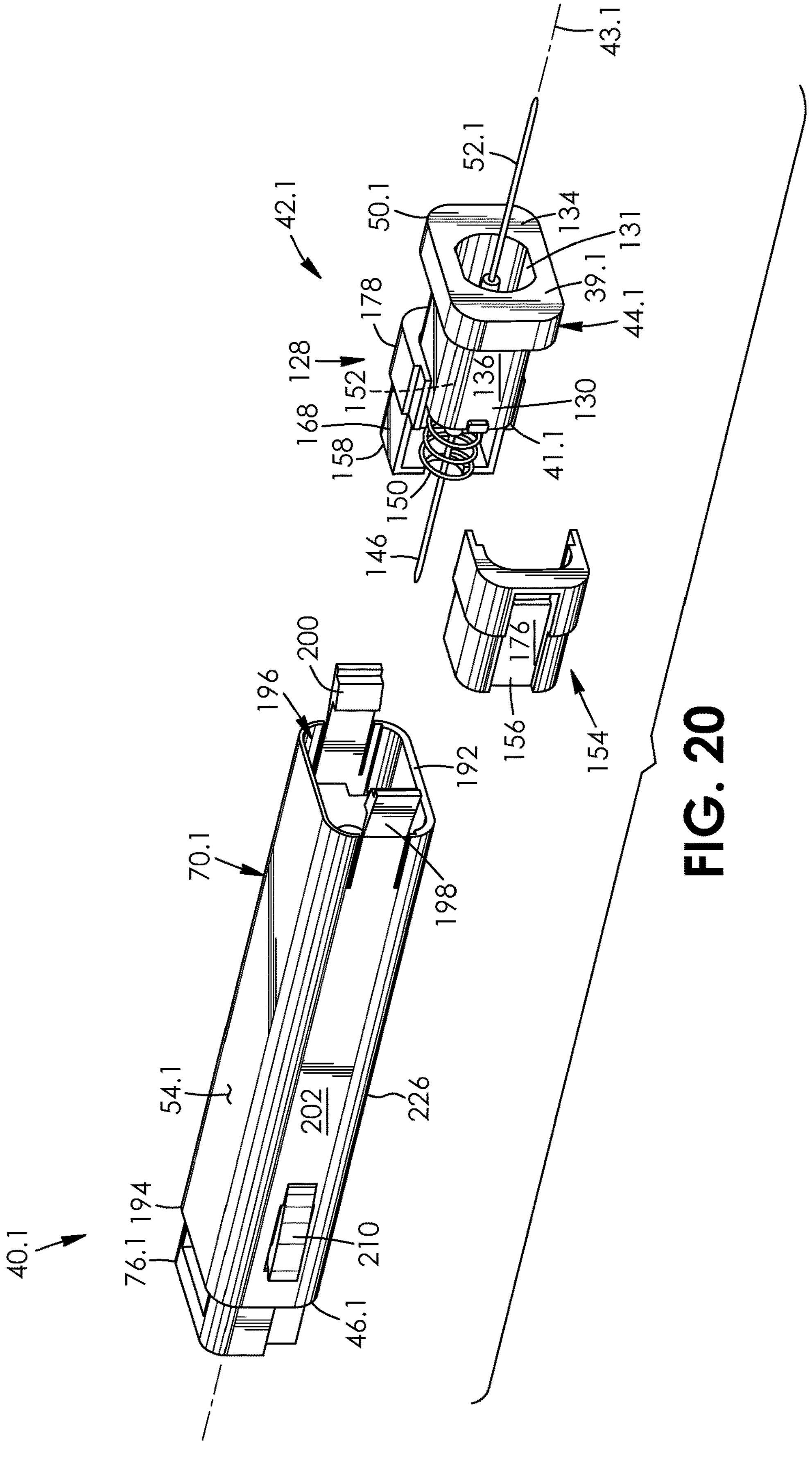
FIG. 20 is a top, front, right side exploded view of a medicament injector according to a second embodiment.
Figure 21A:
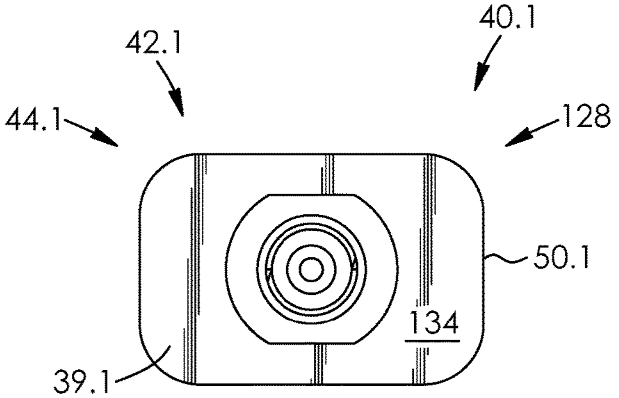
FIG. 21A is a front elevation view of a depressor of the medicament injector of FIG. 20.
Figure 21B:
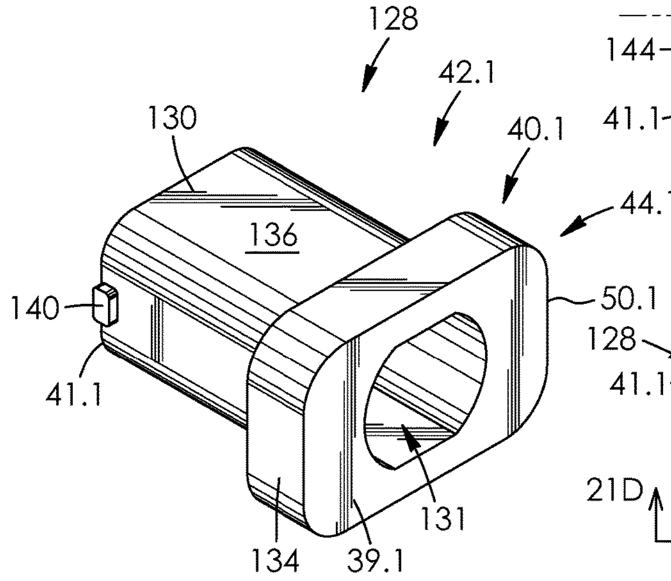
FIG. 21B is a top, front, right side view of the depressor of FIG. 20.
Figure 21C:
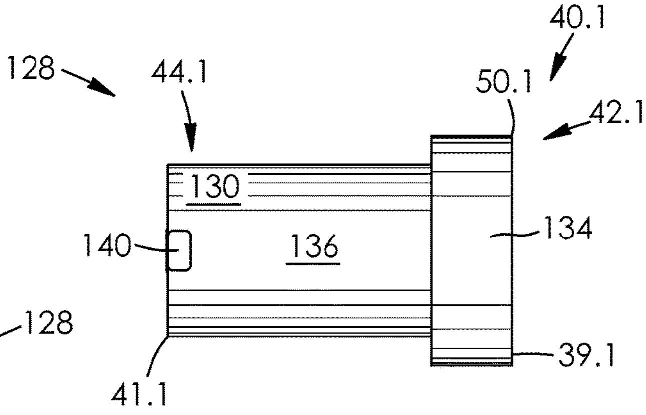
FIG. 21C is a right side elevation view of the depressor of FIG. 20.
Figure 21D:
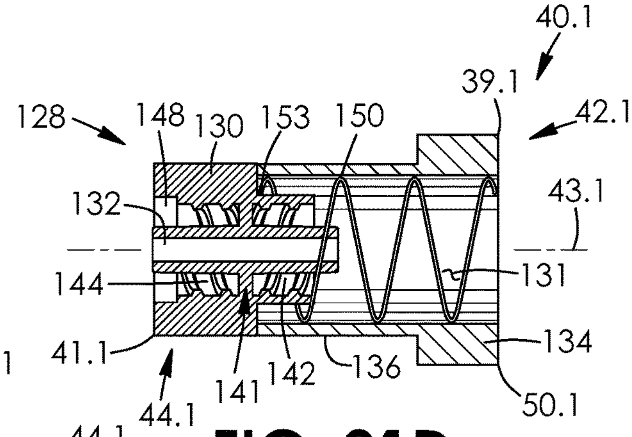
FIG. 21D is a sectional view taken along lines 21D-21D of the depressor of FIG. 21E.
Figure 21E:
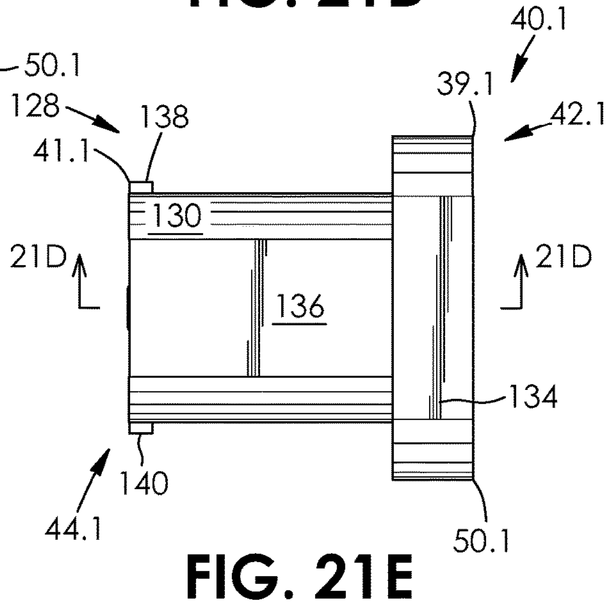
FIG. 21E is a top plan view of the depressor of FIG. 20.

As seen in FIG. 20, applicator 42.1 includes a needle assembly 128. The needle assembly may be referred to in part as a patient-facing portion of the applicator adapted for variable delivery mechanisms including at least one of IM (intramuscular) needle delivery, IV (intravenous) fluid connection delivery with a standard IV tubing and Luer Lock™ mechanism, and IN (intranasal) medicament atomizer delivery. The needle assembly 128 includes a depressor 44.1 which extends from the end 50.1 of the applicator towards 46.1 of the applicator. The depressor may be referred to as a plunger mechanism or a pneumatic delivery system. As seen in FIG. 21D, the depressor has a base 130 which extends from end 41.1 thereof towards end 39.1 thereof. The depressor has a bore 131 which extends from end 41.1 thereof towards end 39.1 thereof and the base thereof. A inner/second bore or passageway 132 extends through the base parallel with axis 43.1 in this example and is in fluid communication with bore 131. The passageway 132 extends from end 41.1 of the depressor towards end 39.1 of the depressor. The depressor 44.1 includes an enlarged flange 134 at end 39.1 thereof. The flange is a rectangular prism in outer shape in this example and is shaped to abut a patient's skin (not shown). The depressor includes a sleeve portion 136 which extends between and couples together the base 130 thereof and the flange thereof. The sleeve portion is rectangular in cross-section in this example, though this is not strictly required. The flange 134 extends radially outwards relative to the sleeve portion 136 and base 130. As seen in FIG. 21E, the depressor 44.1 includes at least one guide member, in this example a pair of spaced-apart protrusions 138 and 140 coupled to and extending outwards from the base of the depressor adjacent to end 41.1 of the depressor.

As seen in FIG. 21D, the depressor includes a hub 141 comprising a pair of mounts, in this example a pair of opposed male Luer-Lock™ fittings 142 and 144 positioned on either side of passageway 132. Luer-lock fittings, including their various parts and functions, are known per se by one skilled in the art and thus will not be described in further detail. Luer-Lock™ fittings 142 and 144 are shaped to selectively coupled with a first or outer needle 52.1 seen in FIG. 20 via a female Luer-lock™ fitting (not shown) and a second or inner needle 146 via a female Luer-lock™ fitting (not shown) in a conventional manner. The needles are in fluid communication with each other via passageway 132 seen in FIG. 21D. As seen in FIG. 20, the inner and outer needles thus couples to the depressor, with the outer needle 52.1 extending outwards from end 39.1 of the depressor and the inner needle 146 extending outwards from end 41.1 of the depressor.

Still referring to FIG. 20, sleeve portion 136 encloses outer needle 52.1 at least in part and the needle assembly 128 is thus received at least in part within the depressor 44.1. Referring back to FIG. 21D, the depressor 44.1 further includes an annular recess 148 adjacent to Luer-lock fitting 144. As seen in FIG. 20, the applicator includes a first resilient member, in this example a coil spring 150 with a first end 152 thereof which fits within recess 148 seen in FIG. 21D. The coil spring has a second end 153 spaced-apart from the first end thereof. The recess is annular in this example and extends from end 41.1 of the depressor 44.2 towards end 39.1 of the depressor.

Figures 22A, 22B, 22C, 22D, 22E, 22F, 22G:
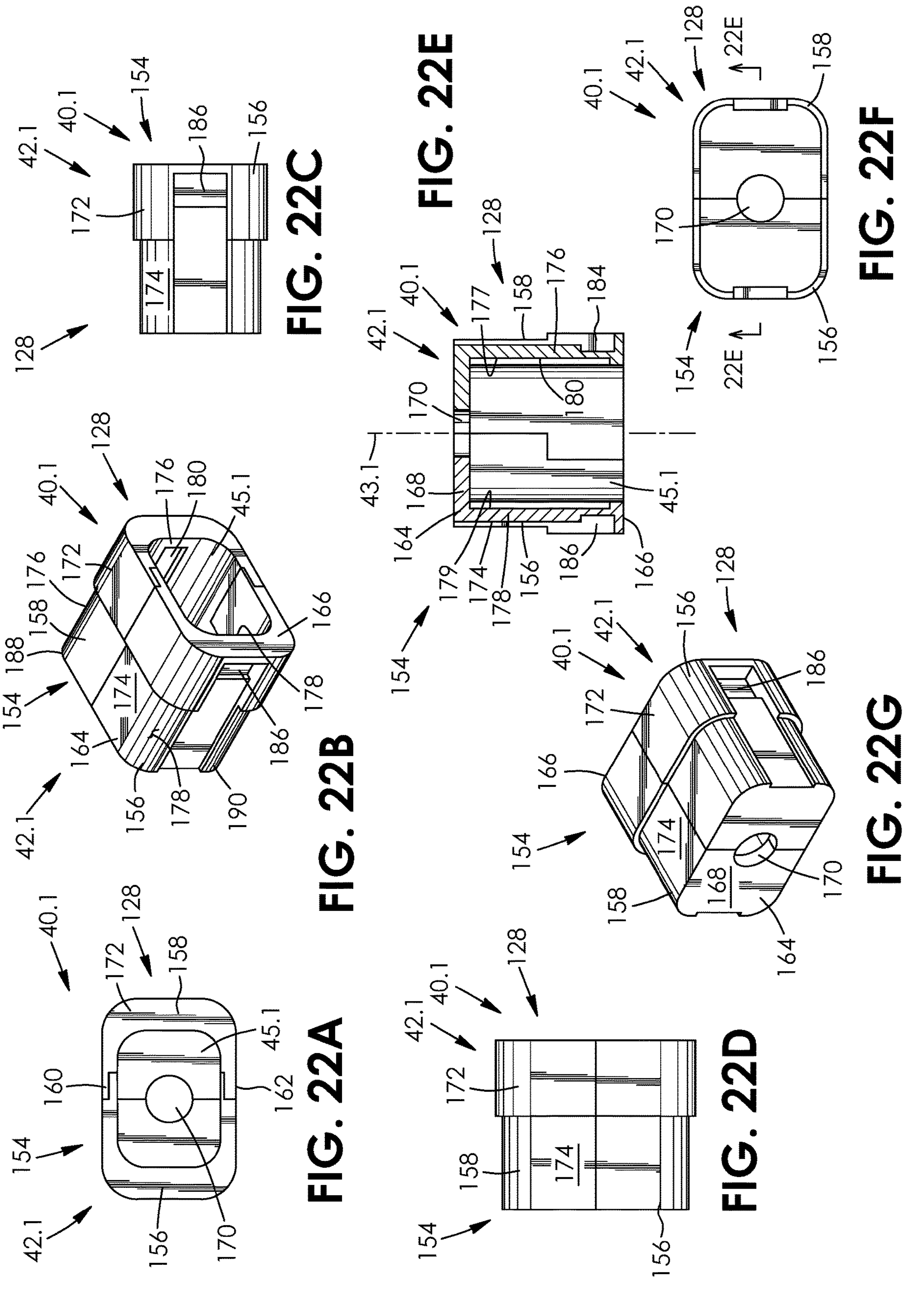
FIG. 22A is a front elevation view of a depressor housing of the medicament injector of FIG. 20.
FIG. 22B is a top, front, right side view of the depressor housing of FIG. 20.
FIG. 22C is a right side elevation view of the depressor housing of FIG. 20.
FIG. 22D is a top plan view of the depressor of FIG. 20.
FIG. 22E is a sectional view taken along lines 22E-22E of the depressor of FIG. 22F.
FIG. 22F is a rear elevation view of a depressor housing of the medicament injector of FIG. 20.
FIG. 22G is a top, rear, right side elevation view of the depressor housing of the medicament injector of FIG. 20.

As seen in FIG. 20, the applicator 42.1 includes a depressor housing 154 comprises of two parts 156 and 158. The parts couple together via complementary snap fittings 160 and 162 seen in FIG. 22A. As seen in FIG. 22E, the depressor housing has a closed or inner end 164 and an open, outer end 166. The depressor housing 154 has a base 168 which extends from end 164 thereof towards end 166 thereof. As seen in FIG. 22E, a passageway 170 extends through the base parallel with axis 43.1 in this example. The depressor housing 154 includes an enlarged flange 172 at end 166 thereof. The flange is a rectangular prism in outer shape in this example. The depressor housing includes a sleeve portion 174 which extends between and couples together the base 168 thereof and the flange thereof. The sleeve portion is generally rectangular in cross-section in this example, though this is not strictly required. The flange 172 extends radially outwards relative to the sleeve portion 174 and base 168.

As seen in FIG. 22B, the depressor housing 154 has a bore 45.1 and the sleeve portion 174 includes a pair of spaced-apart walls 176 and 178 with inner surfaces 177 and 179 which face each other and which are in fluid communication with the bore. As seen in FIG. 22E, the depressor housing includes a pair of inner guides, in this example guide channels 180 and 182. The bore 45.1 is shaped to receive the base 130 and sleeve portion 136 of the depressor 44.1 seen in FIG. 21E, with the protrusions 138 and 140 of the depressor being received within and slidable along the guide channels 180 seen in FIG. 22B. Spring 150 seen in FIG. 20 is positioned between base 130 of depressor 44.1 and base 168 of the depressor so as to bias the depressor axially outwards relative to the depressor housing to extend about needle 52.1 in a protected needle mode. As seen in FIG. 21D, end 153 of the spring abuts the base of the depressor.

Figure 24:
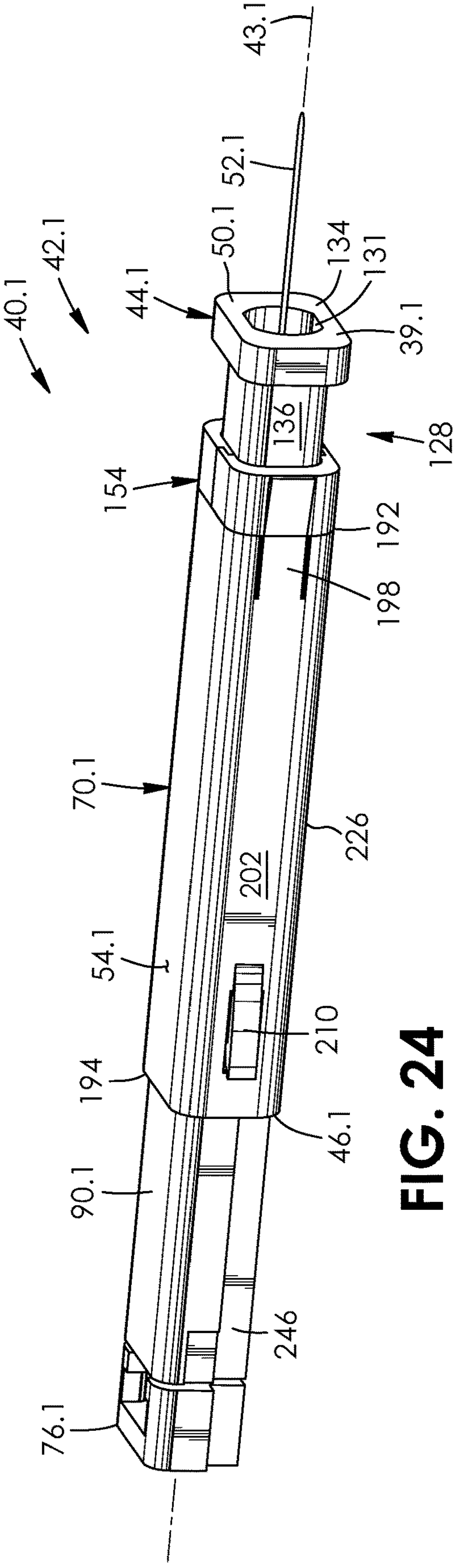
FIG. 24 is a top, front, right side exploded view of the medicament injector of FIG. 23, with the depressor housing shown coupled to the cartridge-accepting receptacle and the medicament injector further including an interchangeable cartridge shown in the process of being removed from the cartridge-accepting receptacle.

As seen in FIG. 24, the needle assembly 128 is thus coupled to and resiliently biased outwards from cartridge-accepting receptacle 70.1.

Figure 35:
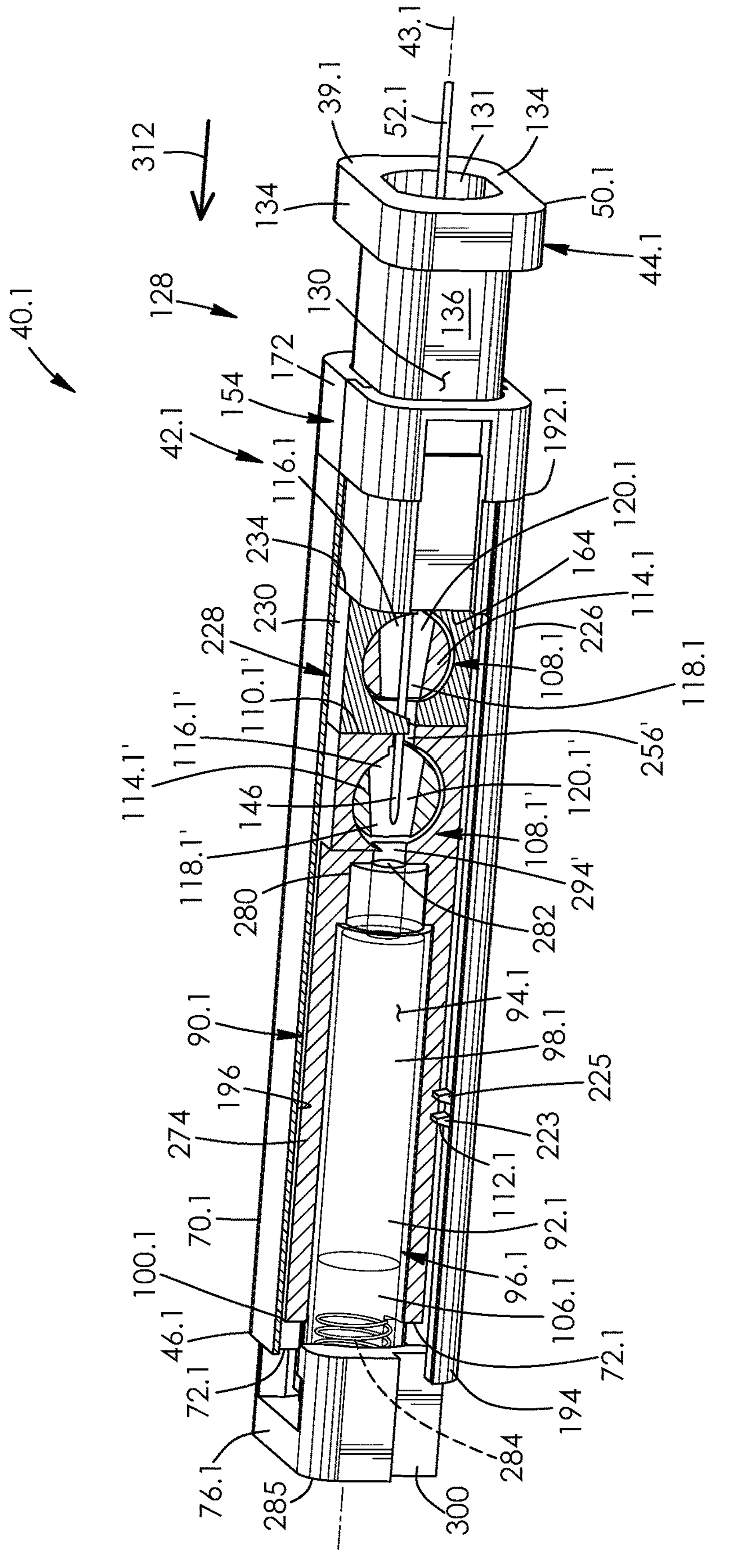
FIG. 35 is a side elevation view of the medicament injector of FIG. 20, with the cartridge fully inserted into the cartridge-accepting receptacle, the medicament injector including a needle assembly coupled to the depressor, and the depressor being shown in pre-injection mode with the needle assembly spaced forward of the barrel containing medicament.
Figure 36:
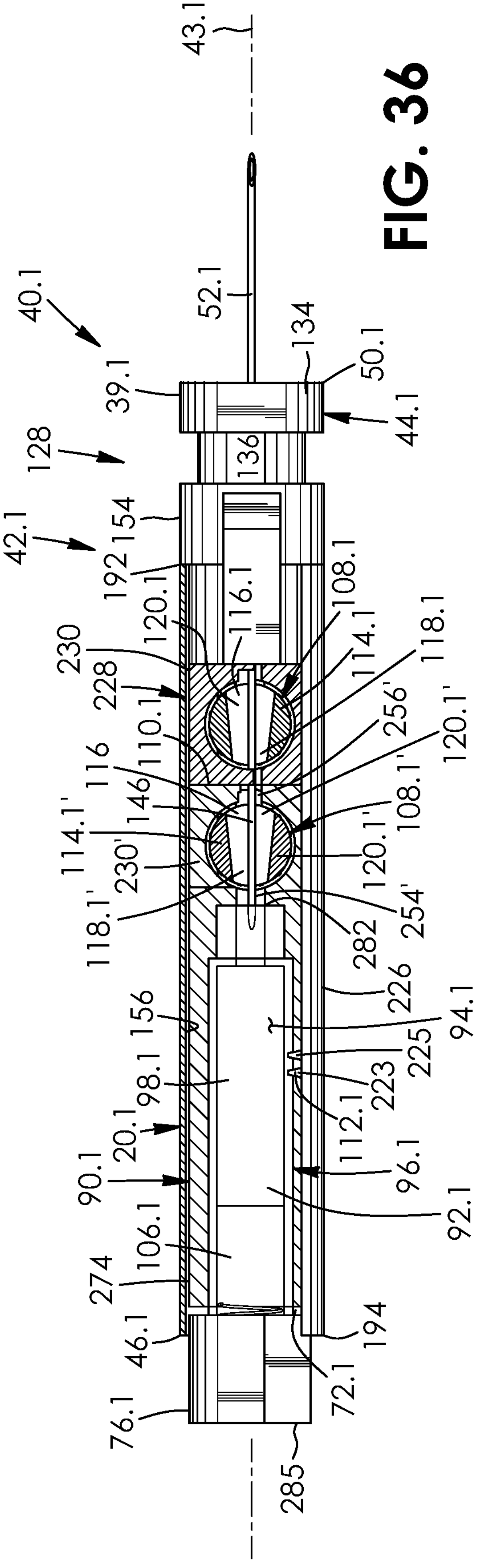
FIG. 36 is a side elevation view of the medicament injector of FIG. 35, with the depressor partially depressed towards the cartridge-accepting receptacle and shown in an injection mode, with the needle assembly piercing through into the barrel and being in fluid communication with the medicament.
Figure 37:
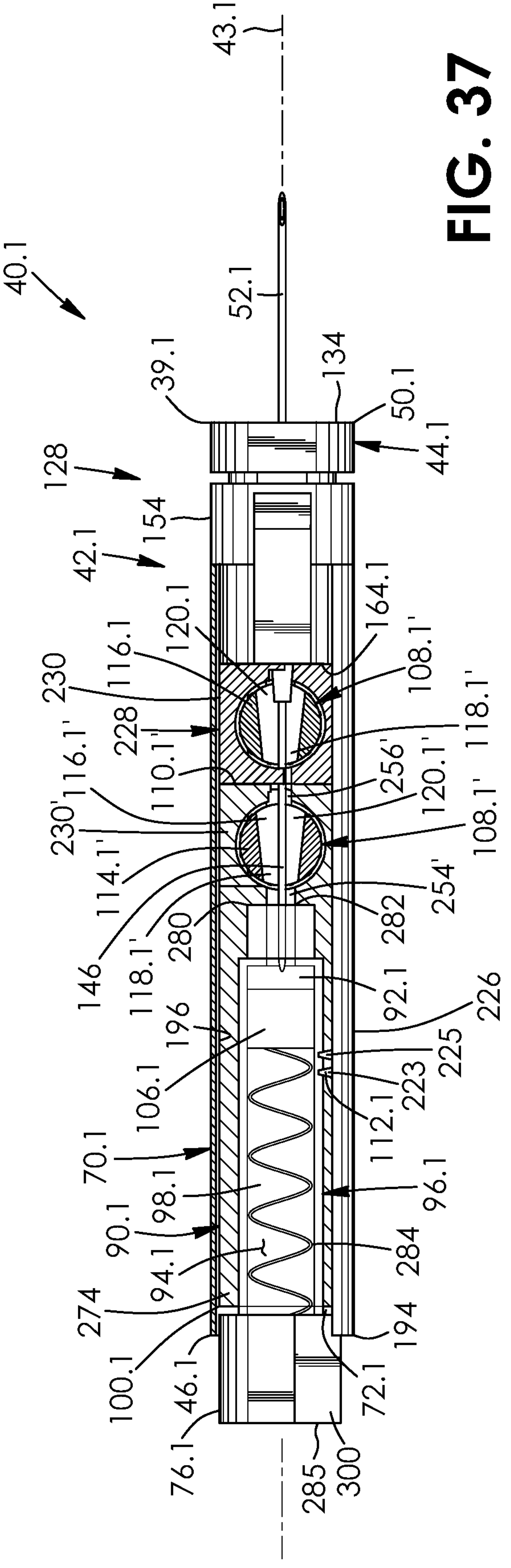
FIG. 37 is a side elevation view of the medicament injector of FIG. 36, with the depressor fully depressed towards the cartridge-accepting receptacle and shown in said injection mode, with the needle assembly more fully extending into the barrel and being in fluid communication with the medicament.

The depressor has a pre-injection position/mode or needle protected mode seen in FIG. 35 in which flange 134 of the depressor is space-apart from flange 172 of the depressor housing 154. The depressor 44.1 is linearly movable or retractable via the protrusions 138 and 140 seen in FIG. 21E and guide channels 180 and 182 seen in FIG. 22E, from the pre-injection position of FIG. 35 to an injection position seen in FIG. 37 to deploy needle 52.1. As seen in FIGS. 37, flanges 134 and 172 abut each other in the injection position.

Referring back to FIG. 22E, the depressor housing 154 includes a pair of spaced-apart outer female locking members, in this example recessed portions 184 and 186 which extend inwards from outer surfaces 188 and 190 of walls.

As seen in FIG. 20, the applicator 42.1 includes a cartridge-accepting receptacle 70.1 that is tubular in this example and generally rectangular in cross-section in this case. The cartridge-accepting receptacle has a first or distal open end 192 and a second or proximal open end 194, which coincides with end 46.1 of the applicator. The cartridge-accepting receptacle 70.1 includes a bore 196 which extends from the first to the second end thereof. Depressor 44.1 extends outwards from distal open end 192 of the cartridge-accepting receptacle 70.1.

Figure 23:
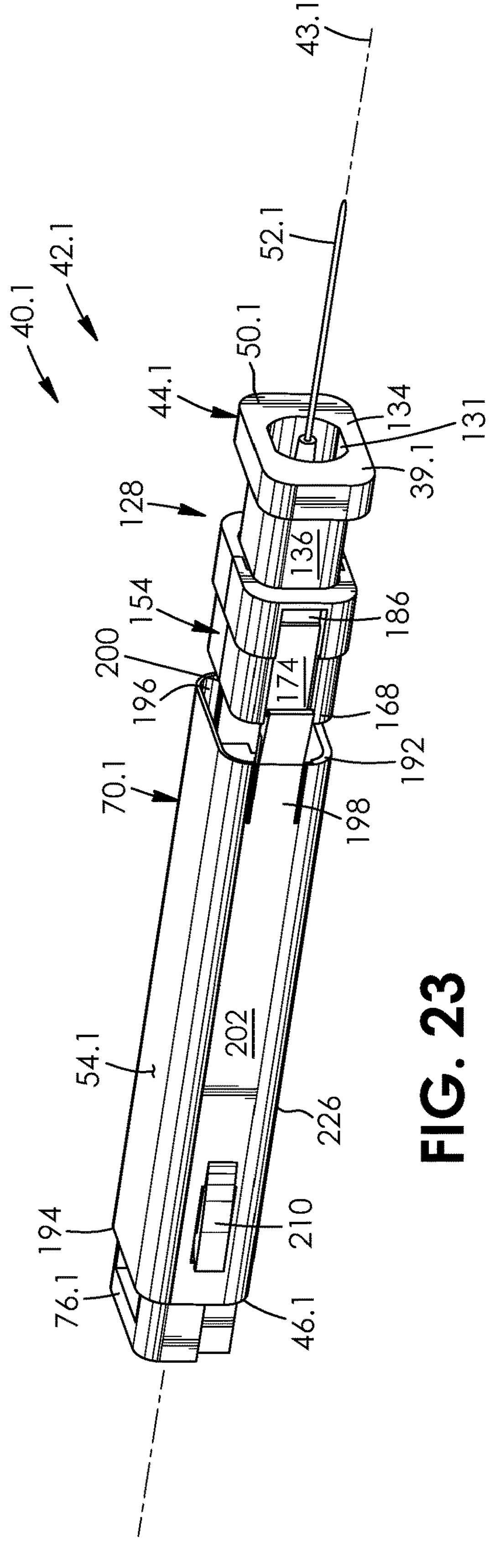
FIG. 23 is a top, front, right side exploded view of the medicament injector of FIG. 20, with the depressor housing shown fully assembled and extending about the depressor, and the depressor housing shown in the process of coupling to a cartridge-accepting receptacle.
Figure 25C:
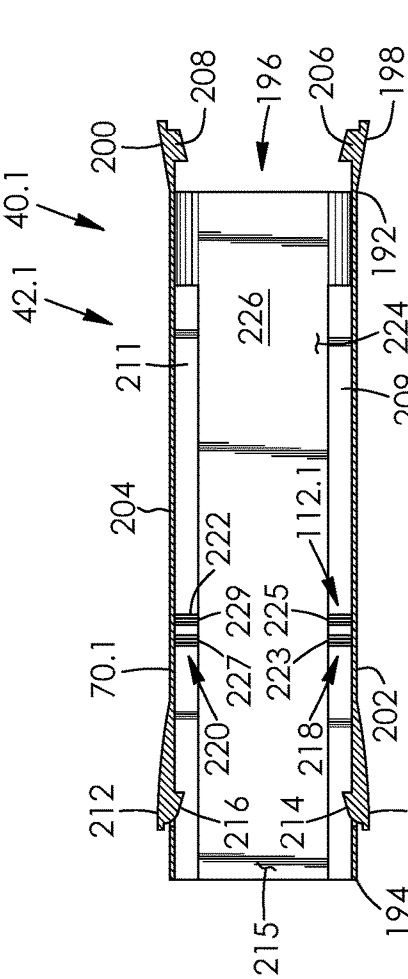
FIG. 25C is a sectional view taken along lines 25C-25C of the cartridge-accepting receptacle of FIG. 25D.
Figure 25D:
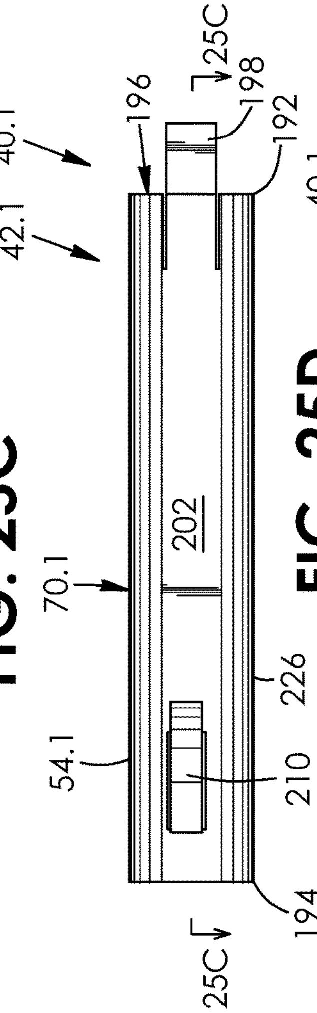
FIG. 25D is a right side elevation view of the cartridge-accepting receptacle of FIG. 23.
Figure 25E:
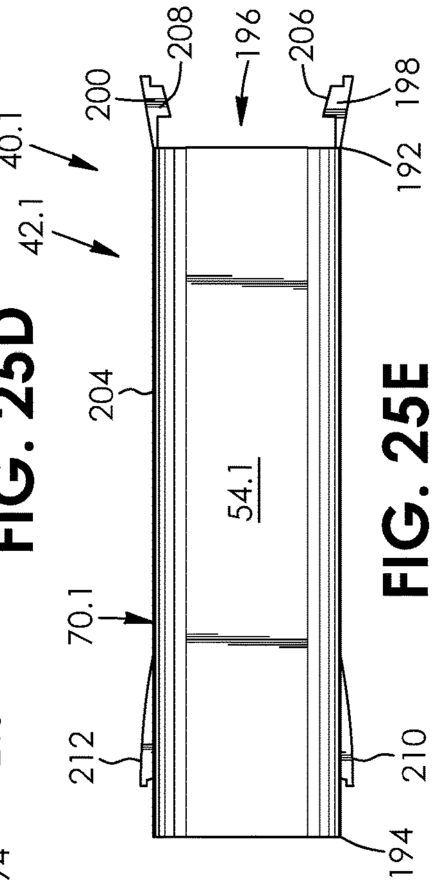
FIG. 25E is a top plan view of the cartridge-accepting receptacle of FIG. 23.

As seen with reference to FIGS. 23 and 24, bore 196 is shaped to receive base 168 and sleeve portion 174 of depressor housing 154 such that end 192 of the cartridge-accepting receptacle 70.1 abuts flange 186 of the depressor housing. Referring to FIG. 25B, the cartridge-accepting receptacle selectively couples to the depressor housing, in this example via a first pair of spaced-apart, resilient catch members 198 and 200 which couple to and extend outwards from opposed first and second walls 202 and 204 of the cartridge-accepting receptacle. As seen in FIG. 25C, the catch members include protuberances 206 and 208 shaped to fit within recessed portions 184 of depressor housing 154 as seen with reference to FIGS. 23 and 24.

Figure 25A:
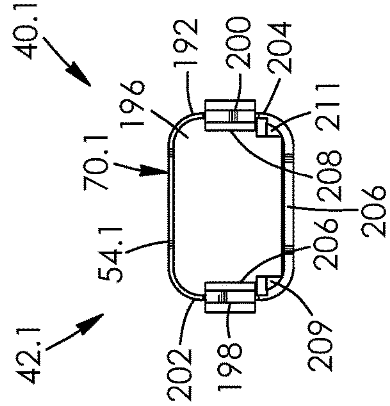
FIG. 25A is a front elevation view of the cartridge-accepting receptacle of FIG. 23.
Figure 25B:
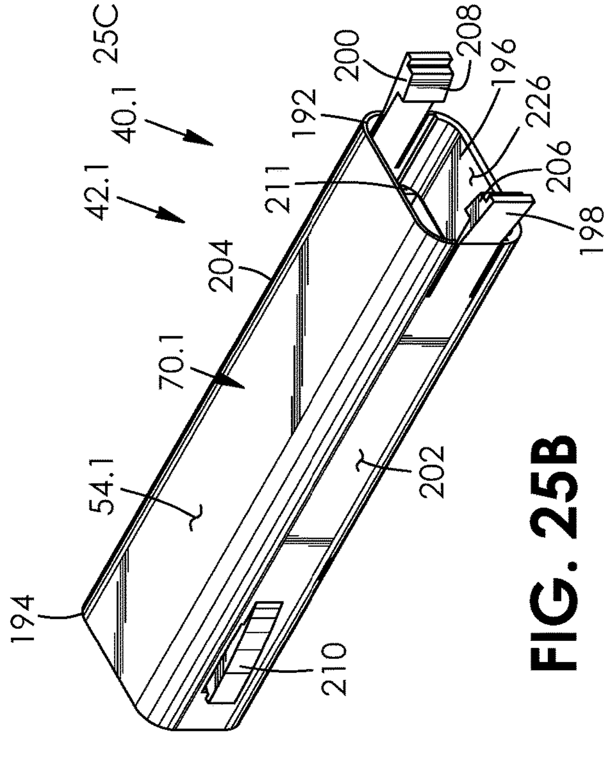
FIG. 25B is a top, front, right side view of the cartridge-accepting receptacle of FIG. 23.

As seen in FIG. 25A, the cartridge-accepting receptacle 70.1 includes a pair of guides, in this example spaced-apart longitudinally-extending protrusions 209 and 211. Referring to FIG. 25C, the cartridge-accepting receptacle includes of a third wall 226 to which the protrusions couple and along which the protrusions extend. The third wall is coupled to and extends between walls 202 and 204. The protrusions 209 and 211 extend from near end 192 of the cartridge-accepting receptacle to end 194 of the cartridge-accepting receptacle. The protrusions 209 and 211 are rectangular prisms in shape in this example. As seen in FIG. 25A, the cartridge-accepting receptacle 70.1 includes a fourth wall 54.1 opposite to wall 226. Each of the walls 202, 204, 226 and 54.1 of the cartridge-accepting receptacle is planar in this example.

As seen in FIG. 25C, the cartridge-accepting receptacle 70.1 includes a second pair of spaced-apart, resilient catch members 210 and 212 spaced from and near end 194 thereof. The catch members includes protuberances 214 and 216 which extend in part within bore 196 and interior 215 of the cartridge-accepting receptacle.

As seen in FIG. 25C, the applicator 42.1 includes a valve actuator, in this example linear gears, in this example in the form of a pair of spaced-apart rows 218 and 220 of linear gears 112.1 and 222, each comprising teeth 223 and 225, and teeth 227 and 229. Linear gears 112.1 are adjacent to wall 202 of the cartridge-accepting receptacle and linear gears 222 are adjacent to wall 204 of the cartridge-accepting receptacle. The linear gears are interposed between ends 192 and 194 of the cartridge-accepting receptacle 70.1 and in this example are positioned adjacent to catch members 210 and 212. Referring to FIG. 25C, the linear gears 112.1 and 222 are in fluid communication with bore 196 and couple to and extend upwards from respective longitudinally-extending protrusions 209 and 211 of the cartridge-accepting receptacle in this example.

Figure 26:
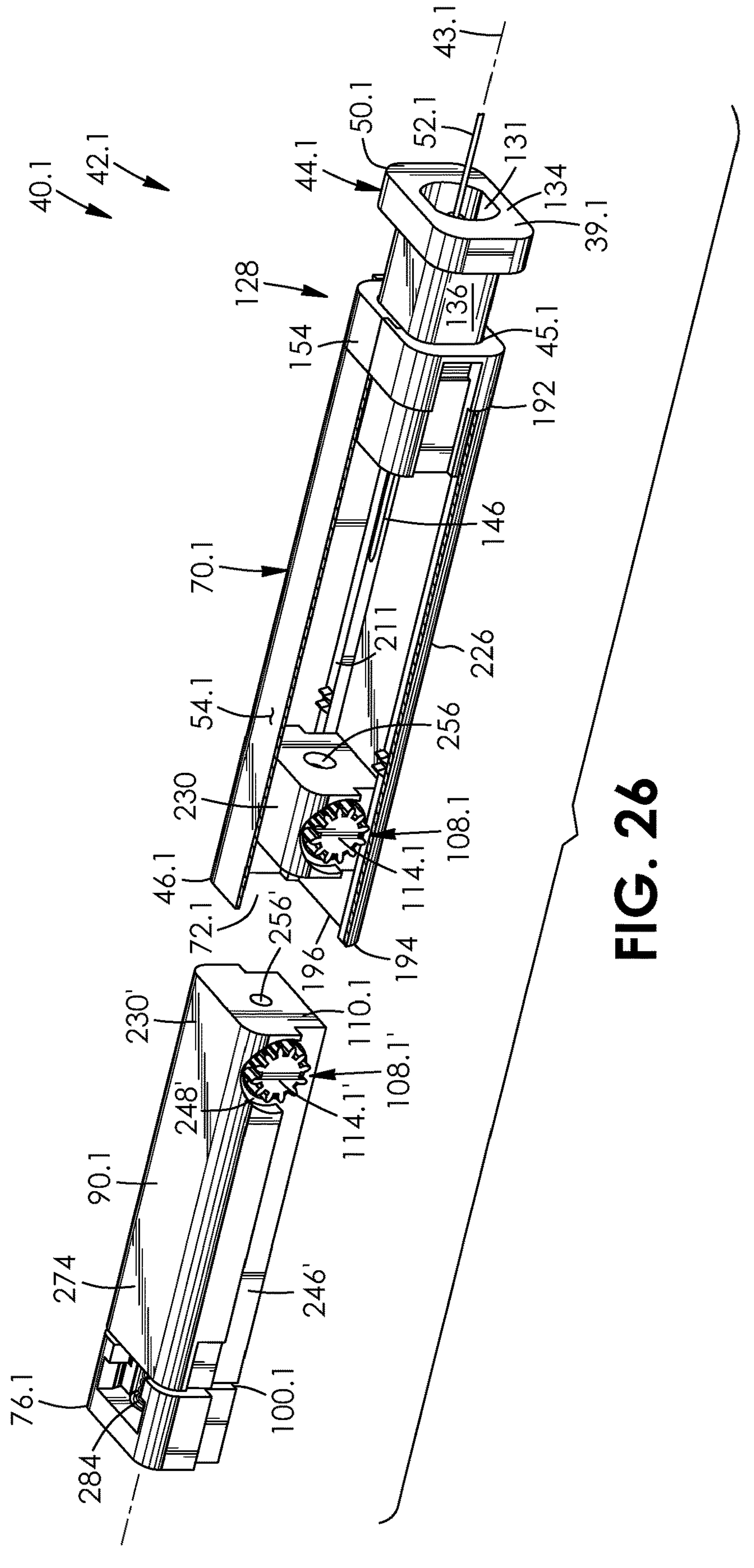
FIG. 26 is a top, front, right side exploded view of the medicament injector of FIG. 23, with the cartridge shown fully removed from the cartridge-accepting receptacle to reveal a first valve thereof and with the cartridge-accepting receptacle shown partially in fragment to reveal interior contents thereof including a second valve thereof, the second valve including a valve housing and a valve body disposed within the valve housing.
Figures 27A, 27B, 27C, 27D, 27E, 27F:
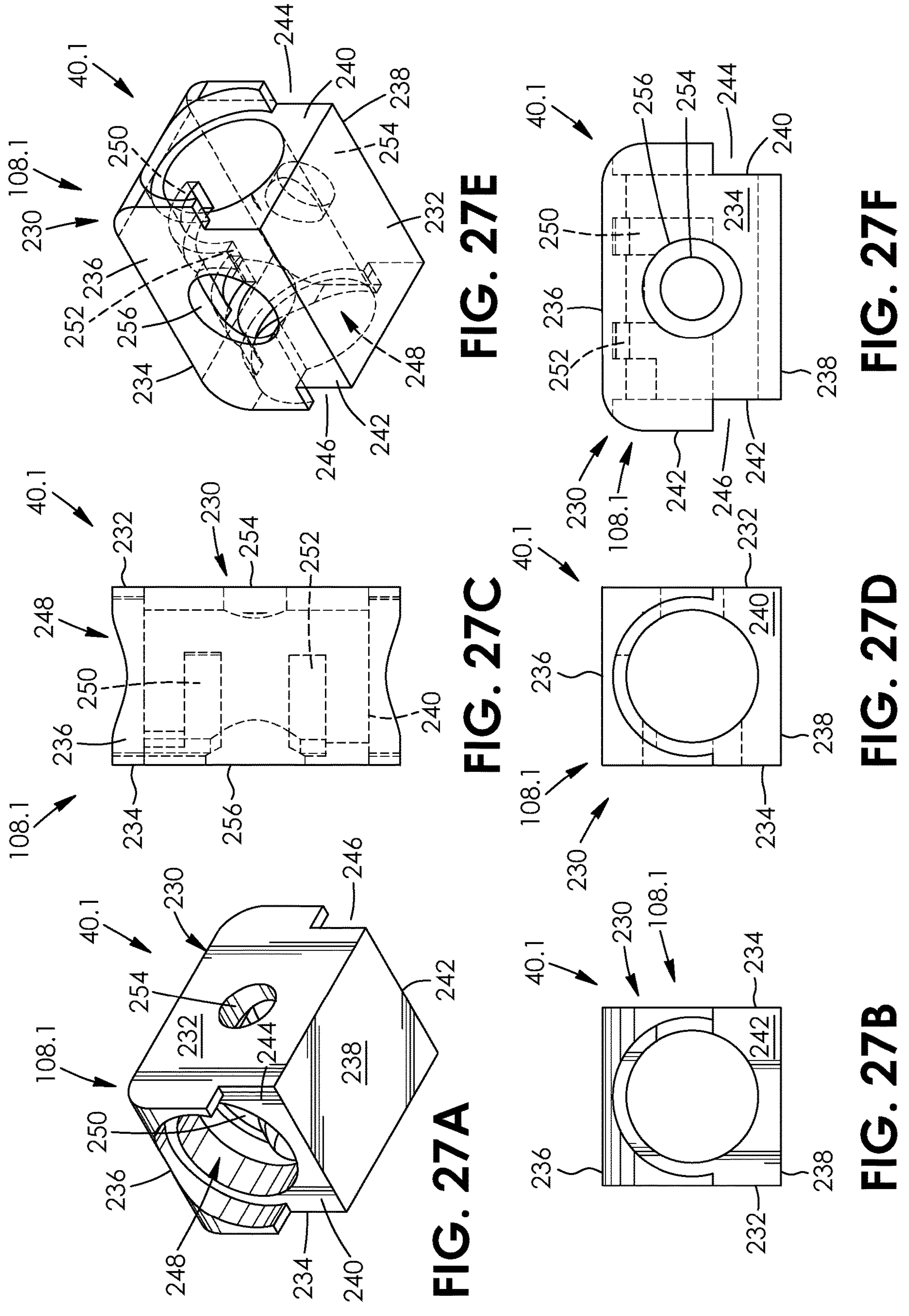
FIG. 27A is a left side, bottom, rear perspective view of the valve housing of the second valve of FIG. 26.
FIG. 27B is a right side elevation view of the valve housing of FIG. 27A.
FIG. 27C is a top plan view of the valve housing of FIG. 27A.
FIG. 27D is a left side elevation view of the valve housing of FIG. 27A.
FIG. 27E is a front, bottom, left side perspective view of the valve housing of FIG. 27A.
FIG. 27F is a front elevation view of the valve housing of FIG. 27A.
Figure 33A:
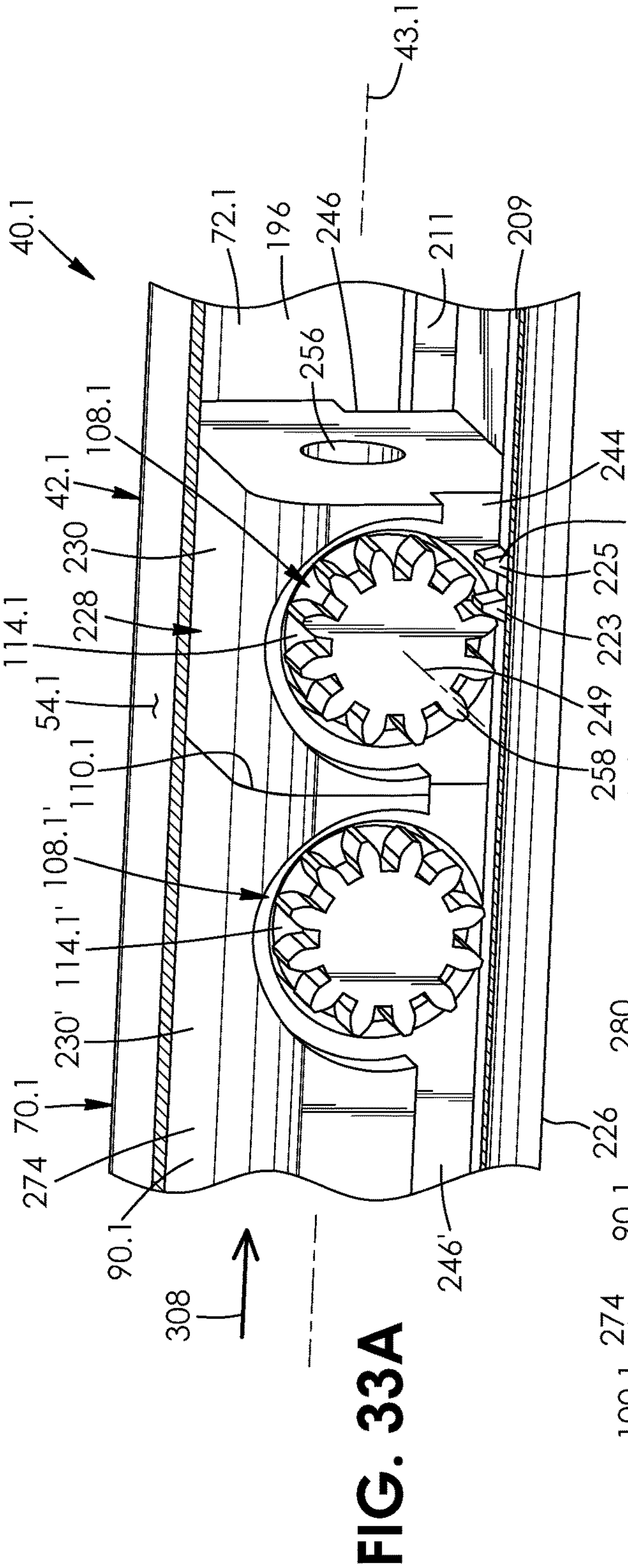
FIG. 33A is an enlarged fragmented view of the cartridge-accepting receptacle showing a linear set of teeth thereon, with the first valve and the second valve shown in closed positions, and each valve having circular gears, with the gears of the second valve in the process of engaging with the teeth of the cartridge to move the second valve from the closed position thereof to an open position thereof.

As seen in FIG. 26, the medicament injector 40.1 includes a first barrier member, in this example a valve 108.1. The valve includes a valve housing 230 best seen in FIGS. 27A to 27F. The valve housing is generally block-like and a rectangular prism in shape in this example. As seen in FIG. 27A, the valve housing a first or rear end 232, a second or front end 234, a top 236, F and a bottom 238 and a pair of sides 240 and 242 which extend between the top and bottom thereof and ends thereof. The valve housing 230 has a pair of spaced-apart lower recessed regions 244 and 246 along sides thereof. As seen in FIG. 33A, the valve housing 230 is shaped to slidably extend within bore 196 of the cartridge-accepting receptacle 70.1 with protrusions 209 and 211 extending within the recessed regions 244 and 246 of the valve housing.

Referring back to FIG. 27A, the valve 108.1 includes a bore 248 which extends through the sides 240 and 242 of the valve housing and which is positioned between the rear end 232 and front end 234 of the valve housing. As seen in FIG. 33A, the bore extends along a lateral axis 249 which is perpendicular to axis 43.1 of the medicament injector 40.1. As seen in FIG. 27E, the valve has at least one, in this example a pair of spaced-apart tracks, in this case recessed channels 250 and 252 positioned between the sides 240 and 242, top 236 and bottom 238, and ends 232 and 234 of the valve housing. The channels are arc-shaped in side profile in this example and in fluid communication with the bore 248. The channels 250 and 252 are rectangular in lateral cross-section in this example.

As seen in FIG. 27A, the valve housing 230 has a first or rear aperture 254 which extends through rear end 232 thereof and which is in fluid communication with bore 248. As seen in FIG. 27E, the valve housing has a second or front aperture 256 which extends through the front end 234 thereof and which is also in fluid communication with the bore. Each of the apertures is circular in this example, with front aperture 256 being larger than rear aperture 254 in this example.

Figure 28A:
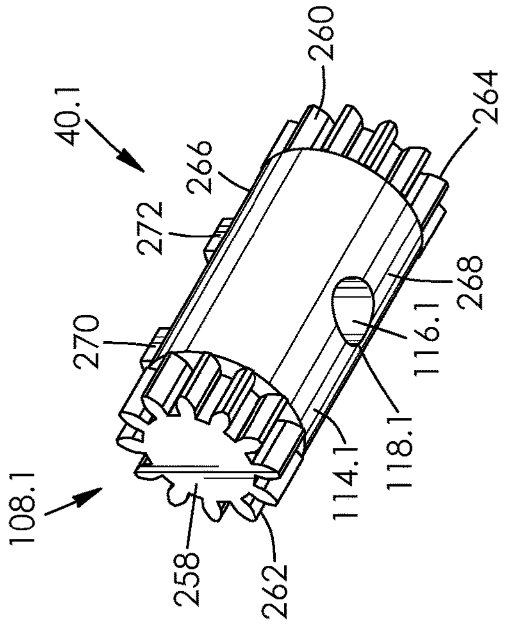
FIG. 28A is a bottom, right side, front perspective view of the valve body of the second valve of FIG. 26.
Figure 28B:
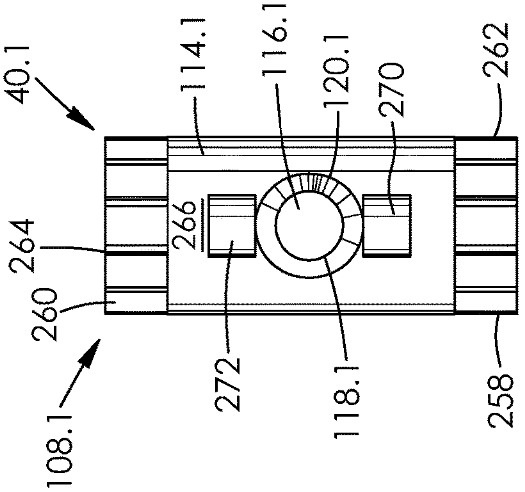
FIG. 28B is a top plan view of the valve body of FIG. 28A.
Figure 28C:
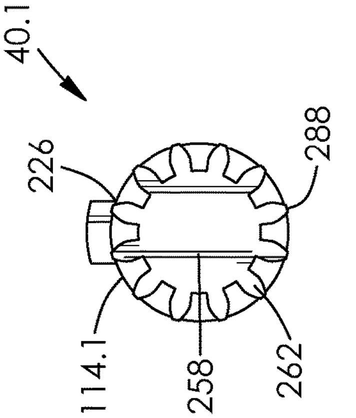
FIG. 28C is a right side elevation view of the valve body of FIG. 28A.
Figure 28D:
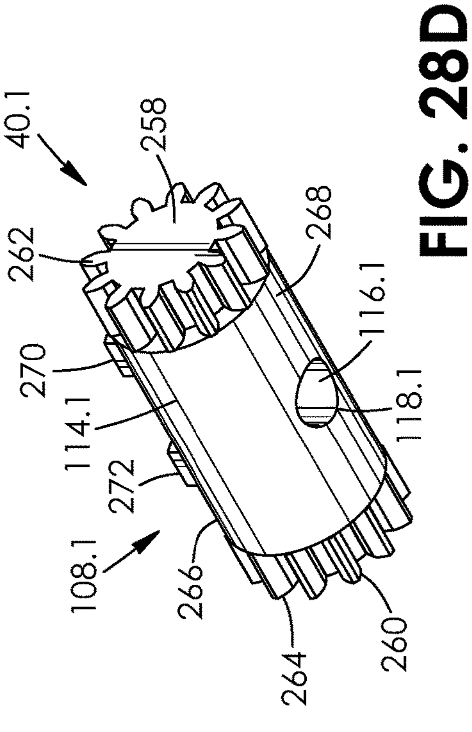
FIG. 28D is a bottom, right side, rear perspective view of the valve body of FIG. 28A.
Figure 28E:
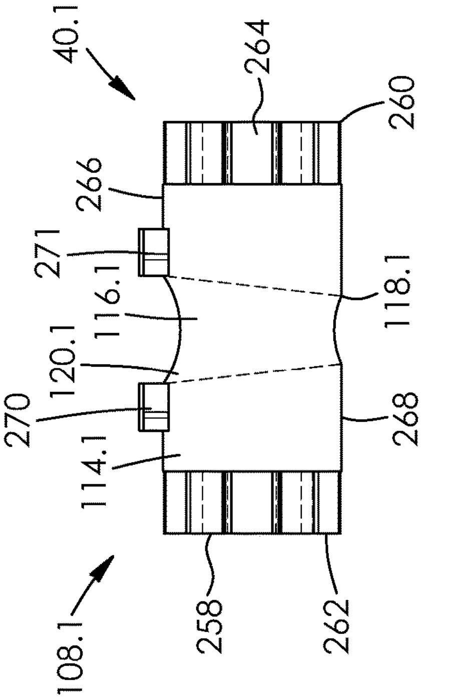
FIG. 28E is a front elevation view of the valve body of FIG. 28A.

As seen in FIGS. 28A to 28E, the valve 108.1 includes a valve body 114.1 which is generally cylindrical in shape in this example. The body includes a pair of circular gears 258 and 260 at spaced-apart ends 262 and 264 thereof. As seen in FIG. 28E, the valve body includes a conduit, in this example a tapered passageway 116.1 that is tapered in this example from outlet 120.1 towards inlet 118.1. The passageway extends from the top 266 to the bottom 268 of the valve body and is positioned between ends 262 and 262 of the valve body. As seen with reference to FIGS. 28B and 28E, the valve body 114.1 includes at least one, and in this example a pair of spaced-apart guides, in this example protrusions 270 and 272 coupled to and extending upwards from the top 266 of the valve body relative to the FIGS. 28B and 28E. Each of the protrusions is generally a rectangular prism in shape in this example. The protrusions are positioned between gears 258 and 260, and adjacent to outlet 120.1 of passageway 116.1 in this example.

Referring to FIGS. 27A and 28A, the valve body 114.1 is shaped to fit within bore 248 of valve housing 230, with protrusions 270 and 272 shaped to fit within and be movable relative to recessed channels 250 and 252 seen in FIG. 27E.

Figure 33B:
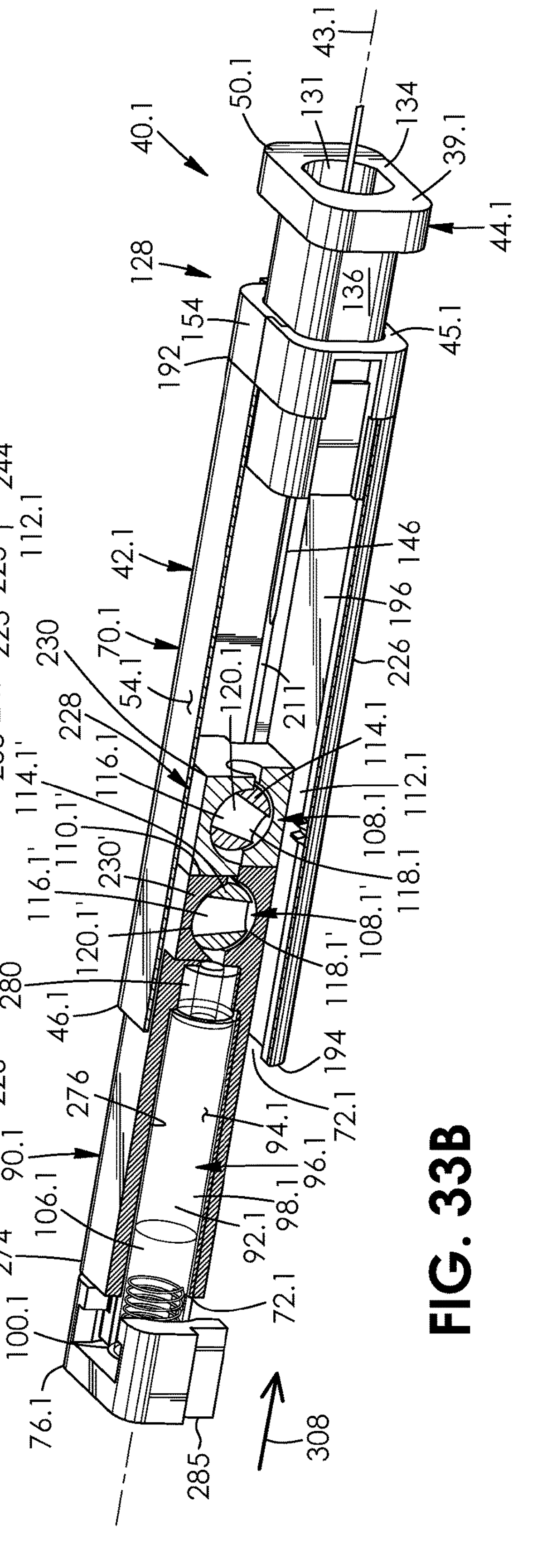
FIG. 33B is an exploded view of the medicament injector in the same position of FIG. 33A, with the cartridge in the processor of being inserted into the cartridge-accepting receptacle and sectional views of the valves being shown in their closed positions.

The valve 108.1 has a closed position seen in FIGS. 28A, 33A and 33B in which passageway 116.1 seen in FIG. 28A is not in fluid communication with apertures 254 and 254 of the valve housing seen in FIG. 27F.

Figure 34A:
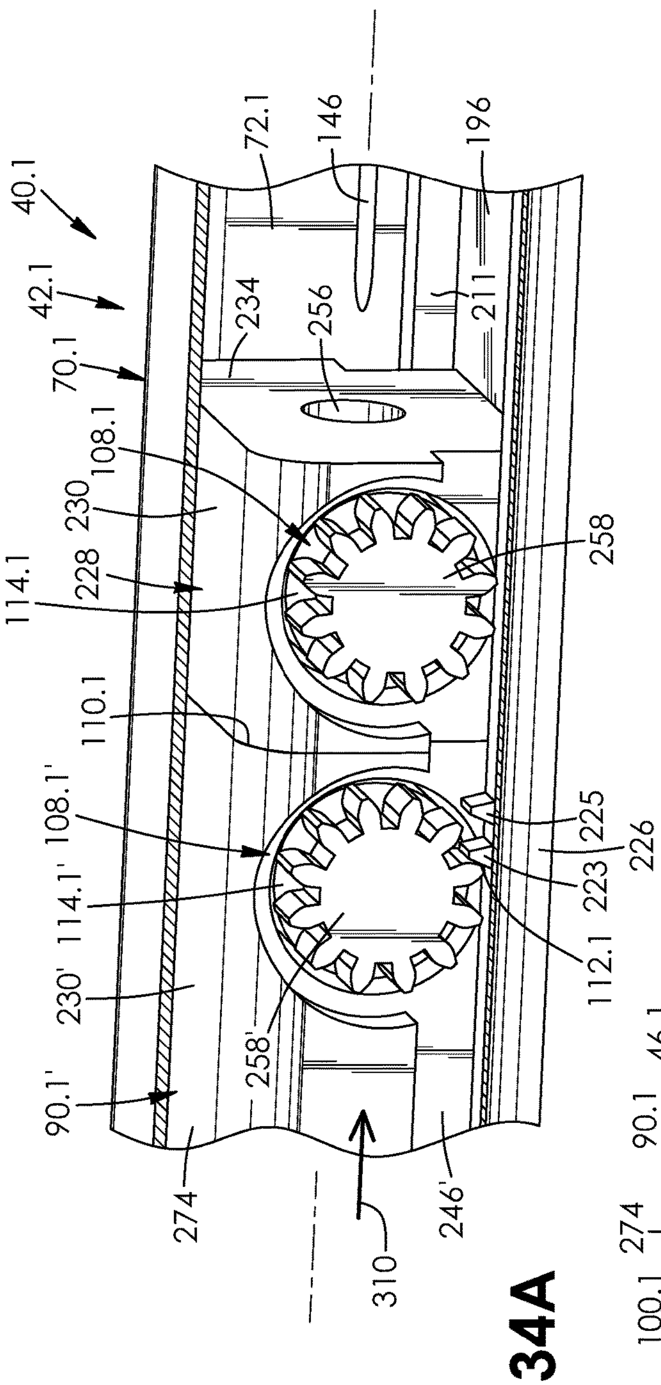
FIG. 34A is an enlarged fragmented view of the cartridge-accepting receptacle, with the teeth positioned between the first valve and the second valve, the second valve now in the closed position, the gears of the first valve in the process of engaging with the teeth the cartridge to move the first valve from the open position thereof to the closed position thereof.
Figure 34B:
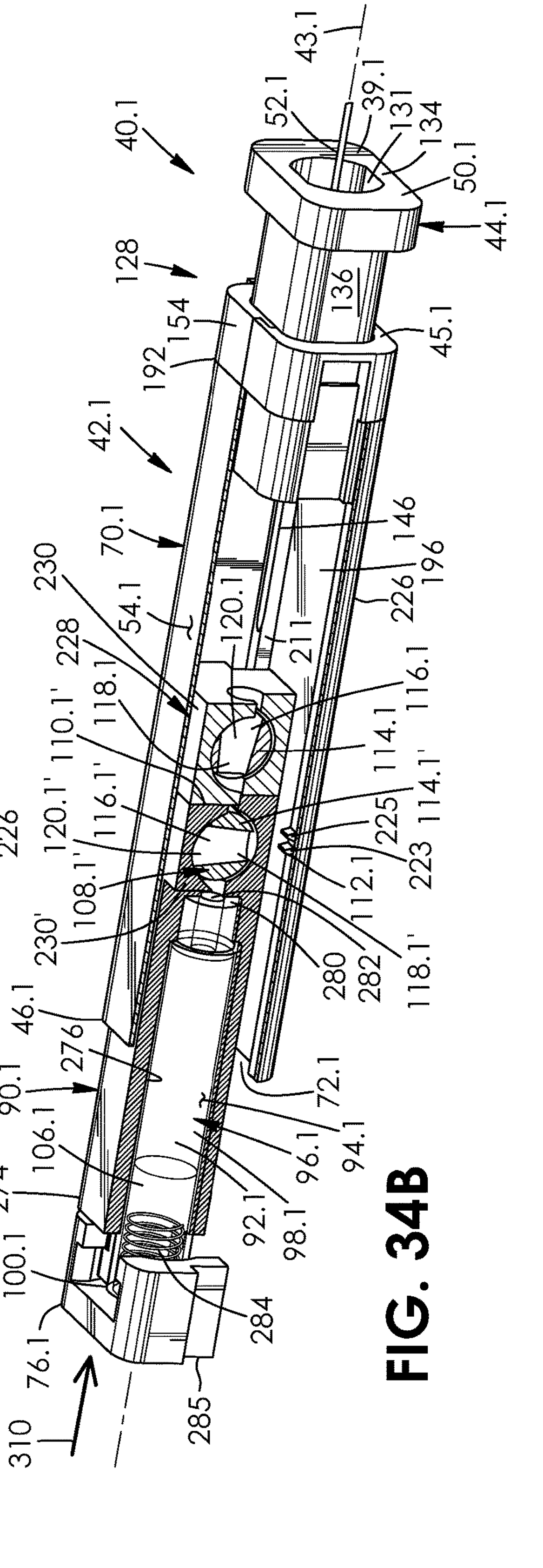
FIG. 34B is an exploded view of the medicament injector in the same position of FIG. 34A, with the cartridge in the processor of being inserted into the cartridge-accepting receptacle and sectional views of the valves with the second valve show in the open position thereof and the first valve in the closed position thereof.

Referring to FIG. 33A, insertion of valve 108.1 into the cartridge-accepting receptacle 70.1 causes gears 258 and 112.1 to engage with each other, such that the valve 108.1 moves from the closed position seen in in FIG. 33B to an open position seen in FIG. 34B. Passageway 116.1 is in fluid communication with apertures 254 and 254 of the valve housing seen in FIG. 27F when the valve 108.1 in the open position.

Figures 30A, 30B, 30C, 30D, 30E:
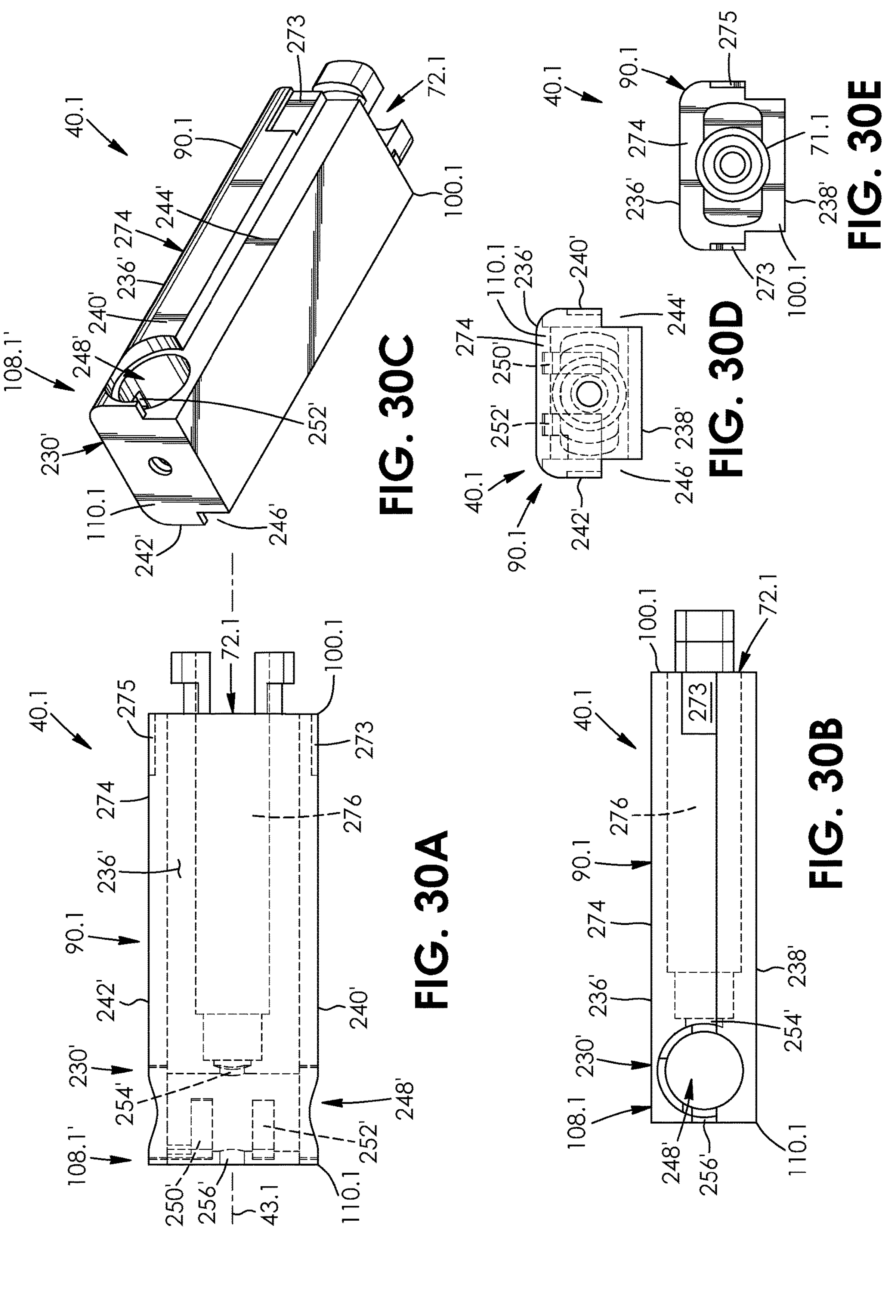
FIG. 30A is a top plan view of the body of the cartridge of FIG. 29.
FIG. 30B is a left side elevation view of the body of the cartridge of FIG. 30A.
FIG. 30C is a bottom, front, right side perspective view of the body of the cartridge of FIG. 30A.
FIG. 30D is a front elevation view of the body of the cartridge of FIG. 30A.
FIG. 30E is a rear elevation view of the body of the cartridge of FIG. 30A.

As seen in FIG. 26, the medicament injector 40.1 includes an interchangeable cartridge 90.1. Needle 146 extends towards the cartridge. As seen in FIG. 35, valve 108.1 is interposed between the needle assembly 128 and the cartridge. Referring back to FIG. 26, the cartridge 90.1 includes a barrier member, in this example a valve 108'. Like parts have like numbers as the valve 108.1 seen in FIGS. 27A to 27F with the addition of '. Referring to FIGS. 30A and 30C, the valve includes a valve housing 230' adjacent to end 110.1' thereof. The valve housing has a bore 248' which extends between sides 240' and 242' thereof. The valve housing 230' includes a pair of spaced-apart recessed channels 250' and 252' in communication with bore 248' and also adjacent to end 110.1 thereof. As seen in FIG. 26, the valve 108.1' includes a valve body 114.1' shaped to fit within bore 248' and engage with the valve housing in a substantially similar manner as valve body 114.1 with valve housing 230. As seen in FIG. 30A, the cartridge 90.1 includes an aperture 256' which is in fluid communication with bore 248'.

Referring to FIG. 30C, the cartridge 90.1 includes a cartridge housing 274 of which valve housing 230' is integrally connected and formed therewith. The cartridge housing has a pair of spaced-apart lower recessed regions 244' and 246' along sides 240' and 242' thereof. As seen in FIG. 33A, the valve housing 230 is shaped to slidably extend within bore 196 of the cartridge-accepting receptacle 70.1 with protrusions 209 and 211 extending within the recessed regions 244' and 246' of the cartridge housing.

Referring to FIGS. 25C and 30C, cartridge 90.1 is shaped to selectively fit within and couple to the cartridge-accepting receptacle via a locking mechanism, in this example a snap-fit system. The snap-fit system comprises catch members 212 and 214 seen in FIG. 25C which couple with corresponding outer female locking members, in this example recessed portions 273 and 275, seen in FIG. 30A. The recessed portions extend inwards from sides 240' and 242' of the cartridge housing 274 and are positioned to extend end 100.1 towards end 110.1 of the cartridge 90.1.

Figure 29:
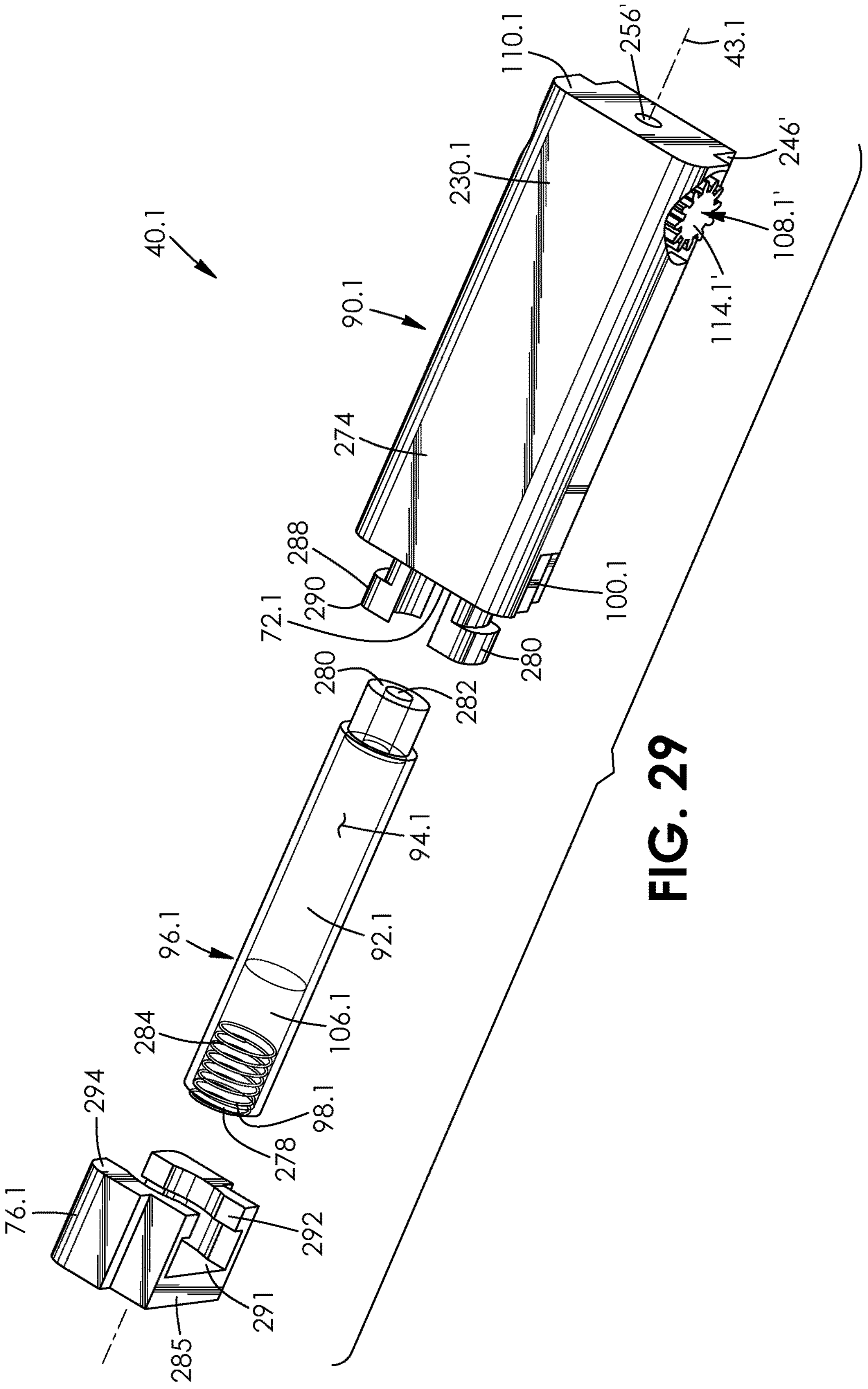
FIG. 29 is a top, right side, front exploded view of the cartridge of FIG. 26, the cartridge including a body, a barrel containing medicament, and a retaining member shown in an unlocked position.

Referring to FIG. 30A, the cartridge housing 274 extends between ends 110.1 and 100.1 thereof. The cartridge 90.1 includes a central bore 276 which extends from open end 100.1 thereof towards end 110.1 thereof. Bore 276 extends along axis 43, extends perpendicular to bore 248' in this example and is in fluid communication with bore 248' via aperture 254'. As seen in FIG. 29, the cartridge 90.1 includes a body, in this example a barrel 96.1 within which medicament 92.1 is contained or received. As seen in FIG. 33B, bore 276 is shaped to receive the barrel.

Referring back to FIG. 29, the barrel 96.1 has a bore 98.1 with an open first end 278 and a second end 280 with a sealed opening 282. The barrel includes a piston 106.1 between the ends thereof. The medicament 92.1 is positioned within the bore 98.1 between the piston and sealed opening 282. The cartridge 90.1 includes a resilient member, in this example a coil spring 284 positioned within the bore and extending from end 278 towards end 280. The coil spring is configured to bias the piston 106.1 and thus the medicament 92.1 towards the sealed opening 282. The spring 284 thus causes the medicament to be enclosed within the barrel 96.1 under pressure. The barrel 96.1, spring 284 and piston 106.1 may thus be referred to as a spring-loaded delivery system.

Figure 32A:
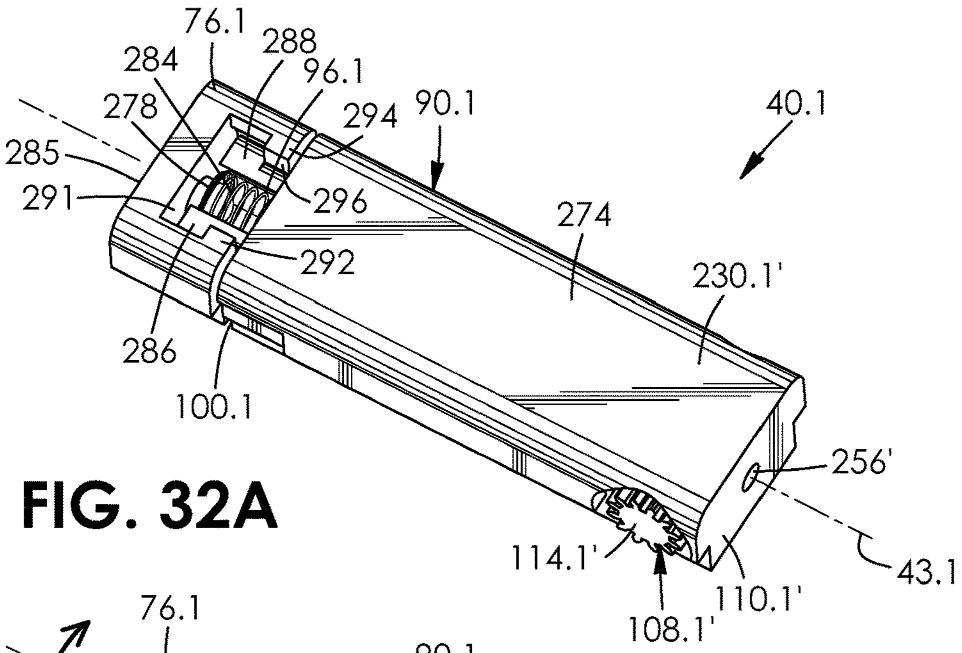
FIG. 32A is a front, top, right side perspective view of the cartridge of FIG. 29, with the retaining member shown in a locked position.
Figure 32B:
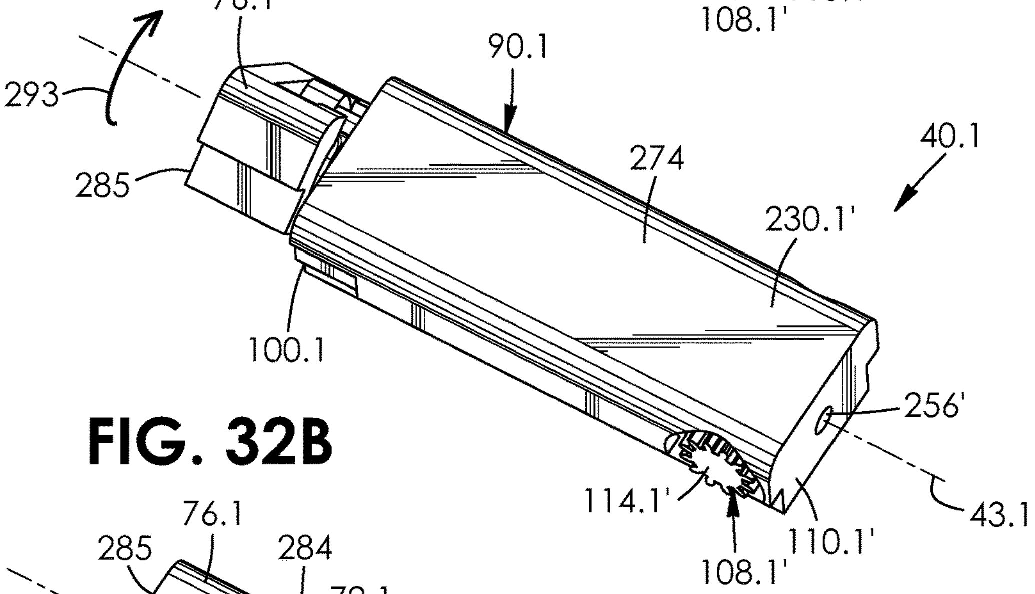
FIG. 32B is a front, top, right side perspective view of the cartridge of FIG. 29, with the retaining member shown in a partially unlocked position.

Referring to FIG. 29, the medicament injector 40.1 includes a retaining member 76.1 which is shaped to retain in place and bias spring 284 towards piston 106.1 and selectively couple to end 100.1 of the cartridge 90.1 as seen in FIG. 32A. The retaining member includes an end wall 285 which extends perpendicular to axis 43.1 in this example. In this example and referring to FIG. 29, the cartridge includes a pair of spaced-apart, resilient male members 286 and 288 each of which extend in part about barrel 96.1 and which have enlarged ends 290.

Figure 32C:
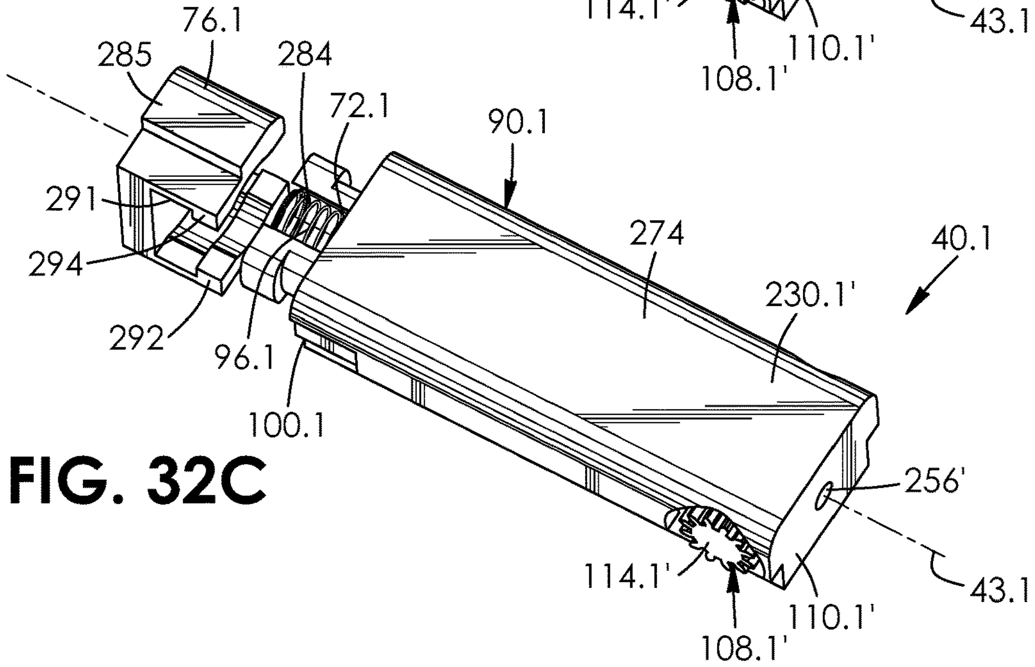
FIG. 32C is a front, top, right side perspective view of the cartridge of FIG. 29, with the retaining member shown in a fully unlocked position and spaced apart from the body of the cartridge.

As seen in FIG. 32C, the retaining member has a complementary shape, in this example in the form of a C-shape with an inner channel 291, and inwardly-extending catches 292 and 294 which couple to and extend outwards from end wall 285. As seen in FIG. 32C, the retaining member is shaped enclose the male members 286 and 288 in a first angular configuration and insertion position. Rotation of the retaining member thereafter, as shown by arrow 293 in FIG. 32B, causes catches 292 and 294 to fit within corresponding recesses 296 of the male members 286 and 288 in a locked mode. The enlarged ends 290 of the male members are configured to fit within and be enclosed by inner channel 291 of the retaining member 76.1. The retaining member 76.1 holds the spring 284 and barrel 96.1 in place within the cartridge housing 274. Reversing the above steps enable one to selectively access and remove the barrel if desired.

Figure 31A:
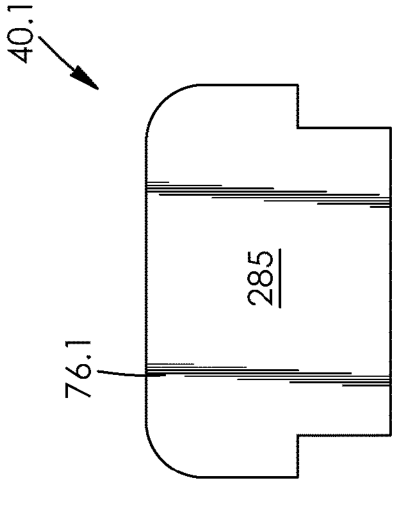
FIG. 31A is a rear elevation view of the retaining member of FIG. 20.
Figure 31B:
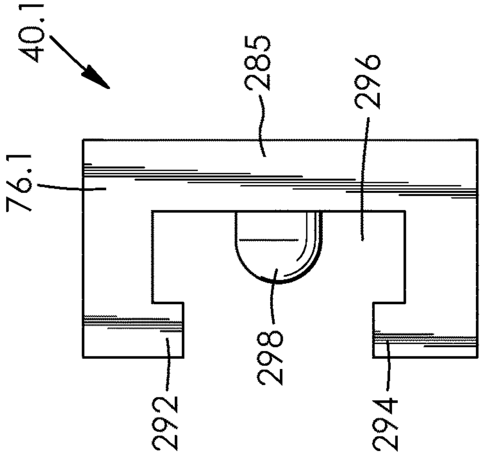
FIG. 31B is top plan view of the retaining member of FIG. 31A.
Figure 31C:
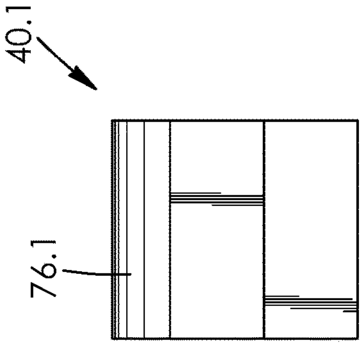
FIG. 31C is a left side elevation view of the retaining member of FIG. 31A.
Figure 31D:
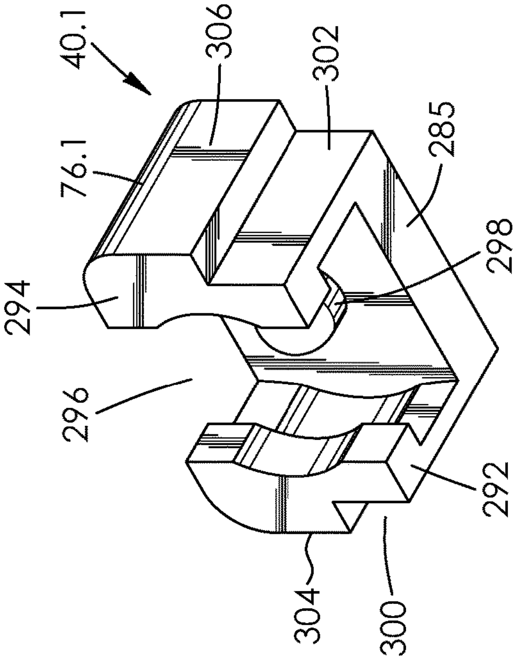
FIG. 31D is a front, bottom, left side perspective view of the retaining member of FIG. 31A.
Figure 31E:
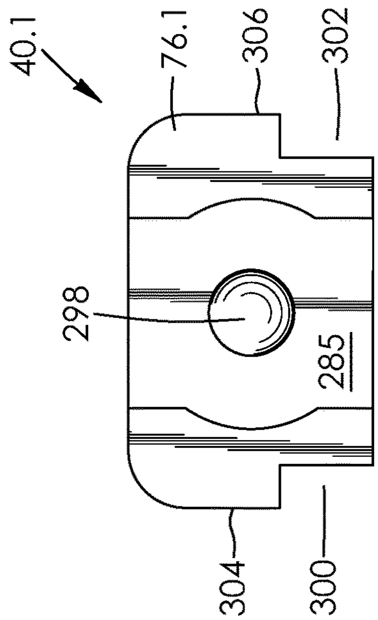
FIG. 31E is a front elevation view of the retaining member of FIG. 31D.

As seen in FIG. 31D, the retaining member 76.1 includes a protrusion, in this example a centrally-positioned knob 298 which couples to end wall 285, extends within channel 291 and is shaped to fit within open end 278 of barrel 96.1.

As seen in FIG. 31D, the retaining member 76.1 has pair of spaced-apart lower recessed regions 300 and 302 along sides 304 and 306 thereof. As seen in FIG. 35, the retaining member is shaped to slidably extend in part within bore 196 of the cartridge-accepting receptacle 70.1 with protrusions 209 and 211 extending within corresponding the recessed regions 300 of the retaining member.

The above is only one example of one manner of holding barrel 96.1 in place within cartridge housing 90.1 and is not strictly required. Also, in other embodiments, the barrel may be held in place without access thereto being permitted, for example.

In operation and referring to FIG. 33B, in the closed position of the valve 108.1' fluid communication between the cartridge 90.1 and the needle assembly 128 is inhibited. Valve 108.1 further inhibits access to needle 146 when the cartridge is in the pre-injection mode seen in FIG. 33B.

Insertion of the cartridge 90.1 within open end 194 of the cartridge-accepting receptacle 70.1, as shown by arrow 308, causes end 110.1 of the cartridge to abut and push against valve housing 230. This causes the valve 108.1 to move towards depressor housing 154. As seen in FIG. 33A, teeth 223 and 225 engage with gears 258 of valve body 114.1, causing the valve 108.1 to move from the closed position seen in FIG. 33B to an open position seen in FIG. 34B. A first barrier to the inner needle 146 is thus removed.

As the cartridge 90.1 continues to be inserted into the cartridge-accepting receptacle 70.1, teeth 223 and 225 engage with gears 258' of valve 108.1' seen in FIG. 34A. This causes valve 108.1' to move from the closed position seen in FIG. 34B to the open position seen in FIG. 35. A second barrier to the medicament 92.1 is thus removed.

As the cartridge 90.1 further continues to be inserted into the cartridge-accepting receptacle, as shown by arrow 310 in FIGS. 34A and 34B, inner needle 146 extends through passageways 116.1 and 116.1' of the valve 108.1 and 108.1' as seen in FIG. 35, and front end 234 of valve housing 230 abuts end 164 of depressor housing 154.

Referring to FIG. 35, medicament is administered to a patient by inserting needle 52.1 into the patient such that flange 134 of depressor 44.1 abuts the patient and biases the depressor inwards, as shown by arrow 312. This causes inner needle 146 to pierce sealed opening 282, extend within barrel 96.1 and access medicament 92.1 as seen in FIG. 37. Thus, inserting cartridge 90.1 into the cartridge-accepting receptacle 70.1 and thereafter inwardly biasing the depressor 44.1 from the protected needle mode to an at least partially retracted mode causes the inner needle to be in fluid communication with the interior 94.1 of the cartridge. The spring-biased piston 106.1 thus biases the medicament 92.1 outwards of the barrel when the sealed opening is pierced by the needle as seen by FIG. 37. The medicament is therefore accessible via the inner needle 146.

The medicament is thus accessible via the applicator 42.1 when the cartridge is fully inserted into the cartridge-accepting receptacle. The needle assembly 128 is also therefore selectively in fluid communication with the medicament 92.1 when the cartridge 90.1 is inserted into the applicator 42.1. The cartridge is configured to only enable release of the medicament upon the cartridge being fully inserted into the applicator and the depressor 44.1 being thereafter actuated.

Figure 38:
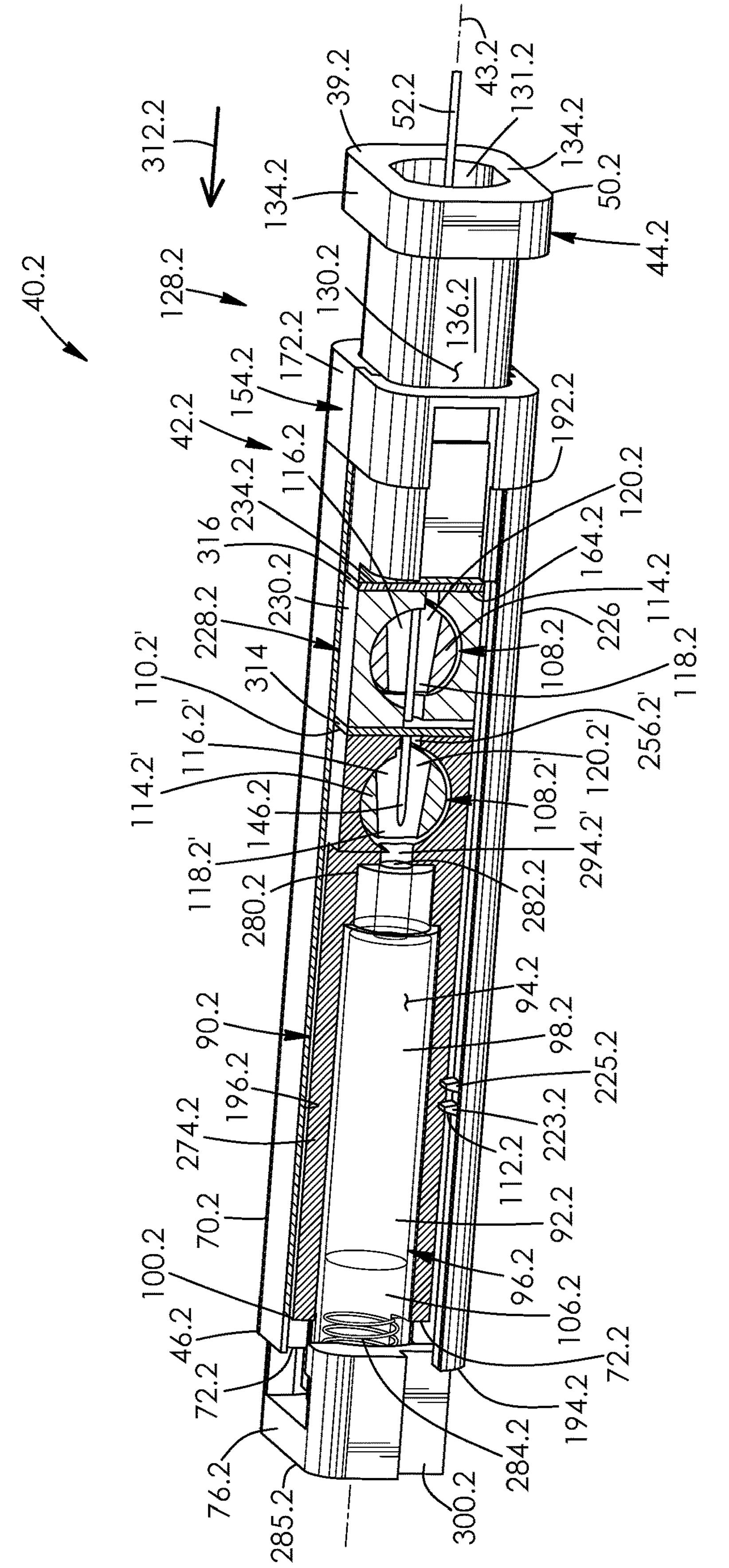
FIG. 38 is a side elevation view of a medicament injector according to a third embodiment.

FIG. 38 shows a medicament injector 40.2 according to a third aspect. Like parts have like numbers and function as the embodiment shown in FIGS. 20 to 37 with decimal extension ".2" replacing decimal extension ".1". Medicament injector 40.2 is substantially the same as medicament injector 40.1 as shown in FIGS. 20 to 37 with the exception that it further includes a pair of seal members, in this example elastoplastic membranes 314 and 316 that are pieced by needle 146.2 when depressor 44.1 is biased inwards as shown by arrow 312.2.

FIGS. 39 to 50 show a medicament injector 40.3 according to a fourth aspect. Like parts have like numbers and function as the embodiment shown in FIGS. 20 to 37 with decimal extension ".3" replacing decimal extension ".1" and being added for parts not previously having decimal extensions. Medicament injector 40.3 is similar to medicament injector 40.1 shown in FIGS. 20 to 37 with the following exceptions.

Figure 40:
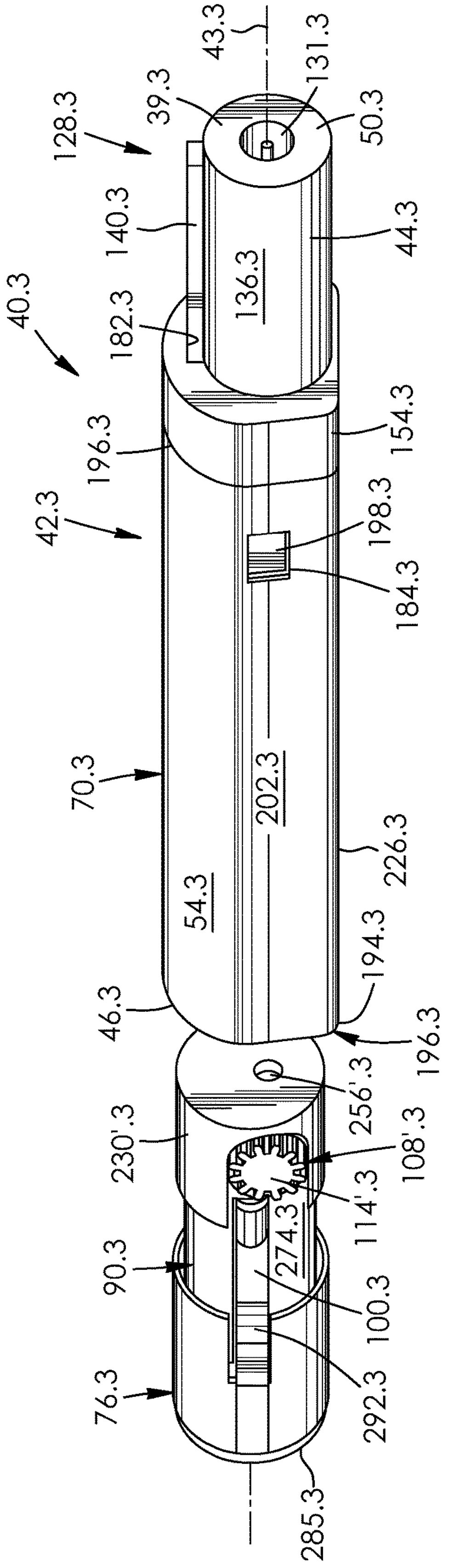
FIG. 40 is a front, right side exploded view of the medicament injector of FIG. 39.
Figure 41:
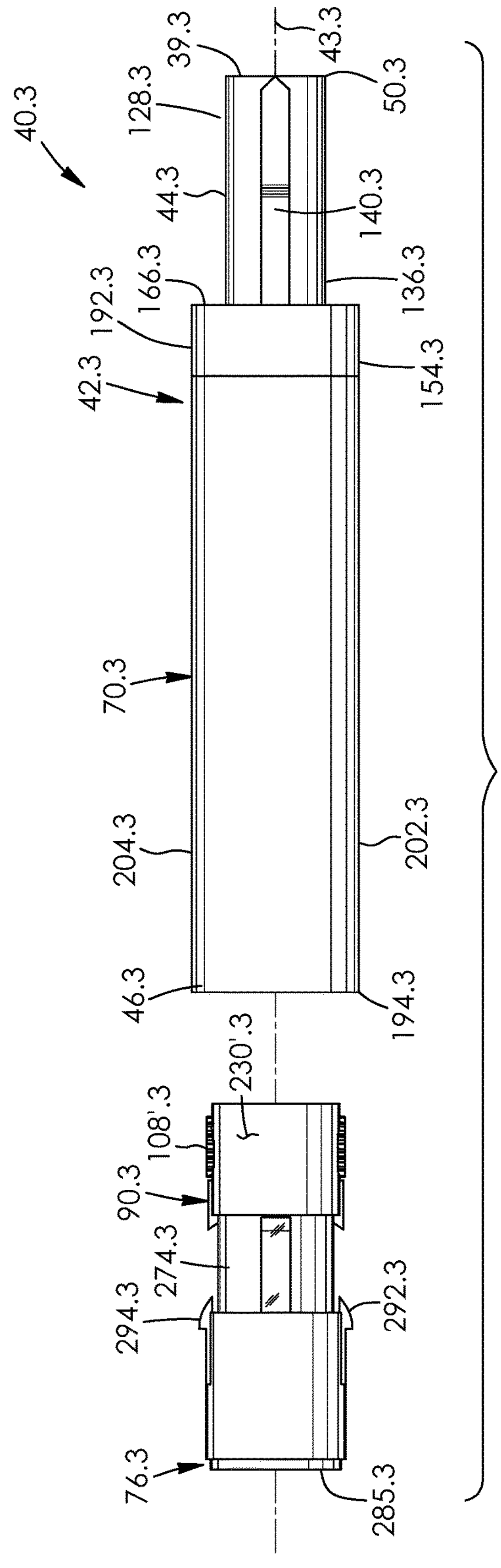
FIG. 41 is a top plan view thereof.
Figure 42:
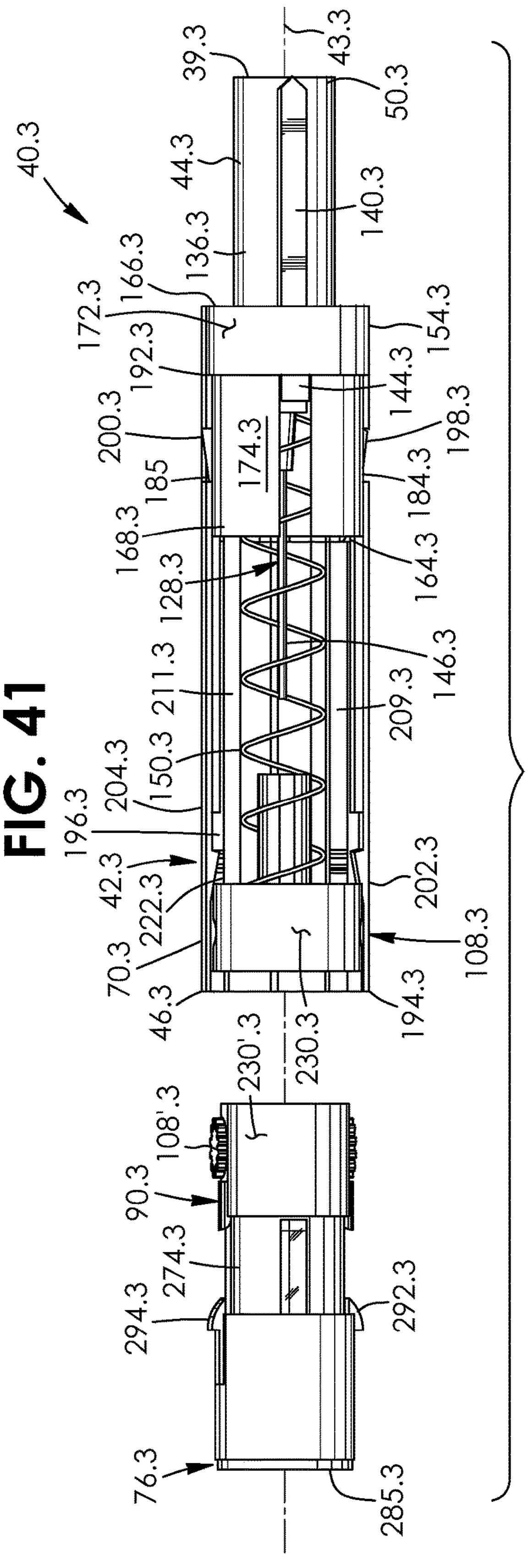
FIG. 42 is a top plan view of the medicament injector of FIG. 39 similar to FIG. 41, with a top half of the cartridge-accepting receptacle thereof being removed to reveal interior parts thereof.

As seen in FIG. 40, depressor 44.3 includes a central protrusion 140.3 coupled to and extending radially outwardly and upwards from sleeve portion 136.3 thereof. The protrusion is slidably received within corresponding channel 182.3 of depressor housing 154.3. The sleeve portion 136.3 of the depressor 44.3 is circular in lateral cross-section in this example.

Figure 43:
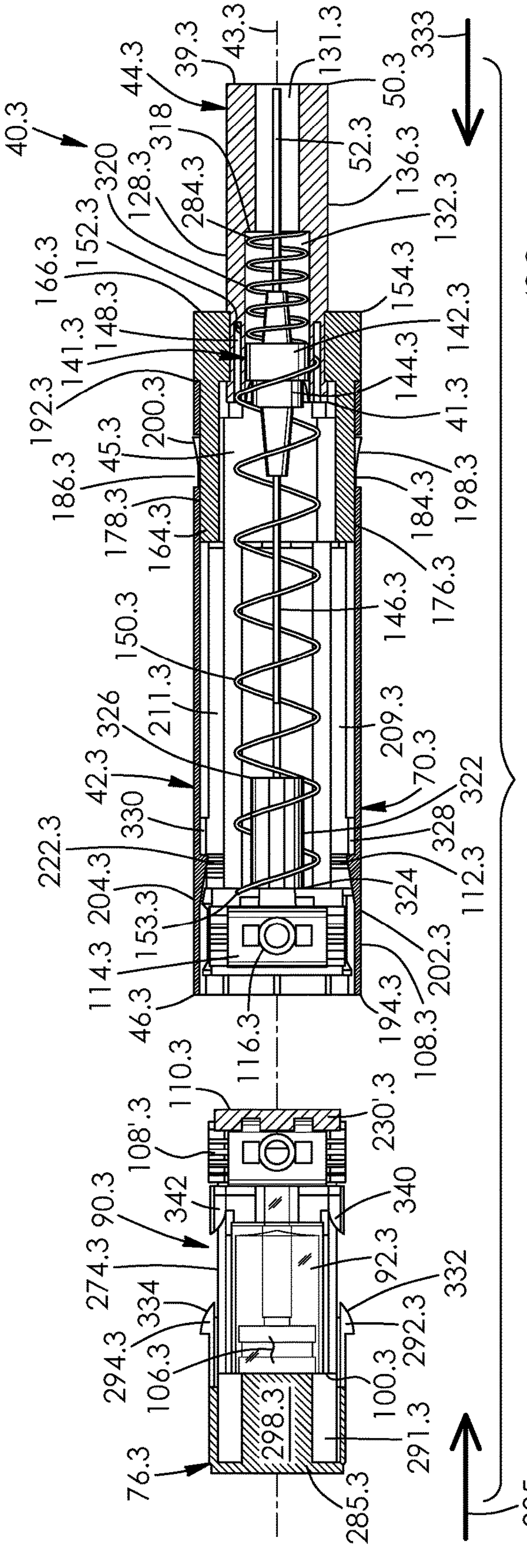
FIG. 43 is a top plan view of the medicament injector of FIG. 39 with top halves of the depressor, depressor housing, cartridge-accepting receptacle and cartridge retaining member thereof being removed to reveal interior parts thereof.

As seen in FIG. 43, the depressor housing 154.3 includes at least one and, in this example, a pair of spaced-apart, resilient, catch members 198.3 and 200.3 which couple to and extend radially outwards from opposed walls 176.3 and 178.3 thereof. The cartridge-accepting receptacle 70.3 has corresponding recessed portions, in this example apertures 184.3 and 186.3 shaped to receive the respective catch members. The depressor housing 154.3 couples to the open end 192.3 of the cartridge-accepting receptacle thereby. The depressor housing is selectively removable from the cartridge-accepting receptacle by pressing radially inwards on the catch members 198.3 and 200.3 and thus dislodging the catch members from the apertures 184.3 and 186.3.

Figure 39:
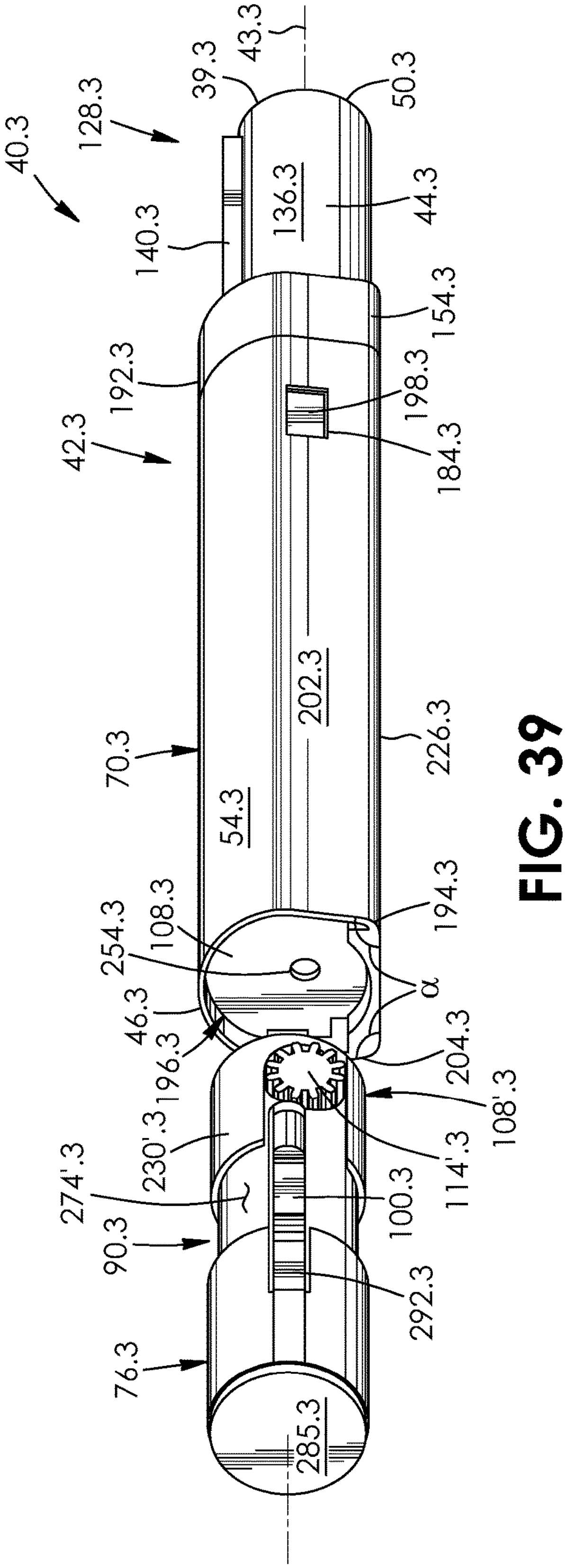
FIG. 39 is a rear, right side exploded view of a medicament injector according to a fourth embodiment, with an interchangeable cartridge thereof shown spaced-apart rearward from a cartridge-accepting receptacle thereof, the medicament injector including a depressor shown in a pre-injection mode.

As seen in FIG. 39, walls 202.3 and 204.3 of cartridge-accepting receptacle 70.3 are substantially planar and couple to and extend outwards at obtuse angles $\alpha$ relative to wall 226.3 of cartridge-accepting receptacle 70.3 in this example. Wall 54.3 of the cartridge-accepting receptacle couples to and extends between walls 202.3 and 204.3 and is outwardly convex in this example.

Figure 44:
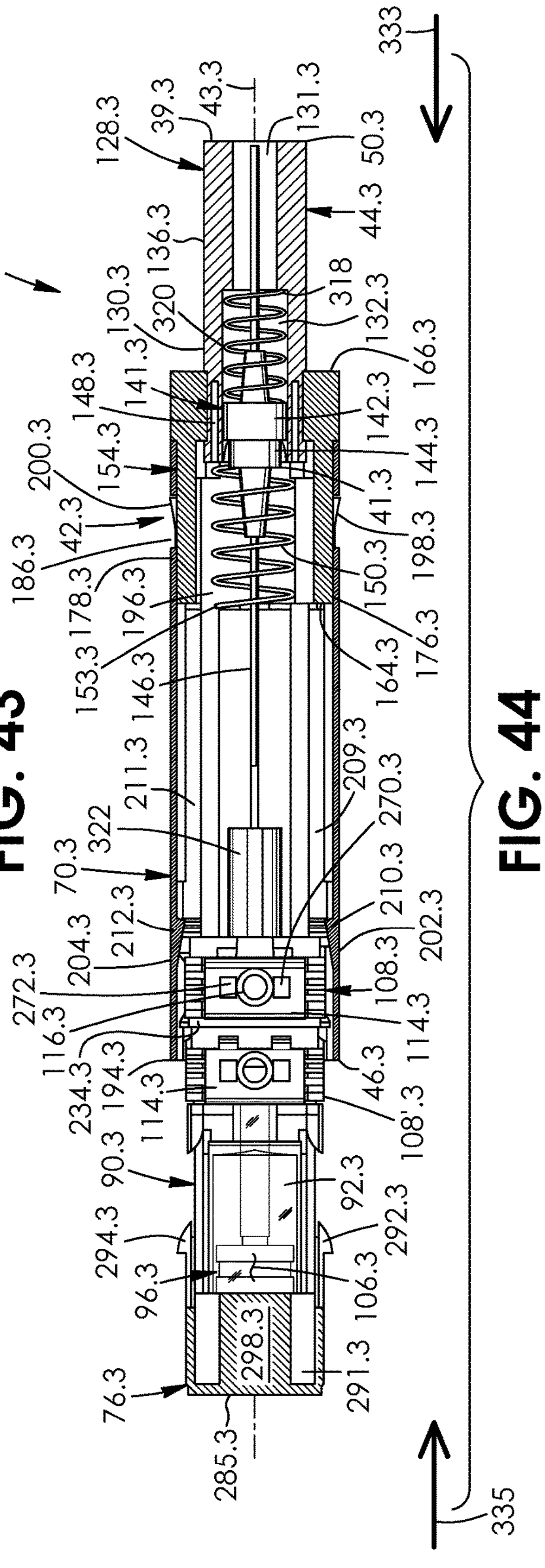
FIG. 44 is a top plan view of the medicament injector of FIG. 43 with top halves of the depressor, depressor housing, cartridge-accepting receptacle and cartridge retaining member thereof being removed to reveal interior parts thereof and with an interchangeable cartridge thereof shown in the process of being inserted into the cartridge-accepting receptacle.

As seen in FIG. 44, depressor 44.3 has an inner bore 132.3 which extends from end 41.3 thereof towards end 39.3 thereof. The hub 141.3 of the needle assembly 128.3 is received within and is movable relative to the inner bore of the depressor. The depressor 44.3 has a shoulder 318 extending radially between inner bore 132.3 and outer bore 131.3.

The medicament injector 40.3 includes a second resilient member, in this example a coil spring 320 extending between hub 141.3 of the needle assembly 128.3 and shoulder 318 of the depressor. The coil spring biases the needle assembly axially inwards from the depressor 44.3 and towards the cartridge 90.3 in a first direction 333. The needle assembly 128.3 is thus resiliently biased towards the cartridge relative to the depressor 44.3.

As seen in FIG. 43, the medicament injector 40.3 includes a needle guiding member, in this example an axially extending sleeve 322 via which needle 146.3 is selectively received. The sleeve has a first or proximal end 324 which couples to and is integrally formed with valve housing 230.3 in this example. The sleeve 322 has a second or distal end 326 spaced-apart from the proximal end thereof.

Figure 45:
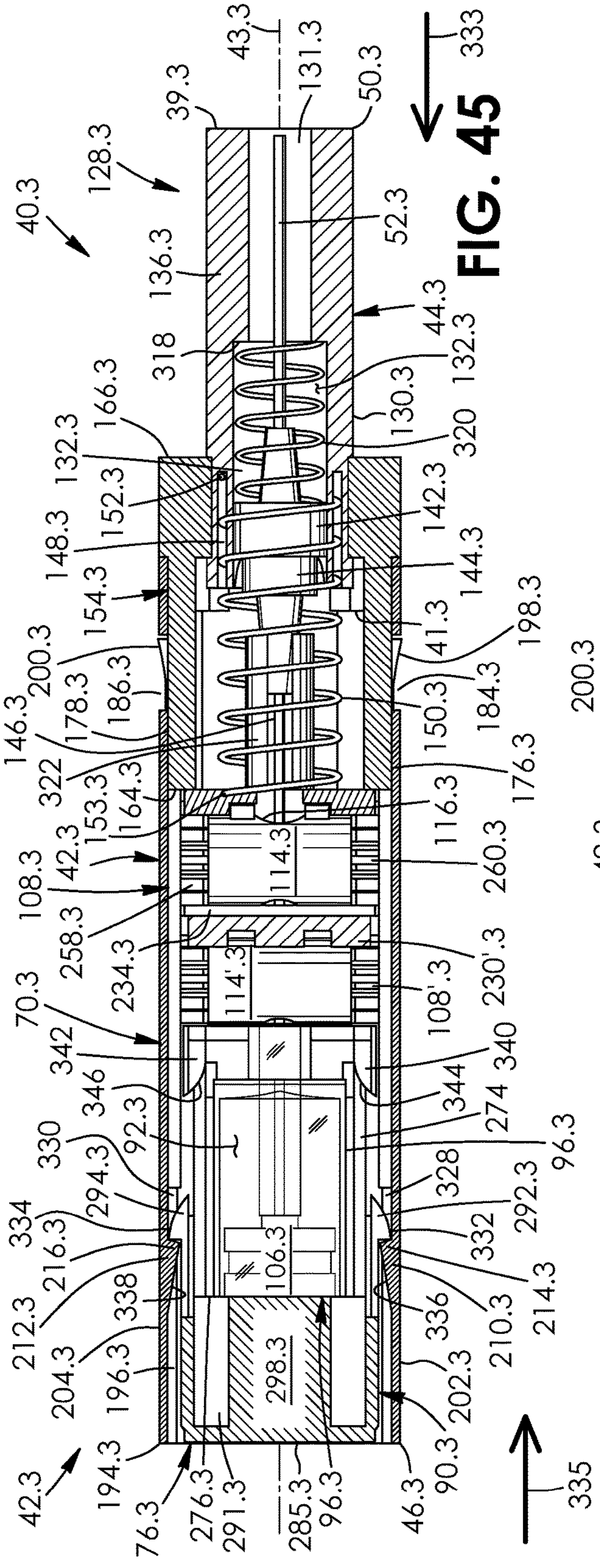
FIG. 45 is a top plan view of the medicament injector of FIG. 44 with top halves of the depressor, depressor housing, cartridge-accepting receptacle and cartridge retaining member thereof being removed to reveal interior parts thereof, and with the interchangeable cartridge shown fully inserted into the cartridge-accepting receptacle.

Still referring to FIG. 43, the medicament injector 40.3 includes a further resilient member, in this example a second coil spring 150.3 which extends between the cartridge 90.3 and depressor 44.3. In this example the spring has a first end 152.3 which fits within annular recess 148.3 of depressor 44.3. Second end 153.3 of the spring 150.3 extends about sleeve 332 and abuts valve housing 230.3 in this example. Referring to FIG. 45, when cartridge 90.3 is inserted into cartridge-accepting receptacle 70.3, spring 150.3 resiliently biases depressor 44.3 outwards from the cartridge 90.3 in direction 335.

As seen in FIG. 39, valve housing 230'.3 selectively couples to cartridge housing 274.3 in this example.

Referring to FIG. 45, the cartridge-accepting receptacle 70.3 includes a first of one or more female members and one or more male members, in this example a pair of spaced-apart female members, in this case recessed portions 328 and 330 located adjacent walls 202.3 and 204.3, respectively.

Cartridge retaining member 76.3 is circular in lateral profile in this example. The retaining member includes a second of one or more female members and one or more male members, in this example a pair of spaced-apart male members, in this case a pair of spaced-apart resilient, radially-outwardly extending tapered catches 292.3 and 294.3. The catches are triangular in cross-section in this example, with outer surfaces 332 and 334 sloped radially-inwards in a second direction 335 extending from the first end 46.3 of the applicator 42.3 towards the second end 50.3 of the applicator. The second direction is opposite the first direction 333. The catches 292.3 and 294.3 are spaced-apart from the end wall 285.3 of the retaining member 76.3 and protrusion 298.3 is spaced therebetween.

Still referring to FIG. 45, the medicament injector 40.3 further includes at least one and in this example a pair of spaced-apart inner tapered members, in this case radially-inwardly extending tapered catches 210.3 and 212.3 of the cartridge-accepting receptacle 70.3. The catches are triangular in cross-section in this example, with outer surfaces 336 and 338 sloped radially-inwards in said second direction 335 extending from the first end 46.3 of the applicator 42.3 towards the second end 50.3 of the applicator.

Figure 46:
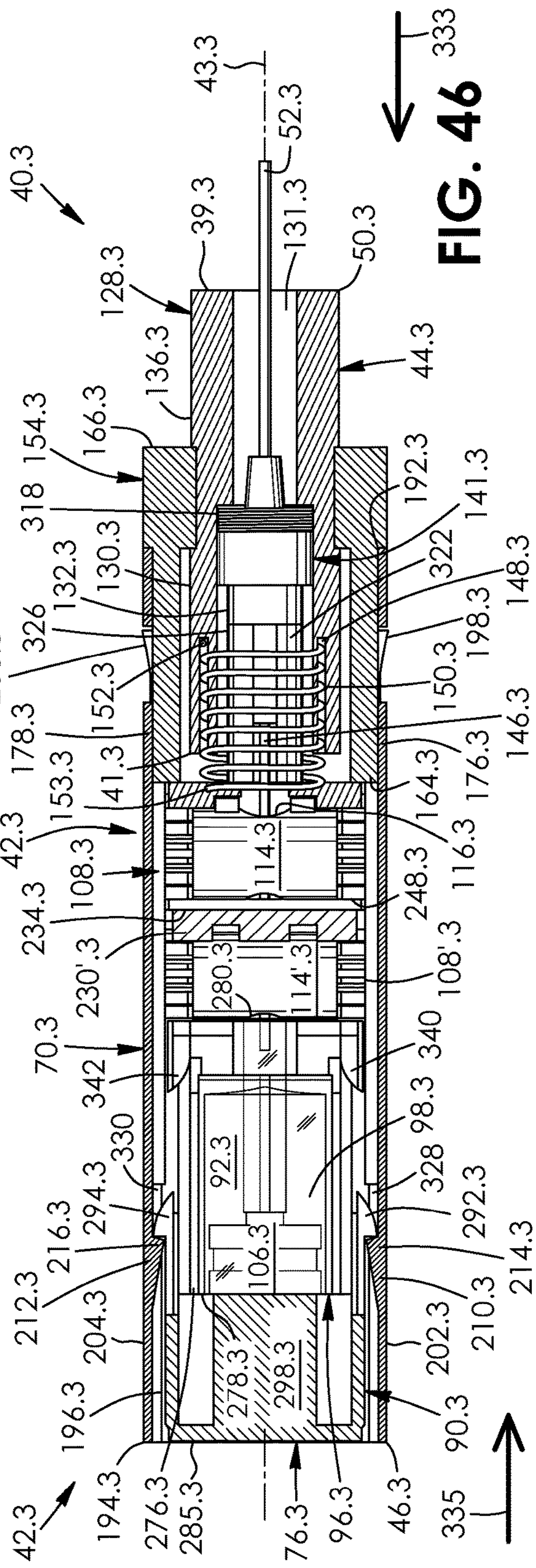
FIG. 46 is a top plan view of the medicament injector of FIG. 45 with top halves of the depressor, depressor housing, cartridge-accepting receptacle and cartridge retaining member thereof being removed to reveal interior parts thereof, with the interchangeable cartridge shown fully inserted into the cartridge-accepting receptacle, with the depressor partially retracted towards the cartridge-accepting receptacle, moving towards an injection mode, and exposing a distal needle of the needle assembly, and with the needle assembly being shown in fluid communication with medicament of the interchangeable cartridge.

The tapered catches 292.3 and 294.3 of the retaining member 76.3 are shaped to be selectively received within respective the recessed portions 328 and 330 of the cartridge-accepting receptacle 70.3 when the cartridge is fully inserted into the cartridge-accepting receptacle as seen in FIGS. 45 and 46. The tapered catches 210.3 and 292.3 and recessed portion 328, and tapered catches 212.3 and 294.3 and recessed portion 330 interengage when the cartridge 90.3 is fully inserted into the cartridge-accepting receptacle 70.3 and inhibit removal of the cartridge from the cartridge-accepting receptacle. The tapered catches 210.3 and 212.3 of the cartridge-accepting receptacle 70.3 abut against and selectively couple with respective tapered catches 292.3 and 294.3 of the retaining member 76.3 when the cartridge is fully inserted within the cartridge-accepting receptacle. Protrusion 298.3 of the retaining member 76.3, when the cartridge 90.3 is fully inserted into the cartridge-accepting receptacle 70.3 and snap-fit in place via the catches, is configured together with spring 150.3 to apply pressure to piston 106.3 and cause medicament 92.3 and barrel 96.3 to be under pressure.

Still referring to FIG. 45, the cartridge 90.3 further includes at least one and in this example a pair of spaced-apart projections or dislodgement members, in this case tapered members 340 and 342 adjacent to valve housing 230'.3 and facing catches 292.3 and 294.3 of the retaining member 76.3. The tapered members of the cartridge have outer surfaces 344 and 346 sloped radially-inwards from said second direction 335 extending from the first end 46.3 of the applicator 42.3 towards the second end 50.3 of the applicator in this example; however this is not strictly required.

The medicament 92.3 is in fluid communication with needle 146.3 when cartridge 90.3 is inserted into the cartridge-accepting receptacle 70.3 and depressor 44.3 is moved from the protected needle mode seen in FIG. 45 to a partially retracted mode seen in FIG. 46. The piercing of barrel 96.3 by needle 146.3 releases pressure therewithin, and causes piston 106.3 to move towards depressor 44.3 in direction 335 as seen in FIG. 47.

Figures 47, 48:
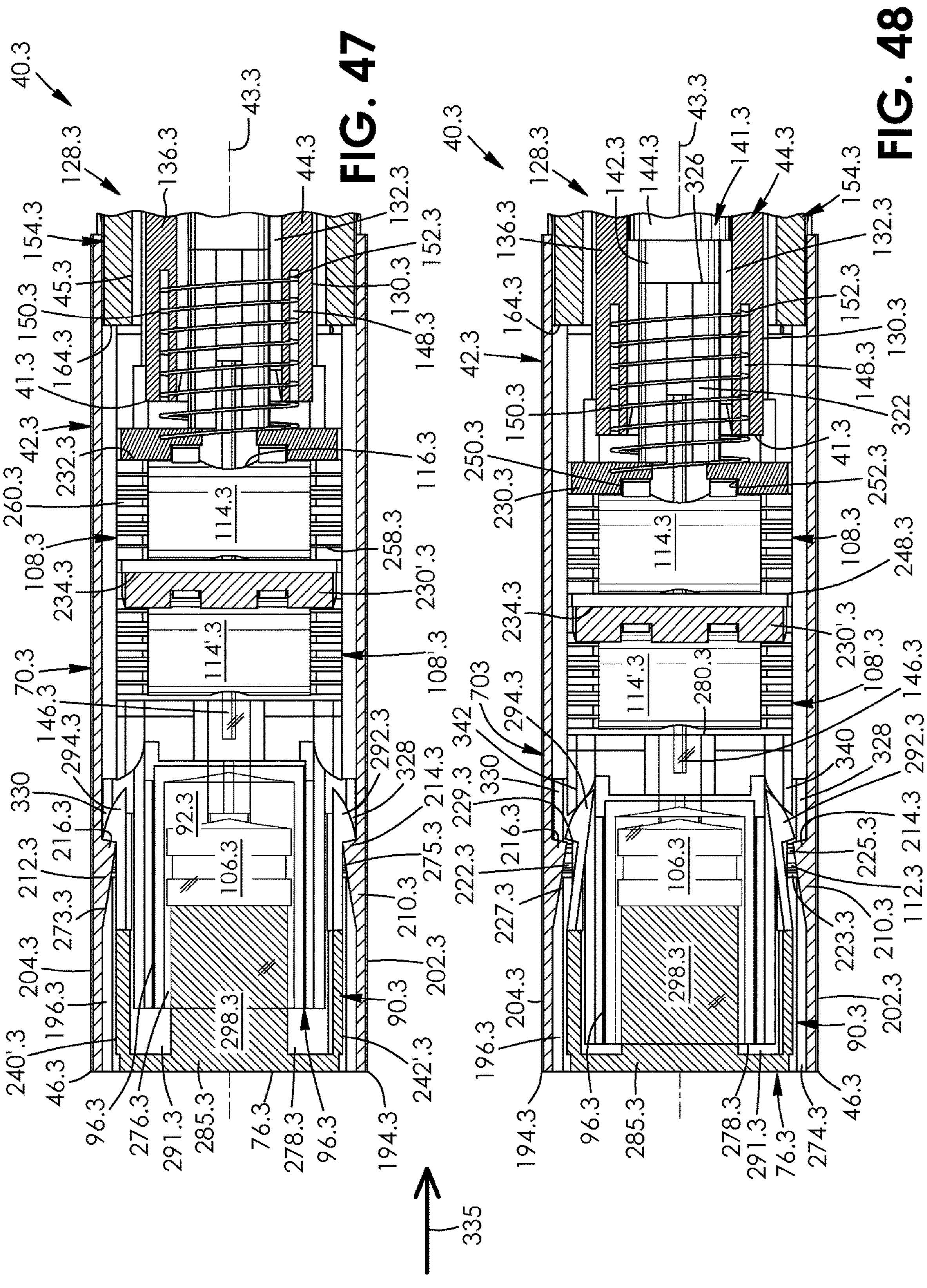
FIG. 47 is a top plan view of the medicament injector of FIG. 46 shown in fragment, with top halves of the depressor, depressor housing, cartridge-accepting receptacle and cartridge retaining member thereof being removed to reveal interior parts thereof, with the interchangeable cartridge shown fully inserted into the cartridge-accepting receptacle and with the depressor more fully depressed towards the cartridge-accepting receptacle and shown in an injection mode, and with the valves, valve housings, depressor and depressor housing of the medicament injector being shown moving towards the cartridge as the medicament is depleted therefrom.
FIG. 48 is a top plan view of the medicament injector of FIG. 47 shown in fragment, with top halves of the depressor, depressor housing, cartridge-accepting receptacle and cartridge retaining member thereof being removed to reveal interior parts thereof, with the medicament being fully depleted from the barrel and with tapered members of one of the valve housings shown in the process of dislodging the cartridge retaining member, and thus the cartridge, from the cartridge-accepting receptacle.
Figure 49:
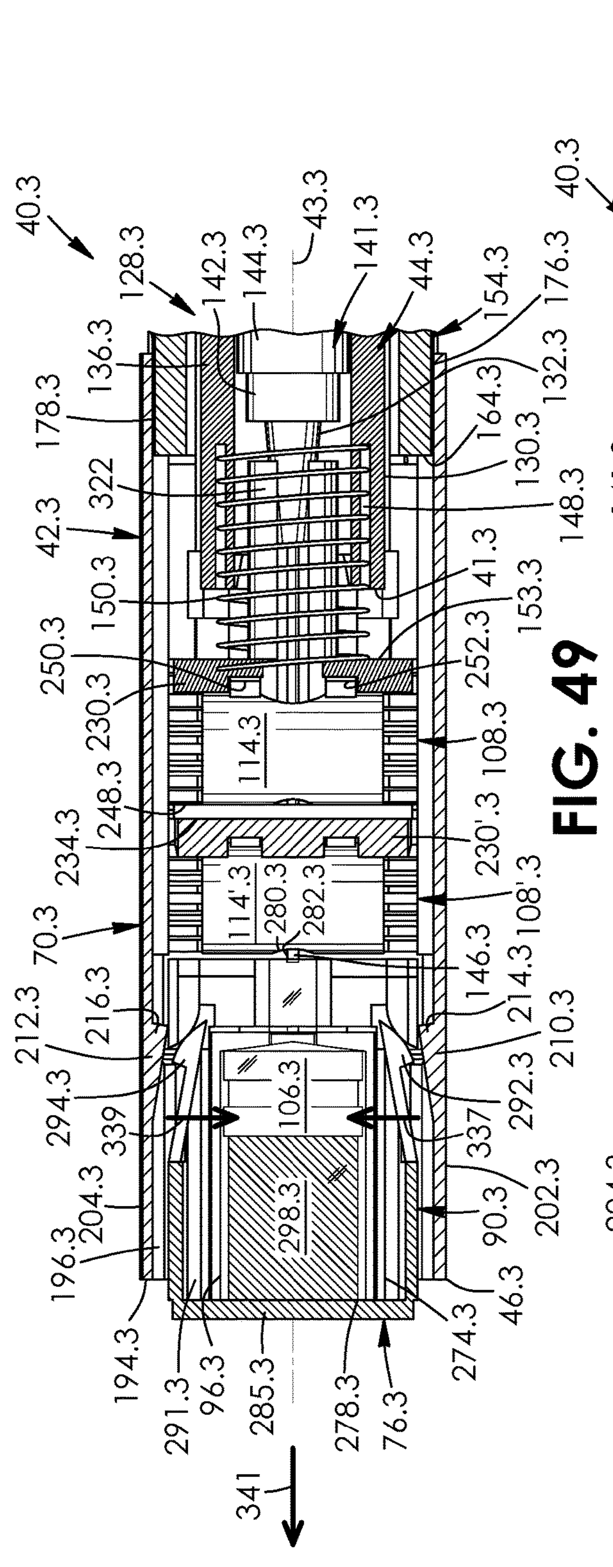
FIG. 49 is a top plan view of the medicament injector of FIG. 48 shown in fragment, with top halves of the depressor, depressor housing, cartridge-accepting receptacle and cartridge retaining member thereof being removed to reveal interior parts thereof, and with the tapered members of the valve housing more fully biasing catch members of the cartridge retaining member radially inwards and more fully dislodging the cartridge retaining member from the cartridge-accepting receptacle.
Figure 50:
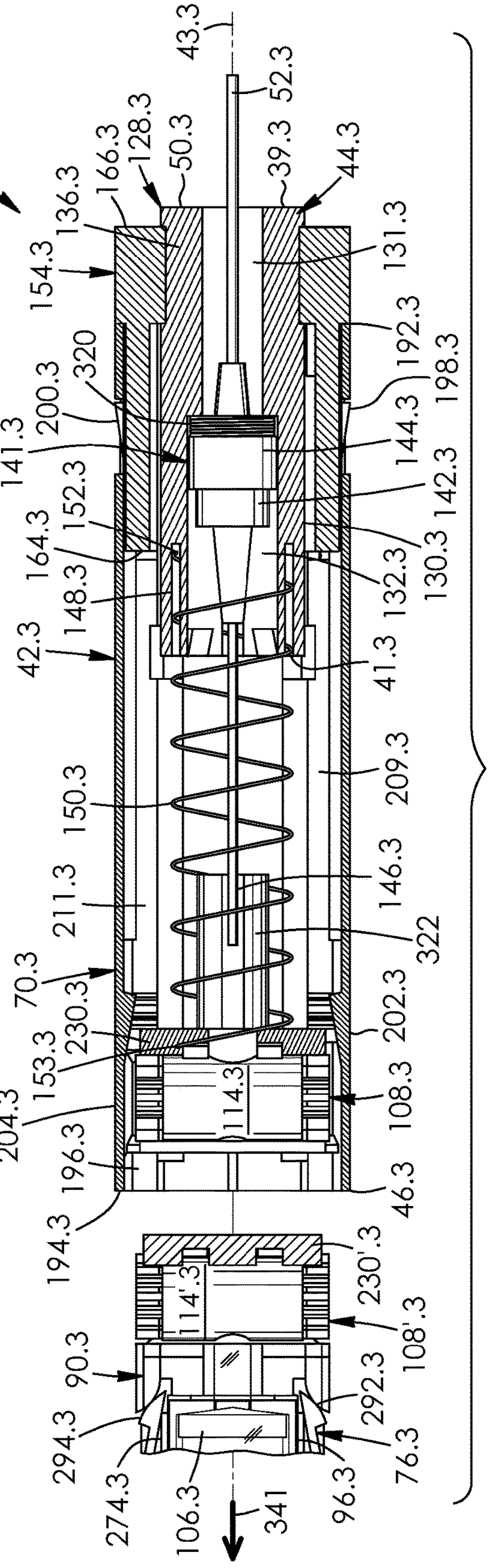
FIG. 50 is a top plan view of the medicament injector of FIG. 49 shown in fragment, with top halves of the depressor, depressor housing, cartridge-accepting receptacle and cartridge retaining member thereof being removed to reveal interior parts thereof, with the cartridge retaining member and depleted interchangeable cartridge dislodged and spaced-apart from the cartridge-accepting receptacle.

When the depressor 44.3 is moved to the fully retracted mode as seen in FIG. 48, spring 150.3 biases tapered members 340 and 342 of the cartridge 90.3 against tapered catches 292.3 and 294.3 of the retaining member 76.3, with the catches deflecting radially inwards, as seen by arrows 337 and 339 in FIG. 49, and dislodging from recessed portions 328 and 330 of the cartridge-accepting receptacle 70.3, as seen by arrow 341. Movement of the depressor to the fully retracted mode thus causes the catches of the retaining member 76.3 to selectively dislodge from the recessed portions and bias the cartridge 90.3 outwards from the cartridge-accepting receptacle. The tapered members 340 and 342 thus abut catches 292.3 and 294.3 and bias the catches away from catches 214.3 and 216.3 of the cartridge-accepting receptacle 70.3 when the depressor 44.3 is moved to the fully retracted mode. Hub 141.1 abuts the distal end 326 of sleeve 322 when the depressor 44.3 in its fully retracted mode. Moving the depressor from the partially retracted mode seen in FIG. 46 to a fully retracted mode seen in FIG. 48 thus causes the cartridge 90.3 to be automatically ejected from the cartridge-accepting receptacle thereafter.

The cartridge-accepting receptacle 70.3 thus returns to a native state once the cartridge 90.3 is used and ejected from the cartridge-accepting receptacle to allow the cartridge-accepting receptacle to accept further cartridges.

The medicament injectors as herein described may provide numerous advantages by for, example, reducing the number of steps and number of components involved in medication delivery via these proposed novel mechanisms to reduce errors and increase speed in time-critical situations to deliver medications. In specific situations, the medicament injector as herein described may make medication delivery easier and safer while reducing the size/bulk of equipment required.

(1) Introduce a novel multi-modular and interchangeable pre-filled medicament cartridge assembly.

(2) The cartridge is pre-filled with medication and designed in such a way to be used with most medications and its associated doses in emergent situations.

(3) The required cartridge selected by the clinical provider for the specific needed clinical situation interfaces/inserts into an accepting injector device that will accommodate the cartridge in a sterile fashion.

(4) Once the cartridge is inserted and loaded into the accepting injector device, pressure applied to the front of the injector device (facing the patient) will further activate a mechanism to deliver the medicament from the cartridge/injector device into the patient.

(5) The user will be able to select the medicament cartridge as needed and load it into the injector device for each given situation/scenario.

(6) This makes the entire process of medication delivery easier, quicker, safer, and saves on the bulk/size of equipment involved.

(7) Sterility is preserved throughout. Mechanism allows for a one direction barrier/sterile seal breaking action to allow medicament penetration into injector device from the loaded cartridge followed by injection into the patient while maintaining closed sterile space of the medication.

(8) Reduction of errors from the reduced cognitive load of simply selecting the needed cartridge and inserting it into the device.

(9) Increased speed of medication delivery means delays in giving life-saving medications can be avoided.

(10) Ease of use for non-trained providers in emergency situations such as first aid delivery of epinephrine in anaphylaxis allergy or naloxone delivery in opioid overdose or antidote to biological/chemical warfare.

(11) Reduced bulk where volume of medications/device is important (aerospace medicine, pre-hospital medicine, military/tactical medicine, and bystander medicine).

(12) Once the medicament from the pre-filled cartridge has fully been administered, the cartridge will automatically eject from the injector device and decouple. This will return the injector and cartridge back into its native closed state and in some instances allow subsequent coupling of the injector with additional cartridges if required.

(13) The injector will also be able to accommodate various modalities of medication delivery depending on the clinical situation, including but not limited to: Intravenous (IV), Intramuscular (IM), Intranasal (IN), or Intraosseous (IO) routes.

It will also be appreciated that many variations are possible within the scope of the invention described herein. The catches as herein described may be referred to as teeth. It will be understood by someone skilled in the art that many of the details provided above are by way of example only and are not intended to limit the scope of the invention which is to be determined with reference to the following claims.

What is claimed is:

1. A medicament injector comprising:
an applicator including a cartridge receptacle;
an interchangeable cartridge including a hollow body shaped to receive or contain a medicament therewithin and including a reversible barrier mechanism coupled to said body, the reversible barrier mechanism being configured to only enable release of the medicament upon the cartridge being fully inserted within the cartridge receptacle; and
a depressor resiliently biased to extend about a needle in a protected needle mode, with the depressor being retractable into the cartridge receptacle to deploy the needle, the medicament being in fluid communication with the needle when the cartridge is inserted into the cartridge receptacle and the depressor is moved from the protected needle mode to a partially retracted mode, and moving the depressor from the partially retracted mode to a fully retracted mode causes the cartridge to be automatically ejected from the cartridge receptacle thereafter following administration of the medicament.

2. The medicament injector according to claim 1, wherein the reversible barrier mechanism comprises a member that is moveable from an open position to a closed position and vice versa.

3. The medicament injector as claimed in claim 1, wherein the needle is moveable relative to the depressor.

4. The medicament injector as claimed in claim 1, wherein the depressor selectively couples to and is resiliently biased outwards relative to the cartridge, and wherein the medicament injector includes a needle assembly comprising said needle, the needle assembly being received in part within the depressor and being resiliently biased towards the cartridge relative to the depressor.

5. The medicament injector as claimed in claim 1, wherein the medicament injector includes a hub to which the needle couples, and wherein the medicament injector includes a pair of resilient members between which extends the hub.

6. The medicament injector as claimed in claim 1, wherein the depressor has an inner bore, an outer bore, and a shoulder extending radially between said bores, wherein the medicament injector includes a first resilient member extending between the cartridge and the depressor, wherein the medicament injector includes a needle assembly comprising said needle and a hub to which the needle couples, the hub being received within and being movable relative to the inner bore of the depressor, and wherein the medicament injector includes a second resilient member extending between the hub and the shoulder of said depressor.

7. The medicament injector as claimed in claim 6, wherein the needle is a first said needle and wherein the needle assembly includes a second said needle in fluid communication with the first said needle, the second said needle coupling to the hub and extending towards the cartridge.

8. The medicament injector as claimed in claim 1, wherein the depressor is positioned to fully extend about the needle when the cartridge is decoupled or removed from the injector.

9. A kit comprising a plurality of interchangeable cartridges and the medicament injector as claimed in claim 1.

10. The medicament injector as claimed in claim 1, wherein the applicator includes a body and includes a reversible barrier mechanism coupled to the body thereof, the reversible barrier mechanism of the applicator being configured to only enable release of the medicament upon the cartridge being fully inserted within the cartridge receptacle and wherein the reversible barrier mechanism of the applicator is configured to return to a closed position when the cartridge is removed from the cartridge receptacle of the applicator.

11. A medicament injector comprising:
an applicator including a cartridge-accepting receptacle and a depressor; and
an interchangeable cartridge shaped to receive or contain a medicament within an interior thereof, partial retraction of the depressor releasing the medicament when the cartridge is inserted into the cartridge-accepting receptacle, and further retraction of the depressor thereafter causing the cartridge to be automatically ejected from the cartridge-accepting receptacle once the medicament has been delivered.

12. The medicament injector as claimed in claim 11 wherein the cartridge-accepting receptacle includes a first of a female member and a male member, wherein the medicament injector includes a second of the female member and the male member, the female member and the male member interengaging when the cartridge is fully inserted into the cartridge-accepting receptacle and inhibiting removal of the cartridge from the cartridge-accepting receptacle, and wherein movement of the depressor to a fully retracted mode causes the male member to selectively dislodge from the female member and biases the cartridge outwards from the cartridge-accepting receptacle.

13. The medicament injector as claimed in claim 12 wherein the male member is a tapered catch, wherein the female member comprises a recessed portion, the tapered catch being received within said recessed portion when the cartridge is fully inserted into the cartridge-accepting receptacle, and wherein the medicament injector further includes an inner tapered member that abuts against the tapered catch and causes the tapered catch to dislodge from the recessed portion when the depressor is moved to the fully retracted mode.

14. The medicament injector as claimed in claim 11 wherein the cartridge-accepting receptacle includes at least one radially-inwardly extending catch, wherein the medicament injector includes a cartridge retaining member with at least one resilient, radially-outwardly extending catch which selectively couples to said at least one radially-inwardly extending catch of the cartridge-accepting receptacle when the cartridge is fully inserted into the cartridge-accepting receptacle, and wherein the cartridge includes a dislodgement member that abuts against a first of said catches and biases said first of said catches away from a second of said catches when the depressor is moved to the fully retracted mode.

15. A kit comprising a plurality of interchangeable cartridges and the medicament injector as claimed in claim 11.

16. A medicament injector comprising:
an applicator including a cartridge-accepting receptacle and a depressor; and
an interchangeable cartridge shaped to receive or contain a medicament within an interior thereof, the cartridge coupling to and being biased outwards from the cartridge-accepting receptacle, partial retraction of the depressor thereafter releasing the medicament, and further retraction of the depressor decoupling the cartridge from the cartridge-accepting receptacle and thus enabling the applicator to accept a further said cartridge.

17. The medicament injector as claimed in claim 16, wherein the cartridge couples to the cartridge-accepting receptacle via one or more catches, with the further retraction of the depressor dislodging said one or more catches.

18. The medicament injector as claimed in claim 16 wherein the applicator includes a valve which opens when the cartridge is fully inserted into the cartridge-accepting receptacle and which closes in the process of the cartridge being ejected from the cartridge-accepting receptacle.

19. The medicament injector as claimed in claim 16 wherein the cartridge includes a reversible barrier member which opens when the cartridge is fully inserted into the cartridge-accepting receptacle.

20. A kit comprising a plurality of interchangeable cartridges and the medicament injector as claimed in claim 16.

21. A medicament injector comprising:

an applicator including a body and a cartridge-accepting receptacle;

a reversible barrier mechanism within the cartridge-accepting receptacle thereof;

an interchangeable cartridge including a hollow body shaped to receive or contain a medicament therewithin, wherein the reversible barrier mechanism is configured to only enable release of the medicament upon the cartridge being fully inserted within the cartridge-accepting receptacle of the applicator and wherein the reversible barrier mechanism is configured to return to a closed position when the cartridge is removed from the cartridge-accepting receptacle of the applicator; and a depressor resiliently biased to extend about a needle in a protected needle mode, with the depressor being retractable into the cartridge-accepting receptacle to deploy the needle, the medicament being in fluid communication with the needle when the cartridge is inserted into the cartridge-accepting receptacle and the depressor is moved from the protected needle mode to a partially retracted mode, and moving the depressor from the partially retracted mode to a fully retracted mode causes the cartridge to be automatically ejected from the cartridge-accepting receptacle thereafter following administration of the medicament.

22. The medicament injector as claimed in claim 21 wherein the reversible barrier mechanism is a part of the applicator.

* * * * *